US012600996B2

(12) United States Patent (10) Patent No.: US 12,600,996 B2
Westh et al. (45) **Date of Patent: \*Apr. 14, 2026**

(54) CARBOHYDRATE BINDING MODULE VARIANTS AND HYBRID POLYPEPTIDES COMPRISING SAME

(71) Applicant: Novozymes A/S, Bagsvaerd (DK)

(72) Inventors: Peter Westh, Copenhagen (DK); Kim Borch, Birkerød (DK); Trine Soerensen, Copenhagen (DK); Michael Windahl, Stenløse (DK); Brett McBrayer, Sacramento, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/812,259

(22) Filed: Jul. 13, 2022

(65) Prior Publication Data

US 2022/0364133 A1 Nov. 17, 2022

Related U.S. Application Data

(62) Division of application No. 15/508,631, filed as application No. PCT/US2015/048620 on Sep. 4, 2015, now Pat. No. 11,390,898.

(60) Provisional application No. 62/046,344, filed on Sep. 5, 2014.

(51) Int. Cl.
| | |
|---|---|
| *C12N 9/42* | (2006.01) |
| *C12N 15/82* | (2006.01) |
| *C12P 5/02* | (2006.01) |
| *C12P 7/14* | (2006.01) |
| *C12P 7/16* | (2006.01) |
| *C12P 7/18* | (2006.01) |
| *C12P 7/20* | (2006.01) |
| *C12P 19/02* | (2006.01) |
| *C12P 19/14* | (2006.01) |

(52) U.S. Cl.
CPC ........... *C12P 19/14* (2013.01); *C12N 9/2437* (2013.01); *C12N 15/8257* (2013.01); *C12P 5/02* (2013.01); *C12P 7/14* (2013.01); *C12P 7/16* (2013.01); *C12P 7/18* (2013.01); *C12P 7/20* (2013.01); *C12P 19/02* (2013.01); *C12Y 302/01091* (2013.01); *C07K 2319/00* (2013.01); *C12P 2203/00* (2013.01)

(58) Field of Classification Search
CPC .... C12P 19/14; C12P 5/02; C12P 7/14; C12P 7/16; C12P 7/18; C12P 7/20; C12P 19/02; C12P 2203/00; C12N 9/2437; C12N 15/8257; C12Y 302/01091; C07K 2319/00
See application file for complete search history.

(56) References Cited

U.S. PATENT DOCUMENTS

| | | | |
|---|---|---|---|
| 6,407,208 B1 * | 6/2002 | Chen .............. | C12Y 302/01091 536/23.4 |
| 7,375,197 B2 | 5/2008 | Adney et al. | |
| 7,741,093 B2 * | 6/2010 | Vehmaanpera ............................ | C12Y 302/01004 536/23.4 |
| 7,785,853 B2 | 8/2010 | Lange et al. | |
| 8,637,293 B2 | 1/2014 | Adney et al. | |
| 2006/0246566 A1 | 11/2006 | Vehmaanpera et al. | |
| 2010/0204080 A1 | 8/2010 | Vehmaanperae | |
| 2010/0306879 A1 | 12/2010 | Liu et al. | |
| 2012/0096597 A1 | 4/2012 | Schnorr et al. | |
| 2013/0040346 A1 | 2/2013 | Wogulis | |
| 2014/0065671 A1 | 3/2014 | Stringer et al. | |
| 2014/0080178 A1 * | 3/2014 | Schnorr .............. | C12N 15/8246 435/254.5 |
| 2014/0106408 A1 | 4/2014 | Mitchinson et al. | |
| 2014/0134677 A1 | 5/2014 | Mitchinson et al. | |
| 2015/0004655 A1 | 1/2015 | Wogulis | |

FOREIGN PATENT DOCUMENTS

| | | |
|---|---|---|
| NO | 2013029176 A1 | 3/2013 |
| WO | 2004016760 A2 | 2/2004 |
| WO | 2005001065 A2 | 1/2005 |
| WO | 2005028636 A2 | 3/2005 |
| WO | 2005030926 A2 | 4/2005 |
| WO | 2006117432 A1 | 11/2006 |
| WO | 2007118935 A1 | 10/2007 |
| WO | 2010060056 A2 | 5/2010 |
| WO | 2010096931 A1 | 9/2010 |
| WO | 2011050037 A1 | 4/2011 |
| WO | 2011097713 A1 | 8/2011 |
| WO | 2011098551 A2 | 8/2011 |
| WO | 2011117728 A2 | 9/2011 |
| WO | 2012048171 A2 | 4/2012 |
| WO | 2012051055 A2 | 4/2012 |
| WO | 2012078656 A1 | 6/2012 |
| WO | 2012104239 A2 | 9/2012 |
| WO | 2012135719 A1 | 10/2012 |
| WO | 2013052831 A1 | 6/2013 |

(Continued)

OTHER PUBLICATIONS

Huang et al., GenBank accession No. AFD01232 Mar. 12, 2012.*
Meera, B., GenBank accession No. AFJ54162 May 16, 2012.*
Meerupati et al., GenBank accession No. EPS44926 Jul. 23, 2013.*
Fedorova et al., GenBank accession No. EDP49733 Apr. 18, 2008.*

(Continued)

*Primary Examiner* — Delia M Ramirez
(74) *Attorney, Agent, or Firm* — David A. Fazzolare

(57) ABSTRACT

The present invention relates to cellobiohydrolase variants and carbohydrate binding module variants. The present invention also relates to polynucleotides encoding the variants; nucleic acid constructs, vectors, and host cells comprising the polynucleotides; and methods of using the variants.

33 Claims, 7 Drawing Sheets

Specification includes a Sequence Listing.

(56) References Cited

FOREIGN PATENT DOCUMENTS

| WO | 2013091577 A1 | | 6/2013 |
|---|---|---|---|
| WO | 2013138357 A1 | | 9/2013 |
| WO | 2014064115 A1 | | 5/2014 |
| WO | 2014003282 A1 | | 6/2014 |
| WO | 2014093294 A1 | | 6/2014 |
| WO | WO 2014/093275 | * | 6/2014 |
| WO | 2014138672 A1 | | 9/2014 |

OTHER PUBLICATIONS

Dos Santos et al., GenBank accession No. KAF7128451 Aug. 24, 2020.*

De Vries et al., GenBank accession No. OKP11847 Dec. 19, 2016.*

Singh et al., Current Protein and Peptide Science 19(1):5-15, 2018.*

Long et al, 2012—Uniport Access No. H9C5TO.

Le Costaqueca, 2013, Bioresource Technology, 143, 196-203.

Linder, 1995, Protein Science 4, 1056-1064.

Linder, 1999, FEBS Let 447, 13-16.

Nimols, 2007, Prot Engg Design Selection, 20(4), 179-187.

Pakarinen, 2014, Biotechnol Biofuels 7(27), 1-11.

Takashima, 2007, FEBS Lett 581, 5891-5896.

Varnai, 2013, Biotechnology for Biofuels 6(30), 1-11.

Voutilainen, 2013, Appl Microbiol Biotechnol, 98, 2991-3001.

Strobel et al. 2015 Journal of Biological Chemistry, vol. 290, No. 37, pp. 22818-22826.

Strobel et al 2016, Biotechnol. and Bioengineering, vol. 113, No. 6, 1369-1374.

Devos et al., 2000, Proteins Struc, Func, Genet 41, 98-107.

Tian et, 2003, J. Mol. Biol. 333, 863-882.

Addou et al, 2009, J. Mol. Biol. 387, 416-430.

Birren et al, 2013, Genbank accession No. Q0CMT2.

Branden et al, 1991, Garland publishing Inc, 247.

Fedorova et al, 2012, Genbank accession No. A1DNLO.

Guo et al, 2004, Proc Natl Acad Sci U S A 101, 9205-9210.

Kohler et al, 2015, Genbank accession No. KIK57628.

Long et al, 2012, Genbank accession No. AFD50192.

Sadowski et al, 2009, Curr Op Struct Biol 19, 357-362.

Seffernick et al, 2001, J Bacteriol 183(8), 2405-2410.

Tang et al, 2013, Phil Trans R Soc B 368, 1-10.

Takashima et al, 1996, Genbank accession No. Q12621.

Witkowski et al, 1999, Biochemistry 38, 11643-11650.

NIERMAN_2008_Genbank_accession_no._ XP_751044.

* cited by examiner

```
       M  Y  R  K  L  A  V  I  S  A  F  L  A  T  A  R  A  Q  S  A  C  T  L  Q  S  E  T
    1  ATGTATCGGAAGTTGGCCGTCATCTCGGCCTTCTTGGCCACAGCTCGTGCTCAGTCGGCCTGCACTCTCCAATCGGAGAC
       H  P  P  L  T  W  Q  K  C  S  S  G  G  T  C  T  Q  Q  T  G  S  V  V  I  D  A  N
   81  TCACCCGCCTCTGACATGGCAGAAATGCTCGTCTGGTGGCACGTGCACTCAACAGACAGGCTCCGTGGTCATCGACGCCA
       W  R  W  T  H  A  T  N  S  S  T  N  C  Y  D  G  N  T  W  S  S  T  L  C  P  D
  161  ACTGGCGCTGGACTCACGCTACGAACAGCAGCACGAACTGCTACGATGGCAACACTTGGAGCTCGACCCTATGTCCTGAC
       N  E  T  C  A  K  N  C  C  L  D  G  A  A  Y  A  S  T  Y  G  V  T  T  S  G  N  S
  241  AACGAGACCTGCGCGAAGAACTGCTGTCTGGACGGTGCCGCCTACGCGTCCACGTACGGAGTTACCACGAGCGGTAACAG
       L  S  I  G  F  V  T  Q  S  A  Q  K  N  V  G  A  R  L  Y  L  M  A  S  D  T  T  Y
  321  CCTCTCCATTGGCTTTGTCACCCAGTCTGCGCAGAAGAACGTTGGCGCTCGCCTTTACCTTATGGCGAGCGACACGACCT
       Q  E  F  T  L  L  G  N  E  F  S  F  D  V  D  V  S  Q  L  P  C  G  L  N  G  A
  401  ACCAGGAATTCACCCTGCTTGGCAACGAGTTCTCTTTCGATGTTGATGTTTCGCAGCTGCCCGTGCGGCTTGAACGGAGCT
       L  Y  F  V  S  M  D  A  D  G  G  V  S  K  Y  P  T  N  T  A  G  A  K  Y  G  T  G
  481  CTCTACTTCGTGTCCATGGACGCGGATGGTGGCGTGAGCAAGTATCCCACCAACACCGCTGGCGCCAAGTACGGCACGGG
       Y  C  D  S  Q  C  P  R  D  L  K  F  I  N  G  Q  A  N  V  E  G  W  E  P  S  S  N
  561  GTACTGTGACAGCCAGTGTCCCCGCGATCTGAAGTTCATCAATGGCCAGGCCAACGTTGAGGGCTGGGAGCCGTCATCCA
       N  A  N  T  G  I  G  G  H  G  S  C  C  S  E  M  D  I  W  E  A  N  S  I  S  E
  641  ACAACGCGAACACGGGCATTGGAGGACACGGAAGCTGCTGCTCTGAGATGGATATCTGGGAGGCCAACTCCATCTCCGAG
       A  L  T  P  H  P  C  T  T  V  G  Q  E  I  C  E  G  D  G  C  G  G  T  Y  S  D  N
  721  GCTCTTACCCCCCACCCTTGCACGACTGTCGGCCAGGAGATCTGCGAGGGTGATGGGTGCGGCGGAACTTACTCCGATAA
       R  Y  G  G  T  C  D  P  D  G  C  D  W  N  P  Y  R  L  G  N  T  S  F  Y  G  P  G
  801  CAGATATGGCGGCACTTGCGATCCCGATGGCTGCGACTGGAACCCATACCGCCTGGGCAACACCAGCTTCTACGGCCCTG
       S  S  F  T  L  D  T  T  T  K  K  L  T  V  V  T  Q  F  E  T  S  G  A  I  N  R  Y
  881  GCTCAAGCTTTACCCTCGATACCACCAAGAAATTGACCGTTGTCACCCAGTTCGAGACGTCGGGTGCCATCAACCGATAC
       Y  V  Q  N  G  V  T  F  Q  Q  P  N  A  E  L  G  S  Y  S  G  N  E  L  N  D  D  Y
  961  TATGTCCAGAATGGCGTCACTTTCCAGCAGCCCAACGCCGAGCTTGGTAGTTACTCTGGCAACGAGCTCAACGATGATTA
       C  T  A  E  E  A  E  F  G  G  S  S  F  S  D  K  G  G  L  T  Q  F  K  K  A  T  S
 1041  CTGCACAGCTGAGGAGGCAGAATTCGGCGGATCCTCTTTCTCAGACAAGGGCGGCCTGACTCAGTTCAAGAAGGCTACCT
       G  G  M  V  L  V  M  S  L  W  D  D  Y  Y  A  N  M  L  W  L  D  S  T  Y  P  T
 1121  CTGGCGGCATGGTTCTGGTCATGAGTCTGTGGGATGATTACTACGCCAACATGCTGTGGCTGGACTCCACCTACCCGACA
       N  E  T  S  S  T  P  G  A  V  R  G  S  C  S  T  S  S  G  V  P  A  Q  V  E  S  Q
 1201  AACGAGACCTCCTCCACACCCGGTGCCGTGCGCGGAAGCTGCTCCACCAGCTCCGGTGTCCCTGCTCAGGTCGAATCTCA
       S  P  N  A  K  V  T  F  S  N  I  K  F  G  P  I  G  S  T  G  N  P  S  G  G  N  P
 1281  GTCTCCCAACGCCAAGGTCACCTTCTCCAACATCAAGTTCGGACCCATTGGCAGCACCGGCAACCCTAGCGGCGGCAACC
       P  G  G  N  P  P  G  T  T  T  T  R  R  P  A  T  T  T  G  S  S  P  G  P  T  Q
 1361  CTCCCGGCGGAAACCCGCCTGGCACCACCACCACCCGCCGCCCAGCCACTACCACTGGAAGCTCTCCCGGACCTACCCAG
       S  H  Y  G  Q  C  G  G  I  G  Y  S  G  P  T  V  C  A  S  G  T  T  C  Q  V  L  N
 1441  TCTCACTACGGCCAGTGCGGCGGTATTGGCTACAGCGGCCCCACGGTCTGCGCCAGCGGCACAACTTGCCAGGTCCTGAA
       P  Y  Y  S  Q  C  L
 1521  CCCTTACTACTCTCAGTGCCTGTAA
```

Fig. 1

SEQUENCE LISTING

```
Sequence total quantity: 100
SEQ ID NO: 1              moltype = DNA  length = 1893
FEATURE                   Location/Qualifiers
source                    1..1893
                          mol_type = genomic DNA
                          organism = Trichoderma reesei
SEQUENCE: 1
caactcagat cctccaggag acttgtacac catcttttga ggcacagaaa cccaatagtc    60
aaccgcggac tgcgcatcat gtatcggaag ttggccgtca tctcggcctt cttggccaca   120
gctcgtgctc agtcggcctg cactctccaa tcggagactc acccgcctct gacatggcag   180
aaatgctcgt ctggtggcac gtgcactcaa cagacaggct ccgtggtcat cgacgccaac   240
tggcgctgga ctcacgctac gaacagcagc acgaactgct acgatggcaa cacttggagc   300
tcgaccctat gtcctgacaa cgagacctgc gcgaagaact gctgtctgga cggtgccgcc   360
tacgcgtcca cgtacggagt taccacgagc ggtaacagcc tctccattgg ctttgtcacc   420
cagtctcgcg agaagaacgt tggcgctcgc ctttacctta tggcgagcga cacgacctac   480
caggaattca ccctgcttgg caacgagttc tctttcgatg ttgatgtttc gcagctgccg   540
tgcggcttga acggagctct ctacttcgtg tccatggacg cggatggtgg cgtgagcaag   600
tatcccacca acaccgctgg cgccaagtac ggcacggggt actgtgacag ccagtgtccc   660
cgcgatctga agttcatcaa tggccaggcc aacgttgagg gctgggagcc gtcatccaac   720
aacgcgaaca cgggcattgg aggacacgga agctgctgct ctgagatgga tatctgggag   780
gccaactcca tctccgaggc tcttacccccc caccccttgca cgactgtcgg ccaggagatc   840
tgcgagggtg atgggtgcgg cggaacttac tccgataaca gatatggcgg cacttgcgat   900
cccgatggct gcgactggaa cccataccgc ctgggcaaca ccagcttcta cggccctggc   960
tcaagctttta ccctcgatac caccaagaaa ttgaccgttg tcacccagtt cgagacgtcg  1020
ggtgccatca accgatacta tgtccagaat ggcgtcactt tccagcagcc caacgccgag  1080
cttggtagtt actctggcaa cgagctcaac gatgattact gcacagctga ggaggcagaa  1140
ttcggcggat cctcttttctc agacaagggc ggcctgactc agttcaagaa ggctacctct  1200
ggcggcatgg ttctggtcat gagtctgtgg gatgattact acgccaacat gctgtggctg  1260
gactccacct acccgacaaa cgagacctcc tccacacccg gtgccgtgcg cggaagctgc  1320
tccaccagct ccggtgtccc tgctcaggtc gaatctcagt ctcccaacgc caaggtcacc  1380
ttctccaaca tcaagttcgg acccattggc agcaccggca acccctagcgg cggcaaccct  1440
cccggcggaa acccgcctgg caccaccacc acccgccgcc cagccactac cactggaagc  1500
tctcccggac ctacccagtc tcactacggc cagtgcggcg gtattggcta cagcggcccc  1560
acggtctgcg ccagcggcac aacttgccag gtcctgaacc cttactactc tcagtgcctg  1620
taaagctccg tggcgaaagc ctgacgcacc ggtagattct tggtgagccc gtatcatgac  1680
ggcggcggga gctacatggc cccgggtgat ttatttttttt tgtatctact tctgacccttt  1740
ttcaaatata cggtcaactc atctttcact ggagatgcgg cctgcttggt attgcgatgt  1800
tgtcagcttg gcaaattgtg gctttcgaaa acacaaaacg attccttagt agccatgcat  1860
tttaagataa cggaatagaa gaaagaggaa att                                1893

SEQ ID NO: 2              moltype = AA  length = 514
FEATURE                   Location/Qualifiers
source                    1..514
                          mol_type = protein
                          organism = Trichoderma reesei
SEQUENCE: 2
MYRKLAVISA FLATARAQSA CTLQSETHPP LTWQKCSSGG TCTQQTGSVV IDANWRWTHA    60
TNSSTNCYDG NTWSSTLCPD NETCAKNCCL DGAAYASTYG VTTSGNSLSI GFVTQSAQKN   120
VGARLYLMAS DTTYQEFTLL GNEFSFDVDV SQLPCGLNGA LYFVSMDADG GVSKYPTNTA   180
GAKYGTGYCD SQCPRDLKFI NGQANVEGWE PSSNNANTGI GGHGSCCSEM DIWEANSISE   240
ALTPHPCTTV GQEICEGDGC GGTYSDNRYG GTCDPDGCDW NPYRLGNTSF YGPGSSFTLD   300
TTKKLTVVTQ FETSGAINRY YVQNGVTFQQ PNAELGSYSG NELNDDYCTA EEAEFGGSSF   360
SDKGGLTQFK KATSGGMVLV MSLWDDYYAN MLWLDSTYPT NETSSTPGAV RGSCSTSSGV   420
PAQVESQSPN AKVTFSNIKF GPIGSTGNPS GGNPPGGNPP GTTTTRRPAT TTGSSPGPTQ   480
SHYGQCGGIG YSGPTVCASG TTCQVLNPYY SQCL                               514

SEQ ID NO: 3              moltype = DNA  length = 108
FEATURE                   Location/Qualifiers
source                    1..108
                          mol_type = other DNA
                          organism = Trichoderma reesei
```

```
SEQUENCE: 3
acccagtctc actacggcca gtgcggcggt attggctaca gcggccccac ggtctgcgcc   60
agcggcacaa cttgccaggt cctgaaccct tactactctc agtgcctg                108

SEQ ID NO: 4           moltype = AA  length = 36
FEATURE                Location/Qualifiers
source                 1..36
                       mol_type = protein
                       organism = Trichoderma reesei
SEQUENCE: 4
TQSHYGQCGG IGYSGPTVCA SGTTCQVLNP YYSQCL                                 36

SEQ ID NO: 5           moltype = DNA  length = 1638
FEATURE                Location/Qualifiers
source                 1..1638
                       mol_type = genomic DNA
                       organism = Humicola insolens
SEQUENCE: 5
atgcgtaccg ccaagttcgc caccctcgcc gcccttgtgg cctcggccgc cgcccagcag   60
gcgtgcagtc tcaccaccga gaggcaccct tccctctctt ggaacaagtg caccgccggc  120
ggccagtgcc agaccgtcca ggcttccatc actctcgact ccaactggcg ctggactcac  180
caggtgtctg gctccaccaa ctgctacacg ggcaacagt ggatactag catctgcact   240
gatgccaagt cgtgcgctca gaactgctgc gtcgatggtg ccgactacac cagcacctat  300
ggcatcacca ccaacggtga ttccctgagc ctcaagttcg tcaccaaggg ccagcactcg  360
accaacgtcg gctcgcgtac ctacctgatg gacggcgagg acaagtatca gagtacgttc  420
tatcttcagc cttctcgcgc cttgaatcct ggctaacgtt tacacttcac agccttcgac  480
ctcctcggca acgagttcac cttcgatgtc gatgtctcca acatcggctg cggtctcaac  540
ggcgccctgt acttcgtctc catggacgcc gatggtggtc tcagccgcta tcctggcaac  600
aaggctggtg ccaagtacgg taccggctac tgcgatgctc agtgccccg tgacatcaag   660
ttcatcaacg gcgaggccaa cattgagggc tggaccggct ccaacaacga ccccaacgcc  720
ggcgcgggcc gctatggtac ctgctgctct gagatggata tctgggaagc caacaacatg  780
gctactgcct tcactcctca cccttgcacc atcattggcc agagccgctg cgagggcgac  840
tcgtgcggtg gcacctacag caacgagcgc tacgccggcg tctgcgaccc cgatggctgc  900
gacttcaact cgtaccgcca gggcaacaag accttctacg gacagggcat gaccgtcgac  960
accaccaaga agatcactgt cgtcacccag ttcctcaagg atgccaacga cgatctcggc 1020
gagatcaagc gcttctacgt ccaggatggc aagatcatcc ccaactccga gtccaccatc 1080
cccggcgtcg agggcaattc catcacccag gactggtgcg accgcagaa ggttgccttt 1140
ggcgacattg acgacttcaa ccgcaagggc ggcatgaagc agatgggcaa ggccctcgcc 1200
ggcccaatgg tcctggtcat gtccatctgg gatgaccacg cctccaacat gctctggctc 1260
gactcgacct tccctgtcga tgccgctggc aagcccggcg ccgagcgcgg tgcctgcccg 1320
accacctcgg gtgtccctgc tgaggttgag gccgaggccc ccaacagcaa cgtcgtcttc 1380
tccaacatcc gcttcggccc catcggctcg accgttgctg tctcccggg cgcgggcaac 1440
ggcggcaaca acggcggcaa cccccgccc cccaccacca ccacctcctc ggctccggac 1500
accaccacca ccgccagcgc tggccccaag gctggccgct ggcagcagtg cggcggcatc 1560
ggcttcactg gcccgaccca gtgcgaggag ccctacattt gcaccaagct caacgactgg 1620
tactctcagt gcctgtaa                                                1638

SEQ ID NO: 6           moltype = AA  length = 525
FEATURE                Location/Qualifiers
source                 1..525
                       mol_type = protein
                       organism = Humicola insolens
SEQUENCE: 6
MRTAKFATLA ALVASAAAQQ ACSLTTERHP SLSWNKCTAG GQCQTVQASI TLDSNWRWTH   60
QVSGSTNCYT GNKWDTSICT DAKSCAQNCC VDGADYTSTY GITTNGDSLS LKFVTKGQHS  120
TNVGSRTYLM DGEDKYQTFE LLGNEFTFDV DVSNIGCGLN GALYFVSMDA DGGLSRYPGN  180
KAGAKYGTGY CDAQCPRDIK FINGEANIEG WTGSTNDPNA GAGRYGTCCS EMDIWEANNM  240
ATAFTPHPCT IIGQSRCEGD SCGGTYSNER YAGVCDPDGC DFNSYRQGNK TFYGKGMTVD  300
TTKKITVVTQ FLKDANGDLG EIKRFYVQDG KIIPNSESTI PGVEGNSITQ DWCDRQKVAF  360
GDIDDFNRKG GMKQMGKALA GPMVLVMSIW DDHASNMLWL DSTFPVDAAG KPGAERGACP  420
TTSGVPAEVE AEAPNSNVVF SNIRFGPIGS TVAGLPGAGN GGNNGGNPPP PTTTTSSAPA  480
TTTTASAGPK AGRWQQCGGI GFTGPTQCEE PYICTKLNDW YSQCL                   525

SEQ ID NO: 7           moltype = DNA  length = 110
FEATURE                Location/Qualifiers
source                 1..110
                       mol_type = other DNA
                       organism = Humicola insolens
SEQUENCE: 7
cccaaggctg ccgctggca gcagtgcggc ggcatcggct tcactggccc gacccagtgc   60
gaggagccct acatttgcac caagctcaac gactggtact ctcagtgcct                110

SEQ ID NO: 8           moltype = AA  length = 37
FEATURE                Location/Qualifiers
source                 1..37
                       mol_type = protein
                       organism = Humicola insolens
SEQUENCE: 8
PKAGRWQQCG GIGFTGPTQC EEPYICTKLN DWYSQCL                                37
```

```
SEQ ID NO: 9                moltype = DNA  length = 1593
FEATURE                     Location/Qualifiers
source                      1..1593
                            mol_type = genomic DNA
                            organism = Chaetomium thermophilum
SEQUENCE: 9
atgatgtaca agaagttcgc cgctctcgcc gccctcgtgg ctggcgccgc cgcccagcag   60
gcttgctccc tcaccactga gacccacccc agactcactt ggaagcgctg cacctctggc  120
ggcaactgct cgaccgtgaa cggcgccgtc accatcgatg ccaactggcg ctggactcac  180
actgtttccg gctcgaccaa ctgctacacc ggcaacgagt gggatacctc catctgctct  240
gatggcaaga gctgcgccca gacctgctgc gtcgacggcg ctgactactc ttcgacctat  300
ggtatcacca ccagcggtga ctccctgaac ctcaagttcg tcaccaagca ccagcacggc  360
accaatgtcg gctctcgtgt ctacctgatg gagaacgaca ccaagtacca gatgttcgag  420
ctcctcggca acgagttcac cttcgatgtc gatgtctcta acctgggctg cggtctcaac  480
ggcgccctct acttcgtctc catggacgct gatggtggta tgagcaagta ctctggcaac  540
aaggctggcg ccaagtacgg taccggctac tgcgatgctc agtgcccgcg cgaccttaag  600
ttcatcaacg gcgaggccaa cattgagaac tggacccctc agactgacgc tgccaacgcc  660
ggtttcggcc gctatggcag ctgctgctct gagatggata tctgggatgc caacaacatg  720
gctactgcct tcactcctca cccttgcacc attatcggcc agagccgctg cgagggcaac  780
agctgcggtg gcacctacag ctctgagcgc tatgctggtg tttgcgatcc tgatggctgc  840
gacttcaacg cctaccgcca gggcgacaag accttctacg gcaagggcat gaccgtcgaa  900
accaccaaga agatgaccgt cgtcacccag ttccacaaga actcggctgg cgtcctcagc  960
gagatcaagc gcttctacgt tcaggacggc aagatcattg ccaacgccga gtccaagatc 1020
cccggcaacc ccggcaactc catcacccag gagtggtgcg atgcccagaa ggtcgccttc 1080
ggtgacatcg atgacttcaa ccgcaagggc ggtatgagac agggaaacag tatcacgcag 1140
ggccctatgg tcctggtcat gtccgtctgg gatgaccact acgccaacat gctctggctc 1200
gactcgacct acccccattga caaggccggc accccccggcg ccgagcgcgg tgcttgcccg 1260
accacctccg tgtgccctgc cgagattgag gcccaggtcc ccaacagcaa cgttatcttc 1320
tccaacatcc gcttcggccc catcggctcg accgtccctg acggtagcac tcccaacccc 1380
agcaacccga ccgccaccgt tgctcctccc acttctacca ccaccagcgt gagaagcagc 1440
actactcaga tttccacccc gactagccag cccggcggct gcaccaccca gaagtggggc 1500
cagtgcggtg gtatcggcta caccggctgc actaactgcg ttgctggcac tacctgcact 1560
gagctcaacc cctggtacag ccagtgcctg taa                              1593

SEQ ID NO: 10               moltype = AA  length = 530
FEATURE                     Location/Qualifiers
source                      1..530
                            mol_type = protein
                            organism = Chaetomium thermophilum
SEQUENCE: 10
MMYKKFAALA ALVAGAAAQQ ACSLTTETHP RLTWKRCTSG GNCSTVNGAV TIDANWRWTH   60
TVSGSTNCYT GNEWDTSICS DGKSCAQTCC VDGADYSSTY GITTSGDSLN LKFVTKHQHG  120
TNVGSRVYLM ENDTKYQMFE LLGNEFTFDV DVSNLGCGLN GALYFVSMDA DGGMSKYSGN  180
KAGAKYGTGY CDAQCPRDLK FINGEANIEN WTPSTNDANA GFGRYGSCCS EMDIWDANNM  240
ATAFTPHPCT IIGQSRCEGN SCGGTYSSER YAGVCDPDGC DFNAYRQGDK TFYGKGMTVD  300
TTKKMTVVTQ FHKNSAGVLS EIKRFYVQDG KIIANAESKI PGNPGNSITQ EWCDAQKVAF  360
GDIDDFNRKG GMAQMSKALE GPMVLVMSVW DDHYANMLWL DSTYPIDKAG TPGAERGACP  420
TTSGVPAEIE AQVPNSNVIF SNIRFGPIGS TVPGLDGSTP SNPTATVAPP TSTTTSVRSS  480
TTQISTPTSQ PGGCTTQKWG QCGGIGYTGC TNCVAGTTCT ELNPWYSQCL             530

SEQ ID NO: 11               moltype = DNA  length = 117
FEATURE                     Location/Qualifiers
source                      1..117
                            mol_type = other DNA
                            organism = Chaetomium thermophilum
SEQUENCE: 11
ggcggctgca ccacccagaa gtggggccag tgcggtggta tcggctacac cggctgcact   60
aactgcgttg ctggcactac ctgcactgag ctcaacccct ggtacagcca gtgcctg     117

SEQ ID NO: 12               moltype = AA  length = 39
FEATURE                     Location/Qualifiers
source                      1..39
                            mol_type = protein
                            organism = Chaetomium thermophilum
SEQUENCE: 12
GGCTTQKWGQ CGGIGYTGCT NCVAGTTCTE LNPWYSQCL                          39

SEQ ID NO: 13               moltype = DNA  length = 1614
FEATURE                     Location/Qualifiers
source                      1..1614
                            mol_type = genomic DNA
                            organism = Talaromyces byssochlamydoides
SEQUENCE: 13
atgtccgcct ctctttctta cagactctac gaaaatgctc tcattctctg ttccctcgtg   60
gttgctgccc agggccagca gattggcacc ttgcaggctg aggtccaccc ttctctgact  120
tgggagacct gcagcaccgg cggcagttgt accaccatcg acggctctat cgtccttgat  180
gccaactggc gctgggtcca ccaggtcggc accagcacca ctgctatac cggcaatacc  240
tgggatacct ccatctgcga taccgatacg acctgtgccc agaatgcgc tgtcgatggt  300
```

-continued

```
gctgactacg agagcaccta cggtatcacc accagcggca atgaagttcg tctcaacttt  360
gtcaccgaca actcgaatgg agcgaacgtc ggctcccgtg tctacctaat ggcggatgac  420
acccactacc agatcttcaa tctgctgaac caggagttta ccttcacagt ggatgtctca  480
aacctgccct gcggtctcaa cggcgccctc tacctcgttg ttatggatgc cgacggtggt  540
gtatccgagt atacgaataa tgccggctgg gctcagtatg gtgtgggcta ctgtgactcg  600
cagtgtcccc gagatctcaa gttcatccaa ggccaggcca acgttgaggg ctggacacct  660
tcctccaata atgccaatac tggtgttggg aacctcgggt cctgctgtgc agaaatagat  720
atctgggaat cgaacagcat ttctcaagcg cttaccgccc atccgtgcaa cactcccaca  780
aatacggtgt gtgatggcaa cgcctgcggt ggcacataca gcactactcg ctatgctggc  840
acttgtgatc ctgatggctg tgatttcaac ccgtaccggt tgggcaacac gactttctat  900
ggtcctggca tgactattga taccacccag ccgatcaccg ttgtcactca gttcatcact  960
gatgatggaa cttccactgg caccttgtct gaaattaagc gctactacat tcagaacgac  1020
gtcgtgtatg cccagcccaa ctccgacatc gctggcatta ctggaaatgt cattgatgcc  1080
gcttactgta ccgctgagaa ttctgtcttc caagaagagg gttccttcgc acaacacggt  1140
ggcatgagtg gtgtcagtga ggctctgtcc gctggtatgg tcttggtcat gagcgtgtgg  1200
gatgactacg acgccaatat gctgtggctc gacagcgact acccaaccaa cgagtctaca  1260
agcacccccg gtgtggcccg aggtagctgt tccacttcct ctggtgttcc cgccaccgtt  1320
gaatcccaga gccctaactc ctatgtgatc tactcgaaca tcaaggttgg tcccatcggc  1380
tcgaccttca gttccggtgg ttctggcagt ggctctggcg gcggttccgg tggctctagc  1440
accactacaa ccaccacttc gtccacgccc acgactacca gctcttccgg ctctggcagt  1500
ggcgtcgctc agcactgggg acagtgcggt ggtgagggct ggactggccc aactacctgt  1560
gcctcccgt acacctgtca ggagcagaac ccttactact cccagtgtct gtaa  1614
```

```
SEQ ID NO: 14          moltype = AA   length = 537
FEATURE                Location/Qualifiers
source                 1..537
                       mol_type = protein
                       organism = Talaromyces byssochlamydoides
SEQUENCE: 14
MSASLSYRLY ENALILCSLV VAAQGQQIGT LQAEVHPSLT WETCSTGGSC TTIDGSIVLD  60
ANWRWVHQVG TSTNCYTGNT WDTSICDTDT TCAQECAVDG ADYESTYGIT TSGNEVRLNF  120
VTDNSNGANV GSRVYLMADD THYQIFNLLN QEFTFTVDVS NLPCGLNGAL YLVVMDADGG  180
VSEYTNNAAG AQYGVGYCDS QCPRDLKFIQ GQANVEGWTP SSNNANTGVG NLGSCCAEID  240
IWESNSISQA LTAHPCNTPT NTVCDGNACG GTYSTTRYAG TCDPDGCDFN PYRLGNTTFY  300
GPGMTIDTTQ PITVVTQFIT DDGTSTGTLS EIKRYYIQND VVYAQPNSDI AGITGNVIDA  360
AYCTAENSVF QEEGSFAQHG GMSGVSEALS AGMVLVMSVW DDYDANMLWL DSDYPTNEST  420
STPGVARGSC STSSGVPATV ESQSPNSYVI YSNIKVGPIG STFSSGGSGS GSGGGSGGSS  480
TTTTTTSSTP TTTSSSGSGS GVAQHWGQCG GEGWTGPTTC ASPYTCQEQN PYYSQCL  537
```

```
SEQ ID NO: 15          moltype = DNA   length = 108
FEATURE                Location/Qualifiers
source                 1..108
                       mol_type = other DNA
                       organism = Talaromyces byssochlamydoides
SEQUENCE: 15
gtcgctcagc actggggaca gtgcggtggt gagggctgga ctggcccaac tacctgtgcc  60
tccccgtaca cctgtcagga gcagaaccct tactactccc agtgtctg  108
```

```
SEQ ID NO: 16          moltype = AA   length = 36
FEATURE                Location/Qualifiers
source                 1..36
                       mol_type = protein
                       organism = Talaromyces byssochlamydoides
SEQUENCE: 16
VAQHWGQCGG EGWTGPTTCA SPYTCQEQNP YYSQCL  36
```

```
SEQ ID NO: 17          moltype = DNA   length = 1599
FEATURE                Location/Qualifiers
source                 1..1599
                       mol_type = other DNA
                       organism = Aspergillus fumigatus
SEQUENCE: 17
atgctggcct ccaccttctc ctaccgcatg tacaagaccg cgctcatcct ggccgccctt  60
ctgggctctg gccaggctca gcaggtcggt acttcccagg cggaagtgca tccgtccatg  120
acctggcaga gctgcacggc tggcggcagc tgcaccacca caacggcaa ggtggtcatc  180
gacgcgaact ggcgttgggt gcacaaagtc ggcgactaca ccaactgcta caccggcaac  240
acctgggaca cgactatctg ccctgacgat gcgacctgcg catccaactg cgcccttgag  300
ggtgccaact acgaatccac ctatggtgtg accgccagcg gcaattccct ccgcctcaac  360
ttcgtcacca ccagccagca gaagaacatt ggctcgcgtc tgtacatgat gaaggacgac  420
tcgacctacg agatgtttaa gctgctgaac caggagttca ccttcgatgt cgatgtctcc  480
aacctcccct gcggtctcaa cggtgctctg tactttgtcg ccatggacgc cggcggtggc  540
atgtccaagt acccaaccaa caaggccggt gccaagtacg gtactggata ctgtgactcg  600
cagtgccctc gcgacctcaa gttcatcaac ggtcaggcca cgttgaagg gtggcagccc  660
tcctccaacg atgccaatgc gggtaccggc aaccacggt cctgctgcgc ggagatggat  720
atctgggagg ccaacagcat ctccacggc ttcaccccc atccgtgcga cacgcccggc  780
caggtgatgt gcaccggtga tgcctgcggt ggcacctaca gctccgaccg ctacggcggc  840
acctgcgacc ccgacggatg tgatttcaac tccttccgcc agggcaacaa gaccttctac  900
ggccctggca tgaccgtcga caccaagagc aagtttacc tcgtcaccca gttcatcacc  960
gacgacggca cctccagcgg caccctcaag gagatcaagc gcttctacgt gcagaacggc  1020
```

```
aaggtgatcc ccaactcgga gtcgacctgg accggcgtca gcggcaactc catcaccacc    1080
gagtactgca ccgcccagaa gagcctgttc caggaccaga acgtcttcga aaagcacggc    1140
ggcctcgagg gcatgggtgc tgccctcgcc cagggcatgg ttctcgtcat gtccctgtgg    1200
gatgatcact cggccaacat gctctggctc gacagcaact acccgaccac tgcctcttcc    1260
accactcccg gcgtcgcccg tggtacctgc gacatctcct ccggcgtccc tgcggatgtc    1320
gaggcgaacc accccgacgc ctacgtcgtc tactccaaca tcaaggtcgg ccccatcggc    1380
tcgaccttca acagcggtgg ctcgaacccc ggtggcggaa ccaccacgac aactaccacc    1440
cagcctacta ccaccacgac cacggctgga aaccctggcg gcaccggagt cgcacagcac    1500
tatggccagt gtggtggaat cggatggacc ggacccacaa cctgtgccag cccttatacc    1560
tgccagaagc tgaatgatta ttactctcag tgcctgtag                           1599

SEQ ID NO: 18              moltype = AA  length = 532
FEATURE                    Location/Qualifiers
source                     1..532
                           mol_type = protein
                           organism = Aspergillus fumigatus
SEQUENCE: 18
MLASTFSYRM YKTALILAAL LGSGQAQQVG TSQAEVHPSM TWQSCTAGGS CTTNNGKVVI    60
DANWRWVHKV GDYTNCYTGN TWDTTICPDD ATCASNCALE GANYESTYGV TASGNSLRLN    120
FVTTSQQKNI GSRLYMMKDD STYEMFKLLN QEFTFDVDVS NLPCGLNGAL YFVAMDAGGG    180
MSKYPTNKAG AKYGTGYCDS QCPRDLKFIN GQANVEGWQP SSNDANAGTG NHGSCCAEMD    240
IWEANSISTA FTPHPCDTPG QVMCTGDACG GTYSSDRYGG TCDPDGCDFN SFRQGNKTFY    300
GPGMTVDTKS KFTVVTQFIT DDGTSSGTLK EIKRFYVQNG KVIPNSESTW TGVSGNSITT    360
EYCTAQKSLF QDQNVFEKHG GLEGMGAALA QGMVLVMSLW DDHSANMLWL DSNYPTTASS    420
TTPGVARGTC DISSGVPADV EANHPDAYVV YSNIKVGPIG STFNSGGSNP GGGTTTTTTT    480
QPTTTTTTAG NPGGTGVAQH YGQCGGIGWT GPTTCASPYT CQKLNDYYSQ CL            532

SEQ ID NO: 19              moltype = DNA  length = 108
FEATURE                    Location/Qualifiers
source                     1..108
                           mol_type = other DNA
                           organism = Aspergillus fumigatus
SEQUENCE: 19
gtcgcacagc actatggcca gtgtggtgga atcggatgga ccggacccac aacctgtgcc    60
agcccttata cctgccagaa gctgaatgat tattactctc agtgcctg                 108

SEQ ID NO: 20              moltype = AA  length = 36
FEATURE                    Location/Qualifiers
source                     1..36
                           mol_type = protein
                           organism = Aspergillus fumigatus
SEQUENCE: 20
VAQHYGQCGG IGWTGPTTCA SPYTCQKLND YYSQCL                              36

SEQ ID NO: 21              moltype = DNA  length = 1581
FEATURE                    Location/Qualifiers
source                     1..1581
                           mol_type = genomic DNA
                           organism = Thielavia terrestris
SEQUENCE: 21
atgcacgcca agttcgcgac cctcgccgcc cttgtggcgt ccgccgcggc ccagcaggcc    60
tgcacactca cggctgagaa ccaccccacc ctgtcgtggt ccaagtgcac gtccggcggc    120
agctgcacca gcgtctcggg ctccgtcacc atcgatgcca actggcggtg gactcaccag    180
gtctcgagct cgaccaactg ctacacgggc aatgagtggg acacgtccat ctgcaccgac    240
ggtgcttcgt gcgccgccgc ctgctgcctc gatggcgcca actactcggg cacctatggc    300
atcaccacca gcggcaacgc cctcagcctc cagttcgtca ctcagggccc ctactcgacc    360
aacattggct cgcgtaccta cctgatggcc tcggacacca agtaccagat gttcactctg    420
ctcggcaacg agttcacctt cgacgtggac gtcacaggcc tcggctgcgg tctgaacggc    480
gccctctact tcgtctccat ggacgaggac ggtggtcttt ccaagtactc gggcaacaag    540
gctggcgcca gtacggcgac cggctactgc gactcgcagt gccccgcgca cctcaagttc    600
atcaacggcg aggctaacaa cgttggctgg accccgtcgt ccaacgacaa gaacgccggc    660
ttgggcaact acggcagctg ctgctccgag atggatgtct gggaggccaa cagcatctcg    720
gcggcctaca cgccccatcc ttgcactacc atcggccaga cgcgctgcga gggcgacgac    780
tgcggtggta cctacagcac tgaccgctac gccggcgagt gcgaccctga cggatgcgac    840
ttcaactcgt accgcatggg caacacgacc ttctacggca agggcatgac cgtcgacacc    900
agcaagaagt tcacggtggt gacccagttc ctgacggact cgtctggcaa cctgtccgag    960
atcaagcgct ctacgtccca gaacggcgtc gtcattccca ctcgaactc caacatcgcg    1020
ggcgtctcgg gcaactccat cacccaggcc ttctgcgatg ctcagaagac cgcctttcggc   1080
gacaccaacg tcttcgacca aaagggcggc ctggcccaga tgggccaaggc tcttgcccag    1140
cccatggtcc tcgtcatgtc cctctgggac gaccacgccg tcaacatgct ctggctcgac    1200
tcgacctacc gaccaacgc ggccggcaag ccgggcgccg cccgcggtac ctgccccacc     1260
acctcgggcg tccccgccga cgtcgagtcc caggcgccca ctccaaggt catctactcc     1320
aacatccgct tcggccccat cggctccacc gtctccggcc tgcccggcgg cggcagcaac    1380
cccggcggcg gctccagctc caccaccacc accaccacc caccacctcc                1440
tcggccagct ccggcccgac cgccggtggc acggctgccc actgggggcca gtgcggcggc    1500
atcggctgga ccggccgac cgtctgcgcc tcgccctaca cctgccagaa gctgaacgac     1560
tggtactacc agtgcctcta a                                              1581

SEQ ID NO: 22              moltype = AA  length = 526
```

```
FEATURE                Location/Qualifiers
source                 1..526
                       mol_type = protein
                       organism = Thielavia terrestris
SEQUENCE: 22
MHAKFATLAA LVASAAAQQA CTLTAENHPT LSWSKCTSGG SCTSVSGSVT IDANWRWTHQ   60
VSSSTNCYTG NEWDTSICTD GASCAAACCL DGADYSGTYG ITTSGNALSL QFVTQGPYST  120
NIGSRTYLMA SDTKYQMFTL LGNEFTFDVD VTGLGCGLNG ALYFVSMDED GGLSKYSGNK  180
AGAKYGTGYC DSQCPRDLKF INGEANNVGW TPSSNDKNAG LGNYGSCCSE MDVWEANSIS  240
AAYTPHPCTT IGQTRCEGDD CGGTYSTDRY AGECDPDGCD FNSYRMGNTT FYGKGMTVDT  300
SKKFTVVTQF LTDSSGNLSE IKRFYVQNGV VIPNSNSNIA GVSGNSITQA FCDAQKTAFG  360
DTNVFDQKGG LAQMGKALAQ PMVLVMSLWD DHAVNMLWLD STYPTNAAGK PGAARGTCPT  420
TSGVPADVES QAPNSKVIYS NIRFGPIGST VSGLPGGGSN PGGGSSSTTT TTRPATSTTS  480
SASSGPTGGG TAAHWGQCGG IGWTGPTVCA SPYTCQKLND WYYQCL                 526

SEQ ID NO: 23           moltype = DNA   length = 108
FEATURE                 Location/Qualifiers
source                  1..108
                        mol_type = other DNA
                        organism = Thielavia terrestris
SEQUENCE: 23
acggctgccc actggggcca gtgcggcggc atcggctgga ccggcccgac cgtctgcgcc   60
tcgccctaca cctgccagaa gctgaacgac tggtactacc agtgcctc                108

SEQ ID NO: 24           moltype = AA   length = 36
FEATURE                 Location/Qualifiers
source                  1..36
                        mol_type = protein
                        organism = Thielavia terrestris
SEQUENCE: 24
TAAHWGQCGG IGWTGPTVCA SPYTCQKLND WYYQCL                             36

SEQ ID NO: 25           moltype = DNA   length = 1578
FEATURE                 Location/Qualifiers
misc_feature            1092
                        note = n is a, c, g, or t
source                  1..1578
                        mol_type = genomic DNA
                        organism = Myceliophthora thermophilum
SEQUENCE: 25
atgtacgcca agttcgcgac cctcgccgcc cttgtggctg gcgccgctgc tcagaacgcc   60
tgcactctga ccgctgagaa ccacccctcg ctgacgtggt ccaagtgcac gtctggcggc  120
agctgcacca gcgtccaggg ttccatcacc atcgacgcca actggcggtg gactcaccgg  180
accgatagcg ccaccaactg ctacgagggc aacaagtggg atacttcgta ctgcagcgat  240
ggtccttctt cgcgcctcca agtgctgcatc gacggcgctg actactcgag cacctatggc  300
atcaccacga gcggtaactc cctgaacctc aagttcgtca ccaagggcca gtactcgacc  360
aacatcggct cgcgtaccta cctgatggag agcgacacca agtaccagtt ccagctcctc  420
ggcaacgagt tcaccttcga tgtcgacgtc tccaacctcg gctgcggcct caatggcgcc  480
ctctacttcg tgtccatgga tgccgatggt ggcatgtcca agtactcggg caacaaggca  540
ggtgccaagt acggtaccgg ctactgtgat tctcagtgcc cccgcgacct caagttcatc  600
aacggcgagg ccaacgtaga gaactggcag agctcgacca acgatgccaa cgccggcacg  660
ggcaagtacg gcagctgctg ctccgagatg gacgtctggg aggccaacaa catggccgcc  720
gccttcactc cccaccccttg caccgtgatc ggccagtcgc gctgcgaggg cgactcgtgc  780
ggcggtacct acagcaccga ccgctatgcc ggcatctgcg accccgacgg atgcgacttc  840
aactcgtacc gccagggcaa caagaccttc tacggcaagg gcatgacggt cgacacgacc  900
aagaagatca cggtcgtcac ccagttcctc aagaactcgg ccggcgagct ctccgatc    960
aagcggttct acgtccagaa cggcaaggtc atccccaact ccgagtccac catcccgggc 1020
gtcgagggca actccatcac ccaggactgg tgcgaccgcc agaaggccgc cttcggcgac 1080
gtgaccgact tncaggacaa gggcggcatg gtccagatgg gcaagccct cgcggggccc  1140
atggtcctcg tcatgtccat ctgggacgac cacgccgtca acatgctctg gctcgactcc 1200
acctggccca tcgacggcgc cggcaagccg ggcgccgagc gcggtgcctg ccccaccacc 1260
tcgggcgtcc ccgctgaggt cgaggccgag gcccccaact ccaacgtcat cttctccaac 1320
atccgcttcg gccccatcgg ctccaccgtc tccggcctgc ccgacggcgg cagcggcaac 1380
cccaacccgc ccgtcagctc gtccaccccg gtcccctcct cgtccaccac atcctccggt 1440
tcctccggcc cgactggcgg cacgggtgtc gctaagcact atgagcaatg cggaggaatc 1500
gggttcactg gccctaccca gtgcgagagc ccctacactt gcaccaagct gaatgactgg 1560
tactcgcagt gcctgtaa                                                1578

SEQ ID NO: 26           moltype = AA   length = 525
FEATURE                 Location/Qualifiers
SITE                    364
                        note = MISC_FEATURE - XAA = ANY AMINO ACID
source                  1..525
                        mol_type = protein
                        organism = Myceliophthora thermophilum
SEQUENCE: 26
MYAKFATLAA LVAGAAAQNA CTLTAENHPS LTWSKCTSGG SCTSVQGSIT IDANWRWTHR   60
TDSATNCYEG NKWDTSYCSD GPSCASKCCI DGADYSSTYG ITTSGNSLNL KFVTKGQYST  120
NIGSRTYLME SDTKYQFQLL GNEFTFDVDV SNLGCGLNGA LYFVSMDADG GMSKYSGNKA  180
```

```
GAKYGTGYCD SQCPRDLKFI NGEANVENWQ SSTNDANAGT GKYGSCCSEM DVWEANNMAA  240
AFTPHPCTVI GQSRCEGDSC GGTYSTDRYA GICDPDGCDF NSYRQGNKTF YGKGMTVDTT  300
KKITVVTQFL KNSAGELSEI KRFYVQNGKV IPNSESTIPG VEGNSITQDW CDRQKAAFGD  360
VTDXQDKGGM VQMGKALAGP MVLVMSIWDD HAVNMLWLDS TWPIDGAGKP GAERGACPTT  420
SGVPAEVEAE APNSNVIFSN IRFGPIGSTV SGLPDGGSGN PNPPVSSSTP VPSSSTTSSG  480
SSGPTGGTGV AKHYEQCGGI GFTGPTQCES PYTCTKLNDW YSQCL                  525

SEQ ID NO: 27            moltype = DNA   length = 111
FEATURE                  Location/Qualifiers
source                   1..111
                         mol_type = other DNA
                         organism = Myceliophthora thermophilum
SEQUENCE: 27
gtcgctaagc actatgagca atgcggagga atcgggttca ctggccctac ccagtgcgag  60
agccccctaca cttgcaccaa gctgaatgac tggtactcgc agtgcctgta a           111

SEQ ID NO: 28            moltype = AA   length = 36
FEATURE                  Location/Qualifiers
source                   1..36
                         mol_type = protein
                         organism = Myceliophthora thermophilum
SEQUENCE: 28
VAKHYEQCGG IGFTGPTQCE SPYTCTKLND WYSQCL                            36

SEQ ID NO: 29            moltype = DNA   length = 1676
FEATURE                  Location/Qualifiers
exon                     1..461
sig_peptide              1..17
mat_peptide              52..1673
intron                   462..529
exon                     530..1226
intron                   1227..1289
exon                     1290..1673
source                   1..1676
                         mol_type = genomic DNA
                         organism = Trichoderma reesei
CDS                      1..461
CDS                      530..1226
CDS                      1290..1673
SEQUENCE: 29
atgtatcgga agttggccgt catctcggcc ttcttggcca cagctcgtgc tcagtcggcc  60
tgcactctcc aatcggagac tcacccgcct ctgacatggc agaaatgctc gtctggtggc  120
acgtgcactc aacagacagg ctccgtggtc atcgacgcca actggcgctg gactcacgct  180
acgaacagca gcacgaactg ctacgatggc aacacttgga gctcgaccct atgtcctgac  240
aacgagacct gcgcgaagaa ctgctgtctg gacggtgccg cctacgcgtc cacgtacgga  300
gttaccacga gcggtaacag cctctccatt ggctttgtca cccagtctgc gcagaagaac  360
gttggcgctc gcctttacct tatggcgagc gacacgacct accaggaatt caccctgctt  420
ggcaacgagt tctctttcga tgttgatgtt tcgcagctgc cgtaagtgac ttaccatgaa  480
cccctgacgc tatcttcttg ttggctccca gctgactggc caattcaagg tgcggcttga  540
acggagctct ctacttcgtg tccatggacg cggatggtgg cgtgagcaag tatcccacca  600
acaccgctgg cgccaagtac ggcacggggt actgtgacag ccagtgtccc cgcgatctga  660
agttcatcaa tggccaggcc aacgttgagg ctgggagcc gtcatccaac aacgcgaaca  720
cgggcattgg aggacacgga agctgctgct ctgagatgga tatctgggag gccaactcca  780
tctccgagcc tcttacccccc cacccttgca cgactgtcgg ccaggagatc tgcgagggtg  840
atgggtgcgg cggaacttac tccgataaca gatatgcggc cacttgcgat ccgatggct  900
gcgactggaa cccataccgc ctgggcaaca ccagcttcta cggccctggc tcaagcttta  960
ccctcgatac caccaagaaa ttgaccgttg tcacccagtt cgagacgtcg ggtgccatca  1020
accgatacta tgtccagaat ggcgtcactt ccagcagcc caacgccgag cttggtagtt  1080
actctggcaa cgagctcaac gatgattact gcacagctgg ggaggcagaa ttcggcggat  1140
cctctttctc agacaagggc ggcctgactc agttcaagaa ggctacctct ggcggcatgg  1200
ttctggtcat gagtctgtgg gatgatgtga gtttgatgga caaacatgcg cgttgacaaa  1260
gagtcaagca gctgactgag atgttacagt actacgccaa catgctgtgg ctggactcca  1320
cctacccgac aaacgagacc tcctccacac ccggtgccgt gcgcggaagc tgctccacca  1380
gtccggtgt ccctgctcag gtcgaatctc agtctcccaa cgccaaggtc accttctcca  1440
acatcaagtt cggacccatt ggcagcaccg gcaaccctag cggcggcaac cctcccggca  1500
gaaacccgcc tggcaccacc accacccgcc gcccagccac taccactgga agctctcccg  1560
gacctaccca gtctcactac ggccagtgcg gcggtattgg ctacagcggc cccacggtct  1620
gcgccagcgg cacaacttgc caggtcctga accccttacta ctctcagtgc ctgtaa       1676

SEQ ID NO: 30            moltype = AA   length = 514
FEATURE                  Location/Qualifiers
source                   1..514
                         mol_type = protein
                         organism = Trichoderma reesei
SEQUENCE: 30
MYRKLAVISA FLATARAQSA CTLQSETHPP LTWQKCSSGG TCTQQTGSVV IDANWRWTHA  60
TNSSTNCYDG NTWSSTLCPD NETCAKNCCL DGAAYASTYG VTTSGNSLSI GFVTQSAQKN  120
VGARLYLMAS DTTYQEFTLL GNEFSFDVDV SQLPCGLNGA LYFVSMDADG GVSKYPTNTA  180
GAKYGTGYCD SQCPRDLKFI NGQANVEGWE PSSNNANTGI GGHGSCCSEM DIWEANSISE  240
```

```
ALTPHPCTTV GQEICEGDGC GGTYSDNRYG GTCDPDGCDW NPYRLGNTSF YGPGSSFTLD    300
TTKKLTVVTQ FETSGAINRY YVQNGVTFQQ PNAELGSYSG NELNDDYCTA EEAEFGGSSF    360
SDKGGLTQFK KATSGGMVLV MSLWDDYYAN MLWLDSTYPT NETSSTPGAV RGSCSTSSGV    420
PAQVESQSPN AKVTFSNIKF GPIGSTGNPS GGNPPGGNPP GTTTTRRPAT TTGSSPGPTQ    480
SHYGQCGGIG YSGPTVCASG TTCQVLNPYY SQCL                                514
```

```
SEQ ID NO: 31            moltype = DNA   length = 1545
FEATURE                  Location/Qualifiers
source                   1..1545
                         mol_type = genomic DNA
                         organism = Trichoderma reesei
SEQUENCE: 31
atgtatcgga agttggccgt catctcggcc ttcttggcca cagctcgtgc tcagtcggcc    60
tgcactctcc aatcggagac tcacccgcct ctgacatggc agaaatgctc gtctggtggc   120
acgtgcactc aacagacagg ctccgtggtc atcgacgcca actggcgctg gactcacgct   180
acgaacagca gcacgaactg ctacgatggc aacacttgga gctcgaccct atgtcctgac   240
aacgagacct gcgcgaagaa ctgctgtctg gacggtgccg cctacgcgtc cacgtacgga   300
gttaccacga gcggtaacag cctctccatt ggctttgtca cccagtctgc gcagaagaac   360
gttggcgctc gcctttacct tatggcgagc gacacgacct accaggaatt caccctgctt   420
ggcaacgagt tctctttcga tgttgatgtt tcgcagctgc cgtgcggctt gaacggagct   480
ctctacttcg tgtccatgga cgcggatggt ggcgtgagca agtatcccac caacaccgct   540
ggcgccaagt acggcacggg gtactgtgac agccagtgtc cccgcgatct gaagttcatc   600
aatggccagg ccaacgttga gggctgggag ccgtcatcca acaacgcgaa cacgggcatt   660
ggaggacacg gaagctgctg ctctgagatg gatatctggg aggccaactc catctccgag   720
gctcttaccc cccaccttg cacgactgtc ggccaggaga tctgcgaggg tgatgggtgc   780
ggcggaactt actccgataa cagatatggc ggcacttgca tcccgatgg ctgcgactgg   840
aacccatacc gcctgggcaa caccagcttc tacggccctg gctcaagctt taccctcgat   900
accaccaaga aattgaccgt tgtcacccag ttcgagacgt cgggtgccat caaccgatac   960
tatgtccaga atggcgtcac tttccagcag cccaacgccg agcttggtag ttactctggc   1020
aacgagctca acgatgatta ctgcacagct gaggaggcag aattcggcgg atcctctttc   1080
tcagacaagg gcggcctgac tcagttcaag aaggctacct ctggcggcat ggttctggtc   1140
atgagtctgt gggatgatta ctacgccaac atgctgtggc tggactccac ctacccgaca   1200
aacgagacct cctccacacc cggtgccgtg cgcggaagct gctccaccag ctccggtgtc   1260
cctgctcagg tcgaatctca gtctcccaac gccaaggtca ccttctccaa catcaagttc   1320
ggacccattg gcagcaccgg caaccctagc ggcggcaacc ctcccggcgg aaacccgcct   1380
ggcaccacca ccacccgccg cccagccact accactggaa gctctcccgg acctaccag    1440
tctcactacg gccagtgcgg cggtattggc tacagcggcc ccacggtctg cgccagcggc   1500
acaacttgcc aggtcctgaa cccttactac tctcagtgcc tgtaa                   1545
```

```
SEQ ID NO: 32            moltype = DNA   length = 1545
FEATURE                  Location/Qualifiers
source                   1..1545
                         mol_type = genomic DNA
                         organism = Trichoderma reesei
SEQUENCE: 32
atgtatcgta agctcgcagt catctccgcg ttcctcgcaa cagcacgagc gcagtccgcc    60
tgtaccttgc agtcggaaac acatcctccc ctcacttgcg agaaatgttc gtccggagga   120
acgtgtacgc agcagactgg ctcggtggtc atcgacgcca actggaggtg gacgcatgca   180
accaactcct ccaccaactg ttacgatggc aacacttggt cctccacctt gtgtcccgat   240
aacgaaacct gtgccaagaa ctgttgtttg gatggtgcag cctacgcctc gacatacgga   300
gtcactactt ccggcaactc gctctcgatc ggcttcgtga ctcagtccgc acagaaaaac   360
gtcggagcgc gactctactt gatggcatcc gatacaacct accaggaatt cactctcttg   420
ggcaacgagt tctccttcga cgtcgacgtc tcccagctcc cttgtggcct caacggagca   480
ctctacttcg tgtcgatgga cgcggatgga ggtgtctcca agtacccgac caacacagca   540
ggagcgaaat acggcacggg ttactgtgac tcgcagtgtc ctcgcgatct caagttcatc   600
aacggccagg caaacgtcga aggctgggaa ccctcgtcga caacgccaa caccggcatt   660
ggaggccatg gctcctgttg ttcggaaatg gatatctggg aggccaactc gatctccgag   720
gcactcacac cccacccctg tacaaccgtc ggccaggaga tttgtgaagg agacggctgt   780
ggcggaactt actccgataa ccgttacggt ggtacttgtg atcccgatgg ctgtgactgg   840
aacccctacc gcctcggtaa cacatcgttc tacggtccgg gttcctcctt caccctcgac   900
actaccaaaa agttgaccgg ggtcacgcag ttcgagactt ccggagccat caaccggtac   960
tacgtgcaga acgagtcac attccagcag cccaacgcag aactcggctc gtactcggga   1020
aacgagctca acgatgatta ctgtacagcg gaagaggcag aattcggagg atcgtcgttc   1080
tccgacaagg gtggtttgac ccagttcaag aaggccacat cgggaggaat ggttctggtc   1140
atgtccttgt gggacgacta ctatgccaac atgctctggc tcgactccac ctacccacc    1200
aacgagacct cctcgacacc tggcgcagtg aggggctcgt gttccacttc gtcgggagtg   1260
cctgcacagg tggagtccca gtcgccgaac gccaaggtca ctttctccaa cattaagttc   1320
ggacccatcg gttcgaccgg caacccctcc ggtggaaacc ctcctggcgg aaaccctcct   1380
ggcacaacta caacacgacg gcctgcgact acaacgggtt ctccctggcg accgacccag   1440
tcccactacg gacagtgtgg aggcatcggt tattccggtc cgaccgtctg tgcgtccggc   1500
acaacctgtc aggtcttgaa cccttactat tcgcagtgtc tctaa                   1545
```

```
SEQ ID NO: 33            moltype = DNA   length = 1545
FEATURE                  Location/Qualifiers
sig_peptide              1..51
mat_peptide              52..1542
source                   1..1545
                         mol_type = genomic DNA
                         organism = Trichoderma reesei
```

```
CDS                          1..1542
SEQUENCE: 33
atgtatcgta agctcgcagt catctccgcg ttcctcgcaa cagcacgagc gcagtccgcc   60
tgtaccttgc agtcggaaac acatcctccc ctcacttggc agaaatgttc gtccggagga  120
acgtgtacgc agcagactgg ctcggtggtc atcgacgcca actggaggtg gacgcatgca  180
accaactcct ccaccaactg ttacgatggc aacacttggt cctccacctt gtgtcccgat  240
aacgaaacct gtgccaagaa ctgttgtttg gatggtgcag cctacgcctc gacatacgga  300
gtcactactt ccggcaactc gctctcgatc ggcttcgtga ctcagtccgc acagaaaaac  360
gtcggagcgc gactctactt gatggcatcc gatacaacct accaggaatt cactctcttg  420
ggcaacgagt tctccttcga cgtcgacgtc tcccagctcc cttgtggcct caacggagca  480
ctctacttcg tgtcgatgga cgcggatgga ggtgtctcca agtacccgac caacacagca  540
ggagcgaaat acggcacggg ttactgtgac tcgcagtgtc ctcgcgatct caagttcatc  600
aacggccagg caaacgtcga aggctgggaa ccctcgtcgg ccaacgccgc caccggcatt  660
ggaggccatg gctcctgttg ttcggaaatg gatatctagg aggccaactc gatctccgag  720
gcactcacac cccaccccctg tacaaccgtc ggccaggaga tttgtgaagg agacggctgt  780
ggcggaactt actccgataa ccgttacggt ggtacctgtg atcccgatgg ctgtgactgt  840
aaccccctacc gcctcggtaa cacatcgttc tacggtccgg gttcctcctt caccctcgac  900
actaccaaaa agttgacggt ggtcacgcag ttcgagactt ccggagccat caacggtac  960
tacgtgcaga acggagtcac attccagcag cccaacgcag aactcggctc gtactcggga  1020
aacgagctca acgatgatta ctgtacagcg gaagaggca aattcggagg atcgtcgttc  1080
tccgacaagg tgggtttgac ccagttcaag aaggccacat cgggaggaat ggtgttggtc  1140
atgtccttgt gggacgacta ctatgccaac atgctctggc tcgactccac ctacccacc  1200
aacgagacct cctcgacacc tggcgcagtg aggggctcgt gttccacttc gtcgggagtg  1260
cctgcacagg tggagtccca gtcgccgaac gccaaggtca ctttctccaa cattaagttc  1320
ggacccatcg gttcgaccgg caaccccctcc ggtggaaacc ctcctggcgg aaaccctcct  1380
ggcacaacta caacacgacg gcctgcgact acaacgggtt cgtccctgg accgaccag  1440
tcccactacg gacagtgtgg aggcatcggt tattccggc cgaccgtctg tgcgtccggc  1500
acaacctgtc aggtcttgaa cccttactat tcgcagtgtc tctaa            1545

SEQ ID NO: 34              moltype = AA   length = 514
FEATURE                   Location/Qualifiers
source                    1..514
                          mol_type = protein
                          organism = Trichoderma reesei
SEQUENCE: 34
MYRKLAVISA FLATARAQSA CTLQSETHPP LTWQKCSSGG TCTQQTGSVV IDANWRWTHA   60
TNSSTNCYDG NTWSSTLCPD NETCAKNCCL DGAAYASTYG VTTSGNSLSI GFVTQSAQKN  120
VGARLYLMAS DTTYQEFTLL GNEFSFDVDV SQLPCGLNGA LYFVSMDADG GVSKYPTNTA  180
GAKYGTGYCD SQCPRDLKFI NGQANVEGWE PSSANAATGI GGHGSCCSEM DIWEANSISE  240
ALTPHPCTTV GQEICEGDGC GGTYSDNRYG GTCDPDGCDW NPYRLGNTSF YGPGSSFTLD  300
TTKKLTVVTQ FETSGAINRY YVQNGVTFQQ PNAELGSYSG NELNDDYCTA EEAEFGSSSF  360
SDKGGLTQFK KATSGGMVLV MSLWDDYYAN MLWLDSTYPT NETSSTPGAV RGSCSTSSGV  420
PAQVESQSPN AKVTFSNIKF GPIGSTGNPS GGNPPGGNPP GTTTTRRPAT TTGSSPGPTQ  480
SHYGQCGGIG YSGPTVCASG TTCQVLNPYY SQCL                       514

SEQ ID NO: 35              moltype = DNA   length = 1599
FEATURE                   Location/Qualifiers
sig_peptide               1..26
mat_peptide               79..1596
source                    1..1599
                          mol_type = genomic DNA
                          organism = Aspergillus fumigatus
CDS                       1..1596
SEQUENCE: 35
atgctggcct ccaccttctc ctaccgcatg tacaagaccg cgctcatcct ggccgccctt   60
ctgggctctg gccaggctca gcaggtcggt acttcccagg cggaagtgca tccgtccatg  120
acctggcaga gctgcacggc tggcggcagc tgcaccacca caacggcaa ggtggtcatc  180
gacgcgaact ggcgttgggt gcacaaagtc ggcgactaca ccaactgcta caccggcaac  240
acctgggaca cgactatctg ccctgacgat gcgacctgcg catccaactg cgcccttgag  300
ggtgccaact acgaatccac ctatggtgtg accgccacgg gcaattccct ccgcctcaac  360
ttcgtcacca ccagccagca gaagaacatt ggctcgcgtc tgtacatgat gaaggacgac  420
tcgacctacg agatgtttaa gctgctgaac caggagttca ccttcgatgt cgatgtctcc  480
aacctcccct gcggtctcaa cggtgctctg tactttgtcg ccatggacgc cgacggtggc  540
atgtccaagt acccaaccaa caaggccggt gccaagtacg gtactggata ctgtgactcg  600
cagtgccctc gcgacctcaa gttcatcaac ggtcaggcca acgtcgaagg tggcagccc  660
tcctccaacg atgccaatgc gggtaccggc aaccacgggt cctgctgcgc ggagatggat  720
atctgggagg ccaacagcat ctccacggcc ttcacccccc atccgtgcga cacgcccggc  780
caggtgatgt gcaccggtga tgcctgcggt ggcacctaca gctccgaccg ctacggcggc  840
acctgcgacc ccgacggatg tgatttcaac tccttccgcc agggcaacaa gaccttctac  900
ggccctggca tgaccgtcga caccaagagc aagtttaccg tcgtcaccca gttcatcacc  960
gacgacggca cctccagcgg caccctcaag gagatcaagc gcttctacgt gcagaacggc  1020
aaggtgatcc ccaactcgga gtcgacctgg accggcgtca gcggcaactc catcaccacc  1080
gagtactgca ccgcccagaa gagcctgttc caggaccaga cgtcttcga aaagcacggc  1140
ggcctggagg gcatgggtgc tgccctcgcc cagggtatgg ttctcgtcat gtccctgtgg  1200
gatgatcact cggccaacat gctctggctc gacagcaact acccgaccac tgcctcttcc  1260
accactcccg gcgtcgcccg tggtacctgc gacatctcct ccggcgtccc tgcggatgtc  1320
gaggcgaacc accccgacgc ctacgtcgtc tactccaaca tcaaggtcgg ccccatcggc  1380
tcgaccttca cagcggtgg ctcgaacccc ggtggcggaa ccaccacgac aactaccacc  1440
cagcctacta ccaccacgac cacggctgga aaccctggcg gcaccggagt cgcacagcac  1500
```

```
tatggccagt gtggtggaat cggatggacc ggacccacaa cctgtgccag cccttatacc  1560
tgccagaagc tgaatgatta ttactctcag tgcctgtag                         1599

SEQ ID NO: 36          moltype = AA   length = 532
FEATURE                Location/Qualifiers
source                 1..532
                       mol_type = protein
                       organism = Aspergillus fumigatus
SEQUENCE: 36
MLASTFSYRM YKTALILAAL LGSGQAQQVG TSQAEVHPSM TWQSCTAGGS CTTNNGKVVI   60
DANWRWVHKV GDYTNCYTGN TWDTTICPDD ATCASNCALE GANYESTYGV TASGNSLRLN  120
FVTTSQQKNI GSRLYMMKDD STYEMFKLLN QEFTFDVDVS NLPCGLNGAL YFVAMDADGG  180
MSKYPTNKAG AKYGTGYCDS QCPRDLKFIN GQANVEGWQP SSNDANAGTG NHGSCCAEMD  240
IWEANSISTA FTPHPCDTPG QVMCTGDACG GTYSSDRYGG TCDPDGCDFN SFRQGNKTFY  300
GPGMTVDTKS KFTVVTQFIT DDGTSSGTLK EIKRFYVQNG KVIPNSESTW TGVSGNSITT  360
EYCTAQKSLF QDQNVFEKHG GLEGMGAALA QGMVLVMSLW DDHSANMLWL DSNYPTTASS  420
TTPGVARGTC DISSGVPADV EANHPDAYVV YSNIKVGPIG STFNSGGSNP GGGTTTTTT   480
QPTTTTTTAG NPGGTGVAQH YGQCGGIGWT GPTTCASPYT CQKLNDYYSQ CL          532

SEQ ID NO: 37          moltype = DNA   length = 1374
FEATURE                Location/Qualifiers
sig_peptide            1..17
mat_peptide            52..1371
source                 1..1374
                       mol_type = genomic DNA
                       organism = Thermoascus aurantiacus
CDS                    1..1371
SEQUENCE: 37
atgtatcagc gcgctcttct cttctctttc ttcctctccg ccgcccgcgc gcagcaggcc   60
ggtaccctaa ccgcagagaa tcacccttcc ctgacctggc agcaatgctc cagcggcggt  120
agttgtacca cgcagaatgg aaaagtcgtt atcgatgcga actggcgttg ggtccatacc  180
acctctggat acaccaactg ctacacgggc aatacgtggg acaccagtat ctgtcccgac  240
gacgtgacct cgcctcagaa ttgtgccttg gatggagcgg attacagtgg cacctatggt  300
gttacgacca gtggcaacgc cctgagactg aactttgtca cccaaagctc agggaagaac  360
attggctcgc gcctgtacct gctgcaggac gacaccactt atcagatctt caagctgctg  420
ggtcaggagt ttaccttcga tgtcgacgtc tccaatctcc cttgcgggct gaacggcgcc  480
ctctactttg tggccatgga cgccgacggc ggattgtcca ataccctgg caacaaggca   540
ggcgctaagt atggcactgg ttactgcgac tctcagtgcc ctcgggatct caagttcatc  600
aacggtcagg ccaacgttga aggctggcag ccgtctgcca acgacccaaa tgccggcgtt  660
ggtaaccacg gttcctgctg cgctgagatg gatgtctggg aagccaacag catctctact  720
gcggtgacgc ctcacccatg cgacacccc ggccagacca tgtgccaggg agacgactgt   780
ggtggaacct actcctccac tcgatatgct ggtacctgcg accctgatgg ctgcgacttc  840
aatccttacc gccagggcaa ccactcgttc tacggccccg ggaagatcgt cgacactagc  900
tccaaattca ccgtcgtcac ccagttcatc accgacgacg ggaccccctc cggcaccctg  960
acggagatca aacgcttcta cgtccagaac ggcaaggtga tccccagtc gggagtcgacg  1020
atcagcggcg tcaccggcaa ctcaatcacc accgagtatt gcacggccca gaaggccgcc  1080
ttcggcgaca acaccggctt cttcacgcac ggcgggcttc agaagatcag tcaggctctg  1140
gctcagggca tggtcctcgt catgagcctg tgggacgatc acgccgccaa catgctctgg  1200
ctggacagca cctacccgac tgatgcggac ccggacaccc ctggcgtcgc gcgcggtacc  1260
tgccccacga cctccggcgt cccggccgac gttgagtcgc agaaccccaa ttcatatgtt  1320
atctactcca acatcaaggt cggacccatc aactcgacct tcaccgccaa ctaa        1374

SEQ ID NO: 38          moltype = AA   length = 457
FEATURE                Location/Qualifiers
source                 1..457
                       mol_type = protein
                       organism = Thermoascus aurantiacus
SEQUENCE: 38
MYQRALLFSF FLSAARAQQA GTLTAENHPS LTWQQCSSGG SCTTQNGKVV IDANWRWVHT   60
TSGYTNCYTG NTWDTSICPD DVTCAQNCAL DGADYSGTYG VTTSGNALRL NFVTQSSGKN  120
IGSRLYLLQD DTTYQIFKLL GQEFTFDVDV SNLPCGLNGA LYFVAMDADG GLSKYPGNKA  180
GAKYGTGYCD SQCPRDLKFI NGQANVEGWQ PSANDPNAGV GNHGSCCAEM DVWEANSIST  240
AVTPHPCDTP GQTMCQGDDC GGTYSSTRYA GTCDPDGCDF NPYRQGNHSF YGPGKIVDTS  300
SKFTVVTQFI TDDGTPSGTL TEIKRFYVQN GKVIPQSEST ISGVTGNSIT TEYCTAQKAA  360
FGDNTGFFTH GGLQKISQAL AQGMVLVMSL WDDHAANMLW LDSTYPTDAD PDTPGVARGT  420
CPTTSGVPAD VESQNPNSYV IYSNIKVGPI NSTFTAN                           457

SEQ ID NO: 39          moltype = DNA   length = 1428
FEATURE                Location/Qualifiers
exon                   1..603
sig_peptide            1..18
mat_peptide            55..1425
intron                 604..663
exon                   664..1425
source                 1..1428
                       mol_type = genomic DNA
                       organism = Penicillium emersonii
CDS                    1..603
CDS                    664..1425
```

```
SEQUENCE: 39
atgcttcgac gggctcttct tctatcctct tccgccatcc ttgctgtcaa ggcacagcag   60
gccggcacgg cgacggcaga gaaccacccg cccctgacat ggcaggaatg caccgcccct   120
gggagctgca ccacccagaa cggggcggtc gttcttgatg cgaactggcg ttgggtgcac   180
gatgtgaacg gatacaccaa ctgctacacg ggcaatacct ggaaccccac gtactgccct   240
gacgacgaaa cctgcgccca gaactgtgcg ctggacggcg cggattacga gggcacctac   300
ggcgtgactt cgtcgggcag ctccttgaag ctcaatttcg tcaccgggtc gaacgtcgga   360
tcccgtctct acctgctgca ggacgactcg acctatcaga tcttcaagct tctgaaccgc   420
gagtttacct ttgacgtcga tgtctccaat cttccgtgcg gattgaacgg cgctctgtac   480
tttgtcgcca tggacgccga cggcggcgtg tccaagtacc cgaacaacaa ggctggtgcc   540
aagtacggaa ccgggtattg cgactcccaa tgcccacggg acctcaagtt catcgacggc   600
gaggtatgtc cagtggtaaa atcgatcgtc tcgtgaactt ctgctgacag gttcgatcta   660
caggccaacg tcgagggctg gcagccgtct tcgaacaacg ccaacaccgg aattggcgac   720
catggctcct gctgtgcgga gatggatgtc tgggaagcca acagcatctc caatgcggtc   780
actccgcacc cgtgcgacac gccaggccag acgatgtgct ctggcgatga ctgcggtggc   840
acatactcta acgatcgcta cgcgggaacc tgcgatcctg acggctgtga cttcaaccct   900
taccgcatgg gcaacacttc tttctacggg cctggcaaga tcatcgatac caccaagcct   960
ttcactgtcg tgacgcagtt cctcactgat gatggtacgg atactggaac tctcagcgag   1020
atcaagcgct tctacgtcca gaacggcaac gtcattccgc agcccaactc ggacatcagt   1080
ggcgtgaccg gcaactcgat cacgacggag ttctgtactg ctcagaagca ggcctttggc   1140
gacacgacg acttctctca gcacggtggc ctggccaaga tgggagcggc catgcagcag   1200
ggtatggtcc tggtgatgag tttgtgggac gactacgccg cacagatgct tggctggat   1260
tccgactacc cgacggatgc ggaccccacg accctggta ttgcccgtgg aacgtgtccg   1320
acggactcgg gcgtcccatc ggatgtcgag tcgcagagcc ccaactccta cgtgacctac   1380
tcgaacatca agtttggtcc gatcaactcg accttcaccg cttcgtga   1428

SEQ ID NO: 40          moltype = AA  length = 455
FEATURE                Location/Qualifiers
source                 1..455
                       mol_type = protein
                       organism = Penicillium emersonii
SEQUENCE: 40
MLRRALLLSS SAILAVKAQQ AGTATAENHP PLTWQECTAP GSCTTQNGAV VLDANWRWVH   60
DVNGYTNCYT GNTWNPTYCP DDETCAQNCA LDGADYEGTY GVTSSGSSLK LNFVTGSNVG   120
SRLYLLQDDS TYQIFKLLNR EFTFDVDVSN LPCGLNGALY FVAMDADGGV SKYPNNKAGA   180
KYGTGYCDSQ CPRDLKFIDG EANVEGWQPS SNNANTGIGD HGSCCAEMDV WEANSISNAV   240
TPHPCDTPGQ TMCSGDDCGG TYSNDRYAGT CDPDGCDFNP YRMGNTSFYG PGKIIDTTKP   300
FTVVTQFLTD DGTDTGTLSE IKRFYVQNGN VIPQPNSDIS GVTGNSITTE FCTAQKQAFG   360
DTDDFSQHGG LAKMGAAMQQ GMVLVMSLWD DYAAQMLWLD SDYPTDADPT TPGIARGTCP   420
TDSGVPSDVE SQSPNSYVTY SNIKFGPINS TFTAS                             455

SEQ ID NO: 41          moltype = DNA  length = 1599
FEATURE                Location/Qualifiers
sig_peptide            1..25
mat_peptide            76..1596
source                 1..1599
                       mol_type = genomic DNA
                       organism = Talaromyces leycettanus
CDS                    1..1596
SEQUENCE: 41
atggccagcc tcttctcttt caagatgtac aaggccgctc tggtcctctc ctctctcctt   60
gcggccaccc aggcccagca ggccggcacc ctgaccaccg aaacccatcc ttctctgacc   120
tggcagcaat gctctgccgg cggcagctgc accactcaga acggcaaggt cgtcatcgac   180
gccaactggc gctgggttca cagcaccagc ggctcgaaca actgctacac tggcaacact   240
tgggatgcta ctctctgccc tgacgacgtg acttgcgctg ccaactgcgc cctggacgtgc   300
gctgactact cgggcaccta cggtgtcacc accagcggca actctctgcg cctgaacttc   360
gtcacccagg cgtcgcagaa gaacgtcggc tctcgtctct atctgatgga gaatgacaca   420
acctaccaga tcttcaagtt gctgaaccag gagttcacct ttgacgttga tgtctccaac   480
cttccctgcg gtctcaacgg tgctctctac ctggttgcca tggatgccga cggcggcatg   540
gccaagtacc caaccaacaa ggctggtgcg aagtacggac ccggttactg cgactcccag   600
tgccctcgcg acctgaagtt catcaacggt gaggccaatg ttgagggatg gcagccttct   660
tccaatgacc ccaactctgg cattggcaac acggctctt gctgtgctga gatggacatc   720
tgggaggcca acagcatctc caatgcagtc actcctcacc cttgcgacac cccgggcag   780
gtcatgtgca ccggcaacaa ctgtggtggc acttacagga acttcagcca gcacggcggt   840
tgcgatcctg atggctgcga cttcaacccc taccgcatgg gcaaccactc cttctacggg   900
cccaaacaga tcgtcgacac cagctccaag ttcactgttg ttactcagtt cctcaccgat   960
gatggcacct ccaccggcac cctcagcgag atcaggcgct ctacgttca gaacggccag   1020
gtcatcccca actccgtgtc cacgatcagc ggcgtctccg gcaactccat caccaccgag   1080
ttctgcacgg cccagaagca ggctttcggc gacactggca acttcagcaa gacacggcgt   1140
ctgtctggca tgtccgccgc cctctcccag ggtatggttc tcgtcatgag cttgtgggac   1200
gaccacgccg ccaacatgct ctggcttgac agcacctacc cgaccaacgc cacctcttcc   1260
accccggtg ccgccgtgg tacttgcgac atctcctccg gtgtcccgc cgatgttgag   1320
tccaacgacc ccaacgccta cgtcgtctac tccaacatca aggtcggccc gatcggctct   1380
accttcagca gctctggctc tggctctagc tccagctcca gcaccaacac caccaccagc   1440
gcttccccaa ccacgaccac ctccagcgct tccagcaccg gcactggcgt tgctcagcac   1500
tggggtcagt gcggtggcca gggatggacc ggtccgacca cctgcgttag ccctacacc   1560
tgccaggagc tgaaccccta ctactaccag tgcctgtaa                         1599

SEQ ID NO: 42          moltype = AA  length = 532
```

-continued

```
FEATURE                 Location/Qualifiers
source                  1..532
                        mol_type = protein
                        organism = Talaromyces leycettanus
SEQUENCE: 42
MASLFSFKMY KAALVLSSLL AATQAQQAGT LTTETHPSLT WQQCSAGGSC TTQNGKVVID  60
ANWRWVHSTS GSNNCYTGNT WDATLCPDDV TCAANCALDG ADYSGTYGVT TSGNSLRLNF  120
VTQASQKNVG SRLYLMENDT TYQIFKLLNQ EFTFDVDVSN LPCGLNGALY LVAMDADGGM  180
AKYPTNKAGA KYGTGYCDSQ CPRDLKFING EANVEGWQPS SNDPNSGIGN HGSCCAEMDI  240
WEANSISNAV TPHPCDTPGQ VMCTGNNCGG TYSTTRYAGT CDPDGCDFNP YRMGNHSFYG  300
PKQIVDTSSK FTVVTQFLTD DGTSTGTLSE IRRFYVQNGQ VIPNSVSTIS GVSGNSITTE  360
FCTAQKQAFG DTDDFSKHGG LSGMSAALSQ GMVLVMSLWD DHAANMLWLD STYPTNATSS  420
TPGAARGTCD ISSGVPADVE SNDPNAYVVY SNIKVGPIGS TFSSSGSGSS SSSSTTTTTT  480
ASPTTTTSSA SSTGTGVAQH WGQCGGQGWT GPTTCVSPYT CQELNPYYYQ CL          532

SEQ ID NO: 43           moltype = DNA   length = 1599
FEATURE                 Location/Qualifiers
sig_peptide             1..25
mat_peptide             76..1596
source                  1..1599
                        mol_type = genomic DNA
                        organism = Talaromyces leycettanus
CDS                     1..1596
SEQUENCE: 43
atggcgtcct ctctctctta caggatctac aagaatgctc tcatcttctc ttctctcctg  60
gccgctgccc agggtcagca gattggtacc taccagacgg agacccatcc gcctctgacc  120
tggcagacat gcaccagcgg cggcagttgc acgaccaacc aaggctccat cgtcctcgat  180
gccaactggc gctgggtgca cgaggtcggc agcaccacca actgctacac cggcaatacc  240
tgggacacct ccatctgcag cacggatacg acctgcgctc agcaatgtgc cgtcgatggt  300
gccgactacg agggcaccta tggtatcacg accagcggca gccaggtccg catcaacttc  360
gtcaccaaca actcgaacgg aaagaacgtc ggcgcgcgtg tctacatgat ggcggacaac  420
acccactacc aaatttacca gctgctgaac caggagttca cctttgatgt cgacgtgtcc  480
aacctgcctt gcgggcctcaa cggtgccctc tactttgtgg tcatggacgc cgatggtggt  540
gtctccaagt atcccaacaa caaggctggt gcccagtacg gtgtcggtta ctgcgactcc  600
cagtgtccca gagacctcaa attcatccag ggacaggcca acgtcgaggg ctggcaaccg  660
tcgtccaaca acgccaatac cggcctgggc aaccacggct cctgctgtgc tgaactggac  720
gtctgggagt cgaacagcat ctcccaggcc ctcactcccc accctgcga cactcccacc  780
aatacccgt gcaccggtga tagctgcggt ggcacataca gcagcaaccg ttatgcgggc  840
acttgcgatc ctgacggctg cgatttcaac ccctaccgct tgggcaacac caccttctac  900
ggtcctggca agactattga caccaccaaa cccttcacgg ttgtgacgca gttcatcacg  960
gatgacggca cttccagcgg cacccctgtcc gaaattaggc gtttctatgt ccagaacggt  1020
gttacgtacg cccagcccaa ctctgacgtc agcggtatca gcggcaatgc catcaacagt  1080
gcttactgca ctgcggagaa caccgtcttc aacggtgccg gaccttcgc gacgacggc  1140
ggcctggctg gcatgagcca ggccatgtcc accggtatgg tcttggtgat gagcctgtgg  1200
gatgattact atgccgacat gctctggctc gacagcacct acccaaccaa cgacaccgca  1260
agcacgcccg gtgcggtccg tggaacctgc tctacgtcgt ccggtgtccc cagccaggtc  1320
gaatccgcca gcccgaacgc ctacgtgacc tactcgaaca tcaaggttgg tcccattggc  1380
tcgactttca actctggcgg ctctggctct ggcagcagct ccagcactac cacgaccact  1440
cacgccagca ccacgacgac gtcctccgcc tcgtctacgg gaactggcgt ggcccaacac  1500
tggggccagt gtggtggaca gggctggacc ggcccaacaa cctgcgtttc cccgtacact  1560
tgccaggagc tgaacccgta ctactaccag tgtctgtag                          1599

SEQ ID NO: 44           moltype = AA   length = 532
FEATURE                 Location/Qualifiers
source                  1..532
                        mol_type = protein
                        organism = Talaromyces leycettanus
SEQUENCE: 44
MASSLSYRIY KNALIFSSLL AAAQGQQIGT YQTETHPPLT WQTCTSGGSC TTNQGSIVLD  60
ANWRWVHEVG STTNCYTGNT WDTSICSTDT TCAQQCAVDG ADYEGTYGIT TSGSQVRINF  120
VTNNSNGKNV GARVYMMADN THYQIYQLLN QEFTFDVDVS NLPCGLNGAL YFVVMDADGG  180
VSKYPNNKAG AQYGVGYCDS QCPRDLKFIQ GQANVEGWQP SSNNANTGLG NHGSCCAELD  240
VWESNSISQA LTPHPCDTPT NTLCTGDSCG GTYSSNRYQS TCDPDGCDFN PYRLGNTTFY  300
GPGKTIDTTK PFTVVTQFIT DDGTSSGTLS EIRRFYVQNG VTYAQPNSDV SGISGNAINS  360
AYCTAENTVF NGAGTFAQHG GLAGMSQAMS TGMVLVMSLW DDYYADMLWL DSTYPTNDTA  420
STPGAVRGTC STSSGVPSQV ESASPNAYVT YSNIKVGPIG STFNSGGSGS GSSSSTTTTT  480
HASTTTTSSA SSTGTGVAQH WGQCGGQGWT GPTTCVSPYT CQELNPYYYQ CL          532

SEQ ID NO: 45           moltype = DNA   length = 1507
FEATURE                 Location/Qualifiers
exon                    1..603
sig_peptide             1..18
mat_peptide             55..1504
intron                  604..667
exon                    668..1235
intron                  1236..1310
exon                    1311..1504
source                  1..1507
                        mol_type = genomic DNA
```

```
                           organism = Talaromyces byssochlamydoides
CDS                        1..603
CDS                        668..1235
CDS                        1311..1504
SEQUENCE: 45
atgtttcgac gggctctttt cctgtcctct tccgccttcc ttgctgtcaa agcccagcag   60
atcggcacgg tcagtccgga gaaccatccg cccctggcat gggagcagtg cactgcccct  120
gggagttgca cgactgtgaa tggtgcggtc gtccttgatg cgaactggcg ttgggtccac  180
aatgttgggg gatacaccaa ctgctacact ggcaatacct gggacaccac gtactgccct  240
gacgacgtga cctgcgcaga gaattgtgcg ctggatggcg cagattacga gggcgacctac  300
ggcgtgacca cctcgggcag ctccctgaag ctcgatttcg tcaccgggtc taacgtcgga  360
tctcgtctct acctgttgga gaatgattcg acctatcaga tcttcaagct tctgaaccag  420
gaattcacct ttgacgtcga cgtttccaat cttccgtgcg gattaaacgg cgctctgtac  480
cttgttacca tggctgctga cggcggggtg tctcagtacc cgaataacaa ggccggccgca  540
gcgtatggaa ccggttattg cgattcccag tgtccaaggg acttgaagtt tatcgatggc  600
caggtatgta gagctgtaat cacccatgtt gtgaaatcac tctcctactg acatggtcga  660
tttataggcc aacgttgagg gctggcagcc gtcttcgaac aacgccaata caggtattgg  720
caaccatggc tcctgctgtg cggagatgga tatctgggaa gccaacagca tctccaatgc  780
ggtgactccg cacccatgcg acacacccgg ccagacaatg tgcgagggga acgactgtgg  840
tggcacgtat tccaccaatc gctatgcagg cacctgcgat cctgacggct gcgacttcaa  900
cccctaccgc atgggcaacc attctttcta cggccctggg gagattgtcg atactaccca  960
gccttcact gtcgtgacac agttccttac cgatgatggc acggatactg gcactctcag 1020
cgagatcaaa cgcttctacg tccaaaacgg gaaagtcatt cctcagccga actccgacat 1080
tgccggcgtg actggcaact cgatcaccag cgagttttgc gatgcccaga agacggcttt 1140
cggcgacatt aacaactttg atacacacgg cggtctggcc agtatgggag ctgcgctgca 1200
gcaggtatg gttctggtga tgagtctgtg ggacggtagg tccttgggag acaccggac 1260
gttctatatc aaccagaact gccagaactg acgaattaaa acacttttag attacgcggc 1320
aaacatgctg tggttggaca gcatttatcc aacaaatgca tctgctagca ctcctggtgc 1380
tgctcgtgga acctgttcga cgagctccgg tgtcccatcg caagtcgagt cgcagagccc 1440
caacgcctac gtgacgtact ccaacattaa agttggacca atcaactcga ccttcaccac 1500
ttcgtaa                                                           1507

SEQ ID NO: 46              moltype = AA   length = 455
FEATURE                    Location/Qualifiers
source                     1..455
                           mol_type = protein
                           organism = Talaromyces byssochlamydoides
SEQUENCE: 46
MFRRALFLSS SAFLAVKAQQ IGTVSPENHP PLAWEQCTAP GSCTTVNGAV VLDANWRWVH   60
NVGGYTNCYT GNTWDTTYCP DDVTCAENCA LDGADYEGTY GVTTSGSSLK LDFVTGSNVG  120
SRLYLLENDS TYQIFKLLNQ EFTFDVDVSN LPCGLNGALY LVTMAADGGV SQYPNNKAGA  180
AYGTGYCDSQ CPRDLKFIDG QANVEGWQPS SNNANTGIGN HGSCCAEMDI WEANSISNAV  240
TPHPCDTPGQ TMCEGNDCGG TYSTNRYAGT CDPDGCDFNP YRMGNHSFYG PGEIVDTTQP  300
FTVVTQFLTD DGTDTGTLSE IKRFYVQNGK VIPQPNSDIA GVTGNSITSE FCDAQKTAFG  360
DINNFDTHGG LASMGAALQQ GMVLVMSLWD DYAANMLWLD SIYPTNASAS TPGAARGTCS  420
TSSGVPSQVE SQSPNAYVTY SNIKVGPINS TFTTS                             455

SEQ ID NO: 47              moltype = DNA   length = 1353
FEATURE                    Location/Qualifiers
sig_peptide                1..20
mat_peptide                61..1350
source                     1..1353
                           mol_type = genomic DNA
                           organism = Myceliophthora thermophila
CDS                        1..1350
SEQUENCE: 47
atgaagcagt acctccagta cctcgcggcg accctgcccc tggtgggcct ggccacggcc   60
cagcaggcgg gtaacctgca gaccgagact caccccaggc tcacttggtc caagtgcacg  120
gccccgggat cctgccaaca ggtcaacggc gaggtcgtca tcgactccaa ctggcgctgg  180
gtgcacgacg agaacgcgca gaactgctac gacggcaacc agtggaccaa cgcttgcacc  240
tctgccaccg actgcgccga gaattgcgcg ctcgagggtg ccgactacca gggcacctat  300
ggcgcctcga ccagcggcaa tgccctgacg ctcaccttcg tcactaagca cgagtacggc  360
accaacattg gctcgcgcct ctacctcatg aacgcgcga acaagtacca gatgttcacc  420
ctcaagggca acgagctggc cttcgacgtc gacctctcga ccgtcgagtg cggcctcaac  480
agcgccctct acttcgtggc catggaggag gatggcggtg tgtcgagcta cccgaccaac  540
acggccggtg ctaagttcgg cactgggtac tgcgacgccc aatgcgcacg cgacctcaag  600
ttcgtcggcg gcaagggcaa catcgagggc tggaagccgt ccaccaacga tgccaatgcc  660
ggtgtcggtc cttatggcgg gtgctgcgct gagatcgacg tctgggagtc gaacaagtat  720
gctttcgctt tcaccccgca cggttgcgag aaccctaaat accacgtctg cgagaccaac  780
aactgcggtg gcacctactc cgaggaccgc ttcgctggtg actgcgatgc caacggctgc  840
gactacaacc cctaccgcat gggcaaccag gacttctacg tcccggctt gacggtcgat  900
accagcaaga agttcaccgt cgtcagccag ttcgaggaga caagctcac ccagttcttc  960
gtccaggacg gcaagaagat tgagatcccc ggccccaagg tcgagggcat cgatgcggac 1020
agcgccgtca tcaccctga gctgtgcagt gccctgttca aggccttcga tgaccgtgac 1080
cgcttctcgg aggttggcgg cttcgatgcc atcaacacgg ccctcagcac tccatggtc 1140
ctcgtcatgt ccatctggga tgatcactac gccaatatgc tctggctcga ctcgagctac 1200
cccctgaga aggctggcca gcctggcggt gaccgtggcc cgtgtcctca ggactctggc 1260
gtcccggcg acgttgaggc tcagtaccct aatgccaagg tcatctggtc caacatccgc 1320
ttcggcccca tcggctcgac tgtcaacgtc taa                              1353
```

```
SEQ ID NO: 48            moltype = AA   length = 450
FEATURE                  Location/Qualifiers
source                   1..450
                         mol_type = protein
                         organism = Myceliophthora thermophila
SEQUENCE: 48
MKQYLQYLAA TLPLVGLATA QQAGNLQTET HPRLTWSKCT APGSCQQVNG EVVIDSNWRW   60
VHDENAQNCY DGNQWTNACS SATDCAENCA LEGADYQGTY GASTSGNALT LTFVTKHEYG  120
TNIGSRLYLM NGANKYQMFT LKGNELAFDV DLSAVECGLN SALYFVAMEE DGGVSSYPTN  180
TAGAKFGTGY CDAQCARDLK FVGGKGNIEG WKPSTNDANA GVGPYGGCCA EIDVWESNKY  240
AFAFTPHGCE NPKYHVCETT NCGGTYSEDR FAGDCDANGC DYNPYRMGNQ DFYGPGLTVD  300
TSKKFTVVSQ FEENKLTQFF VQDGKKIEIP GPKVEGIDAD SAAITPELCS ALFKAFDDRD  360
RFSEVGGFDA INTALSTPMV LVMSIWDDHY ANMLWLDSSY PPEKAGQPGG DRGPCPQDSG  420
VPADVEAQYP NAKVIWSNIR FGPIGSTVNV                                   450

SEQ ID NO: 49            moltype = DNA   length = 1590
FEATURE                  Location/Qualifiers
sig_peptide              1..18
mat_peptide              55..1587
source                   1..1590
                         mol_type = genomic DNA
                         organism = Chaetomium thermophilum
CDS                      1..1587
SEQUENCE: 49
atgatgtaca agaagttcgc cgctctcgcc gccctcgtgg ctggcgccgc cgcccagcag   60
gcttgctccc tcaccactga gacccacccc agactcactt ggaagcgctg cacctctggc  120
ggcaactgct cgaccgtgaa cggcgccgtc accatcgatg ccaactggcg ctggactcac  180
accgtttccg gctcgaccaa ctgctacacc ggcaacgagt gggatacctc catctgctct  240
gatggcaaga gctgcgccca gacctgctgc gtcgacgacg ctgactactc ttcgacctat  300
ggtatcacca ccagcggtga ctccctgaac ctcaagttcg tcaccaagca ccagtacggc  360
accaatgtcg gctctcgtgt ctacctgatg gagaacgaca ccaagtacca gatgttcgag  420
ctcctcggca acgagttcac cttcgatgtc gatgtctcta acctgggctg cggtctcaac  480
ggtgccctct acttcgtctc catggacgct gatggtggta tgagcaagta ctctggcaac  540
aaggctggcg ccaagtacgg taccggctac tgcgatgctc agtgcccgcg cgaccttaag  600
ttcatcaacg gcgaggccaa cattgagaac tggaccccct cgaccaatga tgccaacgcc  660
ggtttcggcc gctatggcag ctgctgctct gagatggata tctgggaggc caacaacatg  720
gctactgcct tcactcctca cccttgcacc attatcggcc agagccgctg cgagggcaac  780
agctgcggtg gcacctacag ctctgagcgc tatgctggtg tttgcgatcc tgatggctgc  840
gacttcaacg cctaccgcca gggcgacaag accttctacg gcaagggcat gaccgtcgac  900
accaccaaga agatgaccgt cgtcacccag ttccacaaga actcggctgg cgtcctcagc  960
gagatcaagc gcttctacgt tcaggacggc aagatcattg ccaacgccga gtccaagatc 1020
cccggcaacc ccggcaactc catcacccag gagtggtgac atgcccagaa ggtcgccttc 1080
ggtgacatcg atgacttcaa ccgcaagggc ggtatggctc agatgagcaa ggccctgcag 1140
ggccctatgg tcctggtcat gtccgtctgg gatgaccact acgccaacat gctctggctc 1200
gactcgacct accccatcga caaggccggc acccccggcg ccgagcgcgg tgcttgcccg 1260
accacctccg gtgtccctgc cgagattgag gcccaggtcc ccaacagcaa cgtcatcttc 1320
tccaacatcc gcttcggccc catcggctcg accgtccctg gcctcgacgg cagcactccc 1380
agcaacccga ccgccaccgt tgctcctccc acttctacca ccagcgtgag aagcagcact 1440
actcagattt ccacccgac tagccagccc ggcggctgca ccacccagaa gtggggccag 1500
tgcggtggta tcggctacac cggctgcact aactgcgttg ctggcactac ctgcactgag 1560
ctcaacccct ggtacagcca gtgcctgtaa                                  1590

SEQ ID NO: 50            moltype = AA   length = 529
FEATURE                  Location/Qualifiers
source                   1..529
                         mol_type = protein
                         organism = Chaetomium thermophilum
SEQUENCE: 50
MMYKKFAALA ALVAGAAAQQ ACSLTTETHP RLTWKRCTSG GNCSTVNGAV TIDANWRWTH   60
TVSGSTNCYT GNEWDTSICS DGKSCAQTCC VDGADYSSTY GITTSGDSLN LKFVTKHQYG  120
TNVGSRVYLM ENDTKYQMFE LLGNEFTFDV DVSNLGCGLN GALYFVSMDA DGGMSKYSGN  180
KAGAKYGTGY CDAQCPRDLK FINGEANIEN WTPSTNDANA GFGRYGSCCS EMDIWEANNM  240
ATAFTPHPCT IIGQSRCEGN SCGGTYSSER YAGVCDPDGC DFNAYRQGDK TFYGKGMTVD  300
TTKKMTVVTQ FHKNSAGVLS EIKRFYVQDG KIIANAESKI PGNPGNSITQ EWCDAQKVAF  360
GDIDDFNRKG GMAQMSKALE GPMVLVMSVW DDHYANMLWL DSTYPIDKAG TPGAERGACP  420
TTSGVPAEIE AQVPNSNVIF SNIRFGPIGS TVPGLDGSTP SNPTATVAPP TSTTSVRSST  480
TQISTPTSQP GGCTTQKWGQ CGGIGYTGCT NCVAGTTCTE LNPWYSQCL               529

SEQ ID NO: 51            moltype = DNA   length = 21
FEATURE                  Location/Qualifiers
misc_feature             1..21
                         note = Synthetic Construct DNA Primer
source                   1..21
                         mol_type = other DNA
                         organism = Synthetic Construct
SEQUENCE: 51
cccttgtcga tgcgatgtat c                                             21
```

```
SEQ ID NO: 52          moltype = DNA   length = 21
FEATURE                Location/Qualifiers
misc_feature           1..21
                       note = Synthetic Construct DNA Primer
source                 1..21
                       mol_type = other DNA
                       organism = Synthetic Construct
SEQUENCE: 52
atcctcaatt ccgtcggtcg a                                                    21

SEQ ID NO: 53          moltype = DNA   length = 1570
FEATURE                Location/Qualifiers
source                 1..1570
                       mol_type = genomic DNA
                       organism = Rasamsonia emersonii
SEQUENCE: 53
gaatcgatgc tcaattcggg atggagatgt cgatcagatg gagtataaaa gggcagggtg   60
aatccagggt ccaggccatc tgccatcact cagactcaaa cactccatca gcagcttcga  120
aagcggtctt tttgctatca tcatgcttcg acgggctctt cttctatcct cttccgccat  180
ccttgctgtc aaggcacagc aggccggcac ggcgacggca gagaaccacc cgcccctgac  240
atggcaggaa tgcaccgccc ctgggagctg caccacccag aacggggcgg tcgttcttga  300
tgcgaactgg cgttgggtgc acgatgtgaa cggatacacc aactgctaca gggcaaatac  360
ctggaacccc acgtactgcc ctgacgacga aacctgcgcc cagaactgtg cgctggacgg  420
cgcggattac gagggcacct acggcgtgac ttcgtcgggc agctccttga agctcaattt  480
cgtcaccggg tcgaacgtcg gatcccgtct ctacctgctg caggacgact cgacctatca  540
gatcttcaag cttctgaacc gcgagtttac ctttgacgtc gatgtctcca atcttccgtg  600
cggattgaac ggcgctctgt actttgtcgc catggacgcc gacggcggcg tgtccaagta  660
cccgaacaac aaggctggtg ccaagtacgg aaccgggtat tgcgactccc aatgcccacg  720
ggacctcaag ttcatcgacg gcgaggtatg tccagtggta aaatcgatcg tctcgtgaac  780
ttctgctgac aggttcgatc tacaggccaa cgtcgagggc ggcagccgt cttcgaacaa  840
cgccaacacc ggaattggcg accatggctc ctgctgtgcg gagatggatg tctgggaagc  900
caacagcatc tccaatgcgg tcactccgca cccgtgcgac acgccaggcc agacgatgtg  960
ctctggcgat gactgcggtg gcacatactc taacgatcgc tacgcgggaa cctgcgatcc 1020
tgacggctgt gacttcaacc cttaccgcat gggcaacact tctttctacg ggcctggcaa 1080
gatcatcgat accaccaagc ctttcactgt cgtgacgcag ttcctcactg atgatggtac 1140
ggatactgga actctcagcg agatcaagcg cttctacgtc cagaacggca acgtcattcc 1200
gcagcccaac tcggacatca gtggcgtgac cggcaactcg atcacgacgg agttctgtac 1260
tgctcagaag caggcctttg cgacacgga cgacttctct cagcacggtg gcctggccaa 1320
gatgggagcg gccatgcagc agggtatggt cctggtgatg agtttgtggg acgactacgc 1380
cgcgcagatg ctgtgctgg attccgacta cccgacggat gcggacccca cgaccctgg 1440
tattgcccgt ggaacgtgtc cgacggactc gggcgtccca tcggatgtcg agtcgcgag 1500
ccccaactcc tacgtgacct actcgaacat caagtttggt ccgatcaact cgaccttcac 1560
cgcttcgtga                                                         1570

SEQ ID NO: 54          moltype = DNA   length = 1368
FEATURE                Location/Qualifiers
source                 1..1368
                       mol_type = genomic DNA
                       organism = Rasamsonia emersonii
SEQUENCE: 54
atgttgcgaa gggccttgtt gctctcgtcc tccgcaatct tggcggtcaa ggcacagcag   60
gcaggcaccg caaccgcaga gaaccatcct ccgctcactt ggcaggaatg tacagcacct  120
ggctcctgta caacccagaa cggagcggtc gtgctcgatg cgaactggcg ctgggtgcac  180
gatgtcaacg gatacacaaa ctgttataca ggtaacacgt ggaaccctac gtattgtccc  240
gacgacgaaa cgtgtgccca gaactgtgcg ttggatggag gactacga gggaacgtat  300
ggcgtgacct cgtccggctc ctccttgaag ctcaacttcg tcacgggctc gaacgtcggc  360
tcccgcttgt acctcctcca ggacgactcg acctaccaga tcttcaagct cctcaacagg  420
gagttcacct cgacgtcga tgtctccaac ttgccctgtg gtctcaacgg agccttgtac  480
ttcgtcgcga tggatgacaga cggaggtgtc tcgaagtacc ccaacaacaa ggcaggtgcc  540
aagtatggta ctggctactg tgattcgcag tgtcctcgcg atctcaagtt cattgacggt  600
gaggcgaacg tggaaggatg gcagccctcg tccaacaacg cgaacactgg catcggtgat  660
cacggttcgt gttgtgccga gatggacgtc tgggaagcca actccatctc gaacgcggtc  720
acaccgcacc cgtgtgatac tcctggccag actatgtgtt ccggagatga ttgtggaggc  780
acctattcga acgaccggta tgcaggcacg tgtgacccga cttgtcaacg cttcaaccg  840
taccgcatgg gcaacacctc cttctatgga ccgggtaaga tcatcgatac aactaagccc  900
ttcaccgtcg tcacgcagtt cctcacagat gacggcacgg acacaggtac tttgtcggag  960
atcaaacgct tctacgtcca gaacggaaac gtcatccccc agccgaactc cgacatttcg 1020
ggagtcacag gcaactcgat tacgaccgag ttctgtacag cccagaaaca ggcattcggt 1080
gacacggatg atttctccca gcacgagga ttggcgaaaa tgggagccgc aatgcagcag 1140
ggaatggtcc tcgtgatgtc gctctggac gactatgcag cccagatgtt gtggctcgac 1200
tcggactacc ccagacgc cgatcccacg acacccggta tcgcacgagg cacttgtccg 1260
acagattccg gagtcccgtc ggacgtcgag tcccagtccc ccaactcgta cgtcacctat 1320
tcgaacatca aattcggtcc catcaactcg acattcacag cctcgtaa                1368

SEQ ID NO: 55          moltype = DNA   length = 1560
FEATURE                Location/Qualifiers
source                 1..1560
                       mol_type = genomic DNA
                       organism = Rasamsonia emersonii
```

```
SEQUENCE: 55
atgttgcgaa gggccttgtt gctctcgtcc tccgcaatct tggcggtcaa ggcacagcag   60
gcaggcaccg caaccgcaga gaaccatcct ccgctcactt ggcaggaatg tacagcacct  120
ggctcctgta caacccagaa cggagcggtc gtgctcgatg cgaactggcg ctgggtgcac  180
gatgtcaacg gatacacaaa ctgttataca ggtaacacgt ggaaccctac gtattgtccc  240
gacgacgaaa cgtgtgccca gaactgtgcg ttggatggag cagactacga gggaacgtat  300
ggcgtgacct cgtccggctc ctccttgaag ctcaacttcg tcacgggctc gaacgtcggc  360
tcccgcttgt acctcctcca ggacgactcg acctaccaga tcttcaagct cctcaacagg  420
gagttcacct tcgacgtcga tgtctccaac ttgccctgtg gtctcaacgg agccttgtac  480
ttcgtcgcga tggatgcaga cggaggtgtc tcgaagtacc ccaacaacaa ggcaggtcgc  540
aagtatggta ctggctactg tgattcgcag tgtcctcgcg atctcaagtt cattgacggt  600
gaggcgaacg tggaaggatg gcagccctcg tccaacaacg cgaacactgg catcggtgat  660
cacggttcgt gttgtgccga gatggacgtc tgggaagcca actccatctc gaacgcggtc  720
acaccgcacc cgtgtgatac tcctggccag acatatgtgt ccggagatga ttgtggaggc  780
acctattcga acgaccggta tgcaggcacg tgtgacccgg atggctgtga cttcaacccg  840
taccgcatgg gcaacacctc cttctatgga ccgggtaaga tcatcgatac aactaagccc  900
ttcaccgtcg tcacgcagtt cctcacagat gacggcacgg acacaggtac tttgtcggag  960
atcaaacgct tctacgtcca gaacgaaaac gtcatccccc agccgaactc cgacatttcg 1020
ggagtcacag gcaactcgat tacgaccgag ttctgtacag cccagaaaca ggcattcggt 1080
gacacggatg atttctccca gcacggagga ttggcgaaaa tgggagccgc aatgcagcag 1140
ggaatggtcc tcgtgatgtc gctctgggac gactatgcag cccagatgtt gtggctcgac 1200
tcggactacc ccacagacgc cgatcccacg acacccggta tgcacgagg cacttgtccg 1260
acagattccg gagtccccgtc ggacgtcgag tcccagtccc ccaactcgta cgtcacctat 1320
tcgaacatca aattcggtcc catcaactcg acattcacag cctcgggtgg aaaccctcct 1380
ggcggaaacc ctcctggcac aactacaaca cgacggcctg cgactacaac gggttcgtcc 1440
cctggaccga cccagtccca ctacggacag tgtggaggca tcggttattc cggtccgacc 1500
gtctgtgcgt ccggcacaac ctgtcaggtc ttgaaccctt actattcgca gtgtctctaa 1560
```

```
SEQ ID NO: 56          moltype = AA  length = 519
FEATURE                Location/Qualifiers
source                 1..519
                       mol_type = protein
                       organism = Rasamsonia emersonii
SEQUENCE: 56
MLRRALLLSS SAILAVKAQQ AGTATAENHP PLTWQECTAP GSCTTQNGAV VLDANWRWVH   60
DVNGYTNCYT GNTWNPTYCP DDETCAQNCA LDGADYEGTY GVTSSGSSLK LNFVTGSNVG  120
SRLYLLQDDS TYQIFKLLNR EFTFDVDVSN LPCGLNGALY FVAMDADGGV SKYPNNKAGA  180
KYGTGYCDSQ CPRDLKFIDG EANVEGWQPS SNNANTGIGD HGSCCAEMDV WEANSISNAV  240
TPHPCDTPGQ TMCSGDDCGG TYSNDRYAGT CDPDGCDFNP YRMGNTSFYG PGKIIDTTKP  300
FTVVTQFLTD DGTDTGTLSE IKRFYVQNGN VIPQPNSDIS GVTGNSITTE FCTAQKQAFG  360
DTDDFSQHGG LAKMGAAMQQ GMVLVMSLWD DYAAQMLWLD SDYPTDADPT TPGIARGTCP  420
TDSGVPSDVE SQSPNSYVTY SNIKFGPINS TFTASGGNPP GGNPPGTTTT RRPATTTGSS  480
PGPTQSHYGQ CGGIGYSGPT VCASGTTCQV LNPYYSQCL                         519
```

```
SEQ ID NO: 57          moltype = DNA  length = 58
FEATURE                Location/Qualifiers
misc_feature           1..58
                       note = Synthetic Construct DNA Primer
source                 1..58
                       mol_type = other DNA
                       organism = Synthetic Construct
SEQUENCE: 57
ggtcccatca actcgacatt cacagcctcg ggtggaaacc ctcctggcgg aaaccctc    58
```

```
SEQ ID NO: 58          moltype = DNA  length = 21
FEATURE                Location/Qualifiers
misc_feature           1..21
                       note = Synthetic Construct DNA Primer
source                 1..21
                       mol_type = other DNA
                       organism = Synthetic Construct
SEQUENCE: 58
atcctcaatt ccgtcggtcg a                                             21
```

```
SEQ ID NO: 59          moltype = DNA  length = 28
FEATURE                Location/Qualifiers
misc_feature           1..28
                       note = Synthetic Construct DNA Primer
source                 1..28
                       mol_type = other DNA
                       organism = Synthetic Construct
SEQUENCE: 59
ccacacttct cttccttcct caatcctc                                      28
```

```
SEQ ID NO: 60          moltype = DNA  length = 1560
FEATURE                Location/Qualifiers
source                 1..1560
                       mol_type = genomic DNA
                       organism = Rasamsonia emersonii
```

```
SEQUENCE: 60
atgttgcgaa gggccttgtt gctctcgtcc tccgcaatct tggcggtcaa ggcacagcag    60
gcaggcaccg caaccgcaga gaaccatcct ccgctcactt ggcaggaatg tacagcacct   120
ggctcctgta caacccagaa cggagcggtc gtgctcgatg cgaactggcg ctgggtgcac   180
gatgtcaacg gatacacaaa ctgttataca ggtaacacgt ggaaccctac gtattgtccc   240
gacgacgaaa cgtgtgccca gaactgtgcg ttggatggag cagactacga gggaacgtat   300
ggcgtgacct cgtccggctc ctccttgaag ctcaacttcg tcacgggctc gaacgtcggc   360
tcccgcttgt acctcctcca ggacgactcg acctaccaga tcttcaagct cctcaacagg   420
gagttcacct tcgacgtcga tgtctccaac ttgccctgtg gtctcaacgg agccttgtac   480
ttcgtcgcga tggatgcaga cggaggtgtc tcgaagtacc ccaacaacaa ggcaggtgcc   540
aagtatggta ctggctactg tgattcgcag tgtcctcgcg atctcaagtt cattgacggt   600
gaggcgaacg tggaaggatg gcagccctcg tccaacaacg cgaacactgg catcggtgat   660
cacggttcgt gttgtgccga gatggacgtc tgggaagcca actccatctc gaacgcggtc   720
acaccgcacc cgtgtgatac tcctggccag actatgtgtt ccggagatga ttgtggaggc   780
acctattcga acgaccggta tgcaggcacg tgtgacccgg atggctgtga cttcaacccg   840
taccgcatgg gcaacacctc cttctatgga ccgggtaaga tcatcgatac aactaagccc   900
ttcaccgtcg tcacgcagtt cctcacagat gacggcacgg acacaggtac tttgtcggag   960
atcaaacgct tctacgtcca gaacggaaac gtcatcccce agccgaactc cgacatttcg  1020
ggagtcacag gcaactcgat tacgaccgag ttctgtacag cccagaaaca ggcattcggt  1080
gacacggatg atttctccca gcacggagga ttggcgaaaa tgggagccgc aatgcagcag  1140
ggaatggtcc tcgtgatgtc gctctgggac gactatgcag cccagatgtt gtggctcgac  1200
tcggactacc ccacagacgc cgatcccacg acacccggta tcgcacgagg cacttgtccg  1260
acagattccg gagtcccgtc ggacgtcgag tcccagtccc ccaactcgta cgtcacctat  1320
tcgaacatca aattcggtcc catcaactcg acattcacag cctcgggtgg aaaccctcct  1380
ggcggaaacc ctcctggcac aactacaaca cgacggcctg cgactacaac gggttcgtcc  1440
cctggaccga cccagtccca ctacggacag tgtggaggca tcggttattc cggtccgacc  1500
gtctgtgcgt ccggcacaac ctgtcaggtc ttgaacccct actggtcgca gtgtctctaa  1560
```

SEQ ID NO: 61          moltype = AA  length = 519
FEATURE                Location/Qualifiers
source                 1..519
                       mol_type = protein
                       organism = Rasamsonia emersonii

```
SEQUENCE: 61
MLRRALLLSS SAILAVKAQQ AGTATAENHP PLTWQECTAP GSCTTQNGAV VLDANWRWVH    60
DVNGYTNCYT GNTWNPTYCP DDETCAQNCA LDGADYEGTY GVTSSGSSLK LNFVTGSNVG   120
SRLYLLQDDS TYQIFKLLNR EFTFDVDVSN LPCGLNGALY FVAMDADGGV SKYPNNKAGA   180
KYGTGYCDSQ CPRDLKFIDG EANVEGWQPS SNNANTGIGD HGSCCAEMDV WEANSISNAV   240
TPHPCDTPGQ TMCSGDDCGG TYSNDRYAGT CDPDGCDFNP YRMGNTSFYG PGKIIDTTKP   300
FTVVTQFLTD DGTDTGTLSE IKRFYVQNGN VIPQPNSDIS GVTGNSITTE FCTAQKQAFG   360
DTDDFSQHGG LAKMGAAMQQ GMVLVMSLWD DYAAQMLWLD SDYPTDADPT TPGIARGTCP   420
TDSGVPSDVE SQSPNSYVTY SNIKFGPINS TFTASGGNPP GGNPPGTTTT RRPATTTGSS   480
PGPTQSHYGQ CGGIGYSGPT VCASGTTCQV LNPYWSQCL                          519
```

SEQ ID NO: 62          moltype = DNA  length = 1560
FEATURE                Location/Qualifiers
source                 1..1560
                       mol_type = genomic DNA
                       organism = Rasamsonia emersonii

```
SEQUENCE: 62
atgttgcgaa gggccttgtt gctctcgtcc tccgcaatct tggcggtcaa ggcacagcag    60
gcaggcaccg caaccgcaga gaaccatcct ccgctcactt ggcaggaatg tacagcacct   120
ggctcctgta caacccagaa cggagcggtc gtgctcgatg cgaactggcg ctgggtgcac   180
gatgtcaacg gatacacaaa ctgttataca ggtaacacgt ggaaccctac gtattgtccc   240
gacgacgaaa cgtgtgccca gaactgtgcg ttggatggag cagactacga gggaacgtat   300
ggcgtgacct cgtccggctc ctccttgaag ctcaacttcg tcacgggctc gaacgtcggc   360
tcccgcttgt acctcctcca ggacgactcg acctaccaga tcttcaagct cctcaacagg   420
gagttcacct tcgacgtcga tgtctccaac ttgccctgtg gtctcaacgg agccttgtac   480
ttcgtcgcga tggatgcaga cggaggtgtc tcgaagtacc ccaacaacaa ggcaggtgcc   540
aagtatggta ctggctactg tgattcgcag tgtcctcgcg atctcaagtt cattgacggt   600
gaggcgaacg tggaaggatg gcagccctcg tccaacaacg cgaacactgg catcggtgat   660
cacggttcgt gttgtgccga gatggacgtc tgggaagcca actccatctc gaacgcggtc   720
acaccgcacc cgtgtgatac tcctggccag actatgtgtt ccggagatga ttgtggaggc   780
acctattcga acgaccggta tgcaggcacg tgtgacccgg atggctgtga cttcaacccg   840
taccgcatgg gcaacacctc cttctatgga ccgggtaaga tcatcgatac aactaagccc   900
ttcaccgtcg tcacgcagtt cctcacagat gacggcacgg acacaggtac tttgtcggag   960
atcaaacgct tctacgtcca gaacggaaac gtcatcccce agccgaactc cgacatttcg  1020
ggagtcacag gcaactcgat tacgaccgag ttctgtacag cccagaaaca ggcattcggt  1080
gacacggatg atttctccca gcacggagga ttggcgaaaa tgggagccgc aatgcagcag  1140
ggaatggtcc tcgtgatgtc gctctgggac gactatgcag cccagatgtt gtggctcgac  1200
tcggactacc ccacagacgc cgatcccacg acacccggta tcgcacgagg cacttgtccg  1260
acagattccg gagtcccgtc ggacgtcgag tcccagtccc ccaactcgta cgtcacctat  1320
tcgaacatca aattcggtcc catcaactcg acattcacag cctcgggtgg aaaccctcct  1380
ggcggaaacc ctcctggcac aactacaaca cgacggcctg cgactacaac gggttcgtcc  1440
cctggaccga cccagtccca ctggggacag tgtggaggca tcggttattc cggtccgacc  1500
gtctgtgcgt ccggcacaac ctgtcaggtc ttgaacccct actattcgca gtgtctctaa  1560
```

SEQ ID NO: 63          moltype = AA  length = 519
FEATURE                Location/Qualifiers

```
source                    1..519
                          mol_type = protein
                          organism = Rasamsonia emersonii
SEQUENCE: 63
MLRRALLLSS SAILAVKAQQ AGTATAENHP PLTWQECTAP GSCTTQNGAV VLDANWRWVH   60
DVNGYTNCYT GNTWNPTYCP DDETCAQNCA LDGADYEGTY GVTSSGSSLK LNFVTGSNVG  120
SRLYLLQDDS TYQIFKLLNR EFTFDVDVSN LPCGLNGALY FVAMDADGGV SKYPNNKAGA  180
KYGTGYCDSQ CPRDLKFIDG EANVEGWQPS SNNANTGIGD HGSCCAEMDV WEANSISNAV  240
TPHPCDTPGQ TMCSGDDCGG TYSNDRYAGT CDPDGCDFNP YRMGNTSFYG PGKIIDTTKP  300
FTVVTQFLTD DGTDTGTLSE IKRFYVQNGN VIPQPNSDIS GVTGNSITTE FCTAQKQAFG  360
DTDDFSQHGG LAKMGAAMQQ GMVLVMSLWD DYAAQMLWLD SDYPTDADPT TPGIARGTCP  420
TDSGVPSDVE SQSPNSYVTY SNIKFGPINS TFTASGGNPP GGNPPGTTTT RRPATTTGSS  480
PGPTQSHWGQ CGGIGYSGPT VCASGTTCQV LNPYYSQCL                        519

SEQ ID NO: 64            moltype = DNA   length = 41
FEATURE                  Location/Qualifiers
misc_feature             1..41
                         note = Synthetic Construct DNA Primer
source                   1..41
                         mol_type = other DNA
                         organism = Synthetic Construct
SEQUENCE: 64
ctgtcaggtc ttgaacccTT actggtcgca gtgtctctaa g                      41

SEQ ID NO: 65            moltype = DNA   length = 32
FEATURE                  Location/Qualifiers
misc_feature             1..32
                         note = Synthetic Construct DNA Primer
source                   1..32
                         mol_type = other DNA
                         organism = Synthetic Construct
SEQUENCE: 65
gtaagggttc aagacctgac aggttgtgcc gg                                32

SEQ ID NO: 66            moltype = DNA   length = 43
FEATURE                  Location/Qualifiers
misc_feature             1..43
                         note = Synthetic Construct DNA Primer
source                   1..43
                         mol_type = other DNA
                         organism = Synthetic Construct
SEQUENCE: 66
ctggaccgac ccagtcccac tggggacagt gtggaggcat cgg                    43

SEQ ID NO: 67            moltype = DNA   length = 30
FEATURE                  Location/Qualifiers
misc_feature             1..30
                         note = Synthetic Construct DNA Primer
source                   1..30
                         mol_type = other DNA
                         organism = Synthetic Construct
SEQUENCE: 67
gtgggactgg gtcggtccag gggacgaacc                                   30

SEQ ID NO: 68            moltype = DNA   length = 28
FEATURE                  Location/Qualifiers
misc_feature             1..28
                         note = Synthetic Construct DNA Primer
source                   1..28
                         mol_type = other DNA
                         organism = Synthetic Construct
SEQUENCE: 68
ccacacttct cttccttcct caatcctc                                     28

SEQ ID NO: 69            moltype = DNA   length = 22
FEATURE                  Location/Qualifiers
misc_feature             1..22
                         note = Synthetic Construct DNA Primer
source                   1..22
                         mol_type = other DNA
                         organism = Synthetic Construct
SEQUENCE: 69
gtgaggcgaa cgtggaagga tg                                           22

SEQ ID NO: 70            moltype = DNA   length = 25
FEATURE                  Location/Qualifiers
misc_feature             1..25
                         note = Synthetic Construct DNA Primer
source                   1..25
```

```
                         mol_type = other DNA
                         organism = Synthetic Construct
SEQUENCE: 70
gtacctgtgt ccgtgccgtc atctg                                       25

SEQ ID NO: 71           moltype = DNA   length = 21
FEATURE                 Location/Qualifiers
misc_feature            1..21
                         note = Synthetic Construct DNA Primer
source                  1..21
                         mol_type = other DNA
                         organism = Synthetic Construct
SEQUENCE: 71
atcctcaatt ccgtcggtcg a                                           21

SEQ ID NO: 72           moltype = DNA   length = 1560
FEATURE                 Location/Qualifiers
source                  1..1560
                         mol_type = genomic DNA
                         organism = Rasamsonia emersonii
SEQUENCE: 72
atgttgcgaa gggccttgtt gctctcgtcc tccgcaatct tggcggtcaa ggcacagcag   60
gcaggcaccg caaccgcaga gaaccatcct ccgctcactt ggcaggaatg tacagcacct  120
ggctcctgta caacccagaa cggagcggtc gtgctcgatg cgaactggcg ctgggtgcac  180
gatgtcaacg gatacacaaa ctgttataca ggtaacacgt ggaaccctac gtattgtccc  240
gacgacgaaa cgtgtgccca gaactgtgcg ttggatgagg acacatacga gggaacgtat  300
ggcgtgacct cgtccggctc ctccttgaag ctcaacttcg tcacgggctc gaacgtcggc  360
tcccgcttgt acctcctcca ggacgactcg acctaccaga tcttcaagct cctcaacagg  420
gagttcacct tcgacgtcga tgtctccaac ttgccctgtg gtctcaacgg agccttgtac  480
ttcgtcgcga tggatgcaga cggaggtgtc tcgaagtacc ccaacaacaa ggcaggtgcc  540
aagtatggta ctggctactg tgattcgcag tgtcctcgcg atctcaagtt cattgacggt  600
gaggcgaacg tggaaggatg gcagccctcg tccaacaacg cgaacactgg catcggtgat  660
cacggttcgt gttgtgccga gatggacgtc tgggaagcca actccatctc gaacgcggtc  720
acaccgacac cgtgtgatac tcctggccag actatgtgtt ccggagatga ttgtggaggc  780
acctattcga acgaccggta tgcaggcacg tgtgacccgg atggctgtga cttcaacccg  840
taccgcatgg gcaacacctc cttctatgga ccgggtaaga tcatcgatac aactaagccc  900
ttcaccgtcg tcacgcagtt cctcacagat gacggcacgg acacaggtac tttgtcggag  960
atcaaacgct tctacgtcca gaacggaaac gtcatccccc agccgaactc cgacatttcg 1020
ggagtcacag gcaactcgat tacgaccgag ttctgtacag cccagaaaca ggcattcggt 1080
gacacggatg atttctccca gcacggagga ttggcgaaaa tgggagccgc aatgcagcag 1140
ggaatggtcc tcgtgatgtc gctctgggac gactatgcag cccagatgtt gtggctcgac 1200
tcggactacc ccacagacgc cgatcccacg acacccggta tcgcacgagg cacttgtccg 1260
acagattccg gagtcccgtc ggacgtcgag tcccagtccc ccaactcgta cgtcacctat 1320
tcgaacatca aattcggtcc catcaactcg acattcacag cctcgggtgg aaaccctcct 1380
ggcggaaacc ctcctggcac aactacaaca cgacggcctg cgactacaac gggttcgtcc 1440
cctggaccga cccagtccca ctacggacag tgtggaggca tcggttggtc cggtccgacc 1500
gtctgtgcgt ccggcacaac ctgtcaggtc ttgaacccctt actattcgca gtgtctctaa 1560

SEQ ID NO: 73           moltype = AA   length = 519
FEATURE                 Location/Qualifiers
source                  1..519
                         mol_type = protein
                         organism = Rasamsonia emersonii
SEQUENCE: 73
MLRRALLLSS SAILAVKAQQ AGTATAENHP PLTWQECTAP GSCTTQNGAV VLDANWRWVH   60
DVNGYTNCYT GNTWNPTYCP DDETCAQNCA LDGADYEGTY GVTSSGSSLK LNFVTGSNVG  120
SRLYLLQDDS TYQIFKLLNR EFTFDVDVSN LPCGLNGALY FVAMDADGGV SKYPNNKAGA  180
KYGTGYCDSQ CPRDLKFIDG EANVEGWQPS SNNANTGIGD HGSCCAEMDV WEANSISNAV  240
TPHPCDTPGQ TMCSGDDCGG TYSNDRYAGT CDPDGCDFNP YRMGNTSFYG PGKIIDTTKP  300
FTVVTQFLTD DGTDTGTLSE IKRFYVQNGN VIPQPNSDIS GVTGNSITTE FCTAQKQAFG  360
DTDDFSQHGG LAKMGAAMQQ GMVLVMSLWD DYAAQMLWLD SDYPTDADPT TPGIARGTCP  420
TDSGVPSDVE SQSPNSYVTY SNIKFGPINS TFTASGGNPP GGNPPGTTTT RRPATTTGSS  480
PGPTQSHYGQ CGGIGWSGPT VCASGTTCQV LNPYYSQCL                         519

SEQ ID NO: 74           moltype = DNA   length = 44
FEATURE                 Location/Qualifiers
misc_feature            1..44
                         note = Synthetic Construct DNA Primer
source                  1..44
                         mol_type = other DNA
                         organism = Synthetic Construct
SEQUENCE: 74
ggacagtgtg gaggcatcgg ttggtccggt ccgaccgtct gtgc                  44

SEQ ID NO: 75           moltype = DNA   length = 32
FEATURE                 Location/Qualifiers
misc_feature            1..32
                         note = Synthetic Construct DNA Primer
source                  1..32
```

-continued

```
                          mol_type = other DNA
                          organism = Synthetic Construct
SEQUENCE: 75
accgatgcct ccacactgtc cgtagtggga ct                                32

SEQ ID NO: 76             moltype = DNA  length = 1599
FEATURE                   Location/Qualifiers
source                    1..1599
                          mol_type = genomic DNA
                          organism = Aspergillus fumigatus
SEQUENCE: 76
atgctggcct ccaccttctc ctaccgcatg tacaagaccg cgctcatcct ggccgccctt   60
ctgggctctg gccaggctca gcaggtcggt acttcccagg cggaagtgca tccgtccatg  120
acctggcaga gctgcacggc tggcggcagc tgcaccacca acaacggcaa ggtggtcatc  180
gacgcgaact ggcgttgggt gcacaaagtc ggcgactaca ccaactgcta caccggcaac  240
acctgggaca cgactatctg ccctgacgat gcgacctgcg catccaactg cgcccttgag  300
ggtgccaact acgaatccac ctatggtgtg accgccagcg gcaattccct ccgcctcaac  360
ttcgtcacca ccagccagca gaagaacatt ggctcgcgtc tgtacatgat gaaggacgac  420
tcgacctacg agatgtttaa gctgctgaac caggagttca ccttcgatgt cgatgtctcc  480
aacctcccct gcggtctcaa cggtgctctg tactttgtcg ccatggacgc cgacggtggc  540
atgtccaagt acccaaccaa caaggccggt gccaagtacg gtactggata ctgtgactcg  600
cagtgccctc gcgacctcaa gttcatcaac ggtcaggcca acgttgaagg gtggcagccc  660
tcctccaacg atgccaatgc gggtaccggc aaccacgggt cctgctgcgc ggagatggat  720
atctgggagg ccaacagcat ctccacggcc ttcacccccc atccgtgcga cacgcccggc  780
caggtgatgt gcaccggtga tgcctgcggt ggcacctaca gctccgaccg ctacggcggc  840
acctgcgacc ccgacggatg tgatttcaac tccttccgcc agggcaacaa gaccttctac  900
ggccctggca tgaccgtcga caccaagagc aagtttaccg tcgtcaccca gttcatcacc  960
gacgacggca cctccagcgg caccctcaag gagatcaagc gcttctacgt gcagaacggc 1020
aaggtgatcc ccaactcgga gtcgacctgg accggcgtca gcggcaactc catcaccacc 1080
gagtactgca ccgcccagaa aagcctgttc caggaccaga acgtcttcga aaagcacggc 1140
ggcctcgagg gcatgggtgc tgccctcgcc cagggcatgg ttctcgtcat gtccctgtgg 1200
gatgatcact cggccaacat gctctggctc gacagcaact acccgaccac tgcctcttcc 1260
accactcccg gcgtcgcccg tggtacctgc gacatctcct ccggcgtccc tgcggatgtc 1320
gaggcgaacc accccgacgc ctacgtcgtc tactccaaca tcaaggtcgg ccccatcggc 1380
tcgaccttca acagcggtgg ctcgaacccc ggtggcggaa ccaccacgac aactaccacc 1440
cagcctacta ccaccacgac cacggctgga aaccctggcg gcaccggagt cgcacagcac 1500
tatgccagt gtggtggaat cggatggacc ggacccacaa cctgtgccag cccttatacc 1560
tgccagaagc tgaatgatta ttactctcag tgcctgtag                        1599

SEQ ID NO: 77             moltype = DNA  length = 1599
FEATURE                   Location/Qualifiers
source                    1..1599
                          mol_type = genomic DNA
                          organism = Aspergillus fumigatus
SEQUENCE: 77
atgctggcct ccaccttctc ctaccgcatg tacaagaccg cgctcatcct ggccgccctt   60
ctgggctctg gccaggctca gcaggtcggt acttcccagg cggaagtgca tccgtccatg  120
acctggcaga gctgcacggc tggcggcagc tgcaccacca acaacggcaa ggtggtcatc  180
gacgcgaact ggcgttgggt gcacaaagtc ggcgactaca ccaactgcta caccggcaac  240
acctgggaca cgactatctg ccctgacgat gcgacctgcg catccaactg cgcccttgag  300
ggtgccaact acgaatccac ctatggtgtg accgccagcg gcaattccct ccgcctcaac  360
ttcgtcacca ccagccagca gaagaacatt ggctcgcgtc tgtacatgat gaaggacgac  420
tcgacctacg agatgtttaa gctgctgaac caggagttca ccttcgatgt cgatgtctcc  480
aacctcccct gcggtctcaa cggtgctctg tactttgtcg ccatggacgc cgacggtggc  540
atgtccaagt acccaaccaa caaggccggt gccaagtacg gtactggata ctgtgactcg  600
cagtgccctc gcgacctcaa gttcatcaac ggtcaggcca acgttgaagg gtggcagccc  660
tcctccaacg atgccaatgc gggtaccggc aaccacgggt cctgctgcgc ggagatggat  720
atctgggagg ccaacagcat ctccacggcc ttcacccccc atccgtgcga cacgcccggc  780
caggtgatgt gcaccggtga tgcctgcggt ggcacctaca gctccgaccg ctacggcggc  840
acctgcgacc ccgacggatg tgatttcaac tccttccgcc agggcaacaa gaccttctac  900
ggccctggca tgaccgtcga caccaagagc aagtttaccg tcgtcaccca gttcatcacc  960
gacgacggca cctccagcgg caccctcaag gagatcaagc gcttctacgt gcagaacggc 1020
aaggtgatcc ccaactcgga gtcgacctgg accggcgtca gcggcaactc catcaccacc 1080
gagtactgca ccgcccagaa aagcctgttc caggaccaga acgtcttcga aaagcacggc 1140
ggcctcgagg gcatgggtgc tgccctcgcc cagggcatgg ttctcgtcat gtccctgtgg 1200
gatgatcact cggccaacat gctctggctc gacagcaact acccgaccac tgcctcttcc 1260
accactcccg gcgtcgcccg tggtacctgc gacatctcct ccggcgtccc tgcggatgtc 1320
gaggcgaacc accccgacgc ctacgtcgtc tactccaaca tcaaggtcgg ccccatcggc 1380
tcgaccttca acagcggtgg ctcgaacccc ggtggcggaa ccaccacgac aactaccacc 1440
cagcctacta ccaccacgac cacggctgga aaccctggcg gcaccggagt cgcacagcac 1500
tatgccagt gtggtggaat cggatggacc ggacccacaa cctgtgccag cccttatacc 1560
tgccagaagc tgaatgatta ttactctcag tgcctgtag                        1599

SEQ ID NO: 78             moltype = AA  length = 532
FEATURE                   Location/Qualifiers
source                    1..532
                          mol_type = protein
                          organism = Aspergillus fumigatus
SEQUENCE: 78
```

```
MLASTFSYRM YKTALILAAL LGSGQAQQVG TSQAEVHPSM TWQSCTAGGS CTTNNGKVVI    60
DANWRWVHKV GDYTNCYTGN TWDTTICPDD ATCASNCALE GANYESTYGV TASGNSLRLN   120
FVTTSQQKNI GSRLYMMKDD STYEMFKLLN QEFTFDVDVS NLPCGLNGAL YFVAMDADGG   180
MSKYPTNKAG AKYGTGYCDS QCPRDLKFIN GQANVEGWQP SSNDANAGTG NHGSCCAEMD   240
IWEANSISTA FTPHPCDTPG QVMCTGDACG GTYSSDRYGG TCDPDGCDFN SFRQGNKTFY   300
GPGMTVDTKS KFTVVTQFIT DDGTSSGTLK EIKRFYVQNG KVIPNSESTW TGVSGNSITT   360
EYCTAQKSLF QDQNVFEKHG GLEGMGAALA QGMVLVMSLW DDHSANMLWL DSNYPTTASS   420
TTPGVARGTC DISSGVPADV EANHPDAYVV YSNIKVGPIG STFNSGGSNP GGGTTTTTTT   480
QPTTTTTTAG NPGGTGVAQH YGQCGGIGWT GPTTCASPYT CQKLNDYYSQ CL           532
```

```
SEQ ID NO: 79                  moltype = DNA  length = 1599
FEATURE                        Location/Qualifiers
source                         1..1599
                               mol_type = genomic DNA
                               organism = Aspergillus fumigatus
SEQUENCE: 79
atgttggcct ccacgttctc ctatcgcatg tacaaaacag cgctcatctt ggcagccctc    60
ttgggctcgg gacaggcaca gcaggtcgga acctcgcagg ccgaggtcca tccttccatg   120
acgtggcagt cgtgtacagc gggtggttcg tgtaccacaa acaacggtaa agtcgtgatc   180
gatgcaaact ggaggtgggt gcacaaggtc ggcgactaca ccaactgtta cacaggcaac   240
acatgggata caaccatctg tcccgacgat gccacttgtg catccaactg tgcactcgag   300
ggtgccaact atgagtcgac gtacggagtg accgcctccg gcaatccttc caggctcaac   360
ttcgtcacaa cttcccagca gaagaacatc ggctcgcggt tgtatatgat gaaagacgat   420
tccacttacg agatgttcaa gctcctcaac caggaattca ctttcgatgt cgacgtctcc   480
aacctccctt gtggcttgaa cggagcgctc tacttcgtcg ccatggatgc ggatggaggc   540
atgtccaagt atcctaccaa caaagcagga gccaagtatg gtacaggtta ctgtgattcc   600
cagtgtccca gggatctcaa gttcatcaac ggtcaggcca acgtcgaggg ttggcagcct   660
tcgtcgaacg atgccaacgc aggtaccggc aaccacggtt cctgttgtgc cgaaatggac   720
atttgggaag cgaactcgat ctcgacggcg ttcactcctc accgtgtgac tacacccgga   780
caggtgatgt gtacaggcga cgcctgtggc ggaacctact cgtcggatcg atatggcggt   840
acgtgtgacc ccgacggctg tgacttcaac tccttcaggc agggcaacaa aacattctat   900
ggacctggca tgacggtgga tacaaagtcg aaattcacag tcgtcactca gttcatcacc   960
gacgatggta cgtcctcggg taccttgaag gagatcaaaa ggttctatgt ccagaacgga  1020
aaggtcatcc cgaactcgga gtccacgtgg acaggagtgt cgggtaactc catcactacg  1080
gagtattgta cagcccagaa gtcgctcttc caggatcaga acgtcttcga gaaacatgga  1140
ggcttggaag gaatgggtgc cgcattggcc cagggtatgg tcctcgtcat gtccttgtgg  1200
gacgaccact cggccaacat gctctggttg gattccaact accccaccac tgcctcgtcc  1260
acgacaccgg gtgtcgcacg cggaacttgt gatatctcct cgggagtgcc tgcagacgtc  1320
gaggcgaacc atcccgacgc ctacgtggtc tactcgaaca ttaaggtggg acccatcggt  1380
tcgacattca actccggagg ctcgaaccct ggaggcggaa cgaccactac tacaacgact  1440
cagccgacaa caacaactac cacagcaggc aaccctggag gtacaggtgt ggcccagcac  1500
tacgacagt gtggcggtat cggatggaca ggacctacta cttgtgcatc gccttatacc  1560
tgtcagaaat tgaacgacta ctactcgcag tgtttgtaa                          1599
```

```
SEQ ID NO: 80                  moltype = DNA  length = 25
FEATURE                        Location/Qualifiers
misc_feature                   1..25
                               note = Synthetic Construct DNA Primer
source                         1..25
                               mol_type = other DNA
                               organism = Synthetic Construct
SEQUENCE: 80
gtgatacacc cggacaggtg atgtg                                           25
```

```
SEQ ID NO: 81                  moltype = DNA  length = 25
FEATURE                        Location/Qualifiers
misc_feature                   1..25
                               note = Synthetic Construct DNA Primer
source                         1..25
                               mol_type = other DNA
                               organism = Synthetic Construct
SEQUENCE: 81
ccatatcgat ccgacgagta ggttc                                          25
```

```
SEQ ID NO: 82                  moltype = DNA  length = 1507
FEATURE                        Location/Qualifiers
source                         1..1507
                               mol_type = genomic DNA
                               organism = Talaromyces byssochlamydoides
SEQUENCE: 82
atgtttcgac gggctctttt cctgtcctct tccgccttcc ttgctgtcaa agcccagcag    60
atcggcacgt cagtccgga gaaccatccg ccccctggcat gggagcagtg cactgcccct   120
gggagttgca cgactgtgaa tggtgcggtc gtccttgatg cgaactggcg ttgggtccac   180
aatgttgggg gatacaccaa ctgctacact ggcaatacct ggcagaccac gtactgccct   240
gacgacgtga cctgcgcaga gaattgtgcg ctggatggcg cagattacga gggcacctac   300
ggcgtgacca cctcgggcag ctccctgaag ctcgatttcg tcaccgggtc taacgtcgga   360
tctcgtctct acctgttgga gaatgattcg acctatcaga tcttcaagct ctgaaccag   420
gaattcacct ttgacgtcga cgtttccaat cttccgtgcg gattaaacgg cgctctgtac   480
cttgttacca tggctgctga cggcgggggtg tctcagtacc cgaataacaa ggccggcgca   540
```

```
gcgtatggaa ccggttattg cgattcccag tgtccaaggg acttgaagtt tatcgatggc    600
caggtatgta gagctgtaat cacccatgtt gtgaaatcac tctcctactg acatggtcga    660
tttataggcc aacgttgagg gctggcagcc gtcttcgaac aacgccaata caggtattgg    720
caaccatggc tcctgctgtg cggagatgga tatctgggaa gccaacagca tctccaatgc    780
ggtgactccg cacccatgcg acacacccgg ccagacaatg tgcgagggga acgactgtgg    840
tggcacgtat tccaccaatc gctatgcagg cacctgcgat cctgacggct gcgacttcaa    900
cccctaccgc atgggcaacc attctttcta cggccctggg gagattgtcg atactaccca    960
gcccttcact gtcgtgacac agttccttac cgatgatggc acggatactg gcactctcag   1020
cgagatcaaa cgcttctacg tccaaaacgg gaaagtcatt cctcagccga actccgacat   1080
tgccggcgtg actggcaact cgatcaccag cgagtttgc gatgcccaga agacggcttt    1140
cggcgacatt aacaactttg atacacacg cggtctggcc agtatgggag ctgcgctgca   1200
gcagggtatg gttctggtga tgagtctgtg ggacggtagg tccttgggag acacccggac   1260
gttctatatc aaccagaact gccagaactg acgaattaaa acacttttag attacgcggc   1320
aaacatgctg tggttggaca gcatttatcc aacaaatgca tctgctagca ctcctggtgc   1380
tgctcgtgga acctgttcga cgagctccgg tgtcccatcg caagtcgagt cgcagagccc   1440
caacgcctac gtgacgtact ccaacattaa agttggacca atcaactcga ccttcaccac   1500
ttcgtaa                                                             1507
```

```
SEQ ID NO: 83            moltype = AA   length = 455
FEATURE                  Location/Qualifiers
source                   1..455
                         mol_type = protein
                         organism = Talaromyces byssochlamydoides
SEQUENCE: 83
MFRRALFLSS SAFLAVKAQQ IGTVSPENHP PLAWEQCTAP GSCTTVNGAV VLDANWRWVH     60
NVGGYTNCYT GNTWDTTYCP DDVTCAENCA LDGADYEGTY GVTTSGSSLK LDFVTGSNVG    120
SRLYLLENDS TYQIFKLLNQ EFTFDVDVSN LPCGLNGALY LVTMAADGGV SQYPNNKAGA    180
AYGTGYCDSQ CPRDLKFIDG QANVEGWQPS SNNANTGIGN HGSCCAEMDI WEANSISNAV    240
TPHPCDTPGQ TMCEGNDCGG TYSTNRYAGT CDPDGCDFNP YRMGNHSFYG PGEIVDTTQP    300
FTVVTQFLTD DGTDTGTLSE IKRFYVQNGK VIPQPNSDIA GVTGNSITSE FCDAQKTAFG    360
DINNFDTHGG LASMGAALQQ GMVLVMSLWD DYAANMLWLD SIYPTNASAS TPGAARGTCS    420
TSSGVPSQVE SQSPNAYVTY SNIKVGPINS TFTTS                               455
```

```
SEQ ID NO: 84            moltype = DNA   length = 1705
FEATURE                  Location/Qualifiers
source                   1..1705
                         mol_type = genomic DNA
                         organism = Talaromyces byssochlamydoides
SEQUENCE: 84
atgtttcgac gggctctttt cctgtcctct tccgccttcc ttgctgtcaa agcccagcag     60
atcggcacgg tcagtccgga gaaccatccg cccctggcat gggagcagtg cactgcccct    120
gggagttgca cgactgtgaa tggtgcggtc gtccttgatg cgaactggcg ttgggtccaa    180
aatgttgggg gatacaccaa ctgctacact ggcaatacct ggacaccac gtactgccct    240
gacgacgtga cctgcgcaga gaattgtgcg ctggatggcg cagattacga gggcacctac    300
ggcgtgacca cctcgggcag ctccctgaag ctcgatttcg tcaccgggtc taacgtcgga    360
tctcgtctct acctgttgga gaatgattcg acctatcaga tcttcaagct tctgaaccag    420
gaattcacct ttgacgtcga cgtttccaat cttccgtgcg gattaaacgg cgctctgtac    480
cttgttacca tggctgctga cggcggggtg tctcagtacc cgaataacaa ggccggcgca    540
gcgtatggaa ccggttattg cgattcccag tgtccaaggg acttgaagtt tatcgatggc    600
caggtatgta gagctgtaat cacccatgtt gtgaaatcac tctcctactg acatggtcga    660
tttataggcc aacgttgagg gctggcagcc gtcttcgaac aacgccaata caggtattgg    720
caaccatggc tcctgctgtg cggagatgga tatctgggaa gccaacagca tctccaatgc    780
ggtgactccg cacccatgcg acacacccgg ccagacaatg tgcgagggga acgactgtgg    840
tggcacgtat tccaccaatc gctatgcagg cacctgcgat cctgacggct gcgacttcaa    900
cccctaccgc atgggcaacc attctttcta cggccctggg gagattgtcg atactaccca    960
gcccttcact gtcgtgacac agttccttac cgatgatggc acggatactg gcactctcag   1020
cgagatcaaa cgcttctacg tccaaaacgg gaaagtcatt cctcagccga actccgacat   1080
tgccggcgtg actggcaact cgatcaccag cgagtttgc gatgcccaga agacggcttt    1140
cggcgacatt aacaactttg atacacacg cggtctggcc agtatgggag ctgcgctgca   1200
gcagggtatg gttctggtga tgagtctgtg ggacggtagg tccttgggag acacccggac   1260
gttctatatc aaccagaact gccagaactg acgaattaaa acacttttag attacgcggc   1320
aaacatgctg tggttggaca gcatttatcc aacaaatgca tctgctagca ctcctggtgc   1380
tgctcgtgga acctgttcga cgagctccgg tgtcccatcg caagtcgagt cgcagagccc   1440
caacgcctac gtgacgtact ccaacattaa agttggacca atcaactcga ccttcaccac   1500
ttcgggctcg aaccctggag gcggaacgac cactactaca acgactcagc cgacaacaac   1560
aactaccaca gcaggcaacc ctggaggtac aggtgtggcc cagcactacg gacagtgtgg   1620
cggtatcgga tggacaggac ctactacttg tgcatcgcct tatacctgtc agaaattgaa   1680
cgactactac tcgcagtgtt tgtaa                                         1705
```

```
SEQ ID NO: 85            moltype = AA   length = 521
FEATURE                  Location/Qualifiers
source                   1..521
                         mol_type = protein
                         organism = Talaromyces byssochlamydoides
SEQUENCE: 85
MFRRALFLSS SAFLAVKAQQ IGTVSPENHP PLAWEQCTAP GSCTTVNGAV VLDANWRWVH     60
NVGGYTNCYT GNTWDTTYCP DDVTCAENCA LDGADYEGTY GVTTSGSSLK LDFVTGSNVG    120
SRLYLLENDS TYQIFKLLNQ EFTFDVDVSN LPCGLNGALY LVTMAADGGV SQYPNNKAGA    180
AYGTGYCDSQ CPRDLKFIDG QANVEGWQPS SNNANTGIGN HGSCCAEMDI WEANSISNAV    240
```

```
TPHPCDTPGQ TMCEGNDCGG TYSTNRYAGT CDPDGCDFNP YRMGNHSFYG PGEIVDTTQP  300
FTVVTQFLTD DGTDTGTLSE IKRFYVQNGK VIPQPNSDIA GVTGNSITSE FCDAQKTAFG  360
DINNFDTHGG LASMGAALQQ GMVLVMSLWD DYAANMLWLD SIYPTNASAS TPGAARGTCS  420
TSSGVPSQVE SQSPNAYVTY SNIKVGPINS TFTTSGSNPG GGTTTTTTTQ PTTTTTTAGN  480
PGGTGVAQHY GQCGGIGWTG PTTCASPYTC QKLNDYYSQC L                       521

SEQ ID NO: 86              moltype = DNA   length = 50
FEATURE                    Location/Qualifiers
misc_feature               1..50
                           note = Synthetic Construct DNA Primer
source                     1..50
                           mol_type = other DNA
                           organism = Synthetic Construct
SEQUENCE: 86
caatcaactc gaccttcacc acttcgggct cgaaccctgg aggcggaacg              50

SEQ ID NO: 87              moltype = DNA   length = 34
FEATURE                    Location/Qualifiers
misc_feature               1..34
                           note = Synthetic Construct DNA Primer
source                     1..34
                           mol_type = other DNA
                           organism = Synthetic Construct
SEQUENCE: 87
ctagatctcg agttacaaac actgcgagta gtag                               34

SEQ ID NO: 88              moltype = DNA   length = 26
FEATURE                    Location/Qualifiers
misc_feature               1..26
                           note = Synthetic Construct DNA Primer
source                     1..26
                           mol_type = other DNA
                           organism = Synthetic Construct
SEQUENCE: 88
cgaagtggtg aaggtcgagt tgattg                                        26

SEQ ID NO: 89              moltype = DNA   length = 1599
FEATURE                    Location/Qualifiers
source                     1..1599
                           mol_type = genomic DNA
                           organism = Aspergillus fumigatus
SEQUENCE: 89
atgttggcct ccacgttctc ctatcgcatg tacaaaacag cgctcatctt ggcagccctc  60
ttgggctcgg gacaggcaca gcaggtcgga acctcgcagg ccgaggtcca tccttccatg  120
acgtggcagt cgtgtacagc gggtggttcg tgtaccacaa acaacggtaa agtcgtgatc  180
gatgcaaact ggaggtgggt gcacaaggtc ggcgactaca ccaactgtta cacaggcaac  240
acatgggata caaccatctg tcccgacgat gccacttgtg catccaactg tgcactcgag  300
ggtgccaact atgagtcgac gtacggagtg accgcctccg gaaactcgct caggctcaac  360
ttcgtcacaa cttcccagca gaagaacatc ggctcgcggt tgtatatgat gaaagacgat  420
tccacttacg agatgttcaa gctcctcaac caggaattca ctttcgatgt cgacgtctcc  480
aacctccctt gtggcttgaa cggagcgctc tacttcgtcg ccatggatgc ggatggaggc  540
atgtccaagt atcctaccaa caaagcagga gccaagtatg gtacaggtta ctgtgattcc  600
cagtgtccca gggatctcaa gttcatcaac ggtcaggcca acgtcgaggg ttggcagcct  660
tcgtcgaacg atgccaacgc aggtaccggc aaccacggtt cctgttgtgc cgaaatggac  720
atttgggaag cgaactcgat ctcgacggcg ttcactcctc acccgtgtga tacacccgga  780
caggtgatgt gtacaggcga cgcctgtgtc ggaacctact cgtcggatcg atatggcggt  840
acgtgtgacc ccgacggctg tgacttcaac tccttcaggc agggcaacaa aacattctat  900
ggacctggca tgacggtgga tacaaagtcg aaattcacag tcgtcactca gttcatcacc  960
gacgatggta cgtcctcggg taccttgaag gagatcaaaa ggttctatgt ccagaacgga  1020
aaggtcatcc cgaactcgga gtccacgtag acaggagtgt cgggtaactc catcactacg  1080
gagtattgta cagcccagaa gtcgctcttc caggatcaga acgtcttcga gaaacatgga  1140
ggcttggaag gaatgggtgc cgcattggcc cagggtatgg tcctcgtcat gtccttgtgg  1200
gacgaccact cggccaacat gctctggttg gattccaact accccaccac tgcctcgtcc  1260
acgacaccgg tgtcgcacg cggaacttgt gatatctcct cgcagacgcc tgcagacgtc  1320
gaggcgaacc atcccgacgc ctacgtggtc tactcgaaca ttaaggtggg acccatcggt  1380
tcgacattca actccggagg ctcgaaccct ggaggcggaa cgaccactac tacaacgact  1440
cagccgacaa caacaactac cacagcaggc aaccctggag gtacaggtgt ggcccagcac  1500
tggggacagt gtggcggtat cggatggaca ggacctacta cttgtgcatc gccttatacc  1560
tgtcagaaat tgaacgacta ctactcgcag tgtttgtaa                          1599

SEQ ID NO: 90              moltype = AA   length = 532
FEATURE                    Location/Qualifiers
source                     1..532
                           mol_type = protein
                           organism = Aspergillus fumigatus
SEQUENCE: 90
MLASTFSYRM YKTALILAAL LGSGQAQQVG TSQAEVHPSM TWQSCTAGGS CTTNNGKVVI  60
DANWRWVHKV GDYTNCYTGN TWDTTICPDD ATCASNCALE GANYESTYGV TASGNSLRLN  120
FVTTSQQKNI GSRLYMMKDD STYEMFKLLN QEFTFDVDVS NLPCGLNGAL YFVAMDADGG  180
```

```
MSKYPTNKAG AKYGTGYCDS QCPRDLKFIN GQANVEGWQP SSNDANAGTG NHGSCCAEMD  240
IWEANSISTA FTPHPCDTPG QVMCTGDACG GTYSSDRYGG TCDPDGCDFN SFRQGNKTFY  300
GPGMTVDTKS KFTVVTQFIT DDGTSSGTLK EIKRFYVQNG KVIPNSESTW TGVSGNSITT  360
EYCTAQKSLF QDQNVFEKHG GLEGMGAALA QGMVLVMSLW DDHSANMLWL DSNYPTTASS  420
TTPGVARGTC DISSGVPADV EANHPDAYVV YSNIKVGPIG STFNSGGSNP GGGTTTTTTT  480
QPTTTTTTAG NPGGTGVAQH WGQCGGIGWT GPTTCASPYT CQKLNDYYSQ CL          532

SEQ ID NO: 91              moltype = DNA   length = 1599
FEATURE                    Location/Qualifiers
source                     1..1599
                           mol_type = genomic DNA
                           organism = Aspergillus fumigatus
SEQUENCE: 91
atgttggcct ccacgttctc ctatcgcatg tacaaaacag cgctcatctt ggcagccctc   60
ttgggctcgg gacaggcaca gcaggtcgga acctcgcagg ccgaggtcca tccttccatg  120
acgtggcagt cgtgtacagc gggtggttcg tgtaccacaa acaacggtaa agtcgtgatc  180
gatgcaaact ggaggtgggt gcacaaggtc ggcgactaca ccaactgtta cacaggcaac  240
acatgggata caaccatctg tcccgacgat gccacttgtg catccaactg tgcactcgag  300
ggtgccaact atgagtcgac gtacggagtg accgcctccg gaaactcgct caggctcaac  360
ttcgtcacaa cttcccagca gaagaacatc ggctcgcggt tgtatatgat gaaagacgat  420
tccacttacg agatgttcaa gctcctcaac caggaattca ctttcgatgt cgacgtctcc  480
aacctccctt gtggcttgaa cggagcgctc tacttcgtcg ccatggatgc ggatggaggc  540
atgtccaagt atcctaccaa caaagcagga gccaagtatg gtacaggtta ctgtgattcc  600
cagtgtccca gggatctcaa gttcatcaac ggtcaggcca acgtcgaggg ttggcagcct  660
tcgtcgaacg atgccaacgc aggtaccggc aaccacggtt cctgttgtgc cgaaatggac  720
atttgggaag cgaactcgat ctcgacggcg ttcactcctc accgtgtga tacacccgga  780
caggtgatgt gtacaggcga cgcctgtggc ggaacctact cgtcggatcg atatggcggt  840
acgtgtgacc ccgacggctg tgacttcaac tccttcaggc agggcaacaa aacattctat  900
ggacctggca tgacggtgga tacaaagtcg aaattcacag tcgtcactca gttcatcacc  960
gacgatggta cgtcctcggg taccttgaag gagatcaaaa ggttctatgt ccagaacgga 1020
aaggtcatcc cgaactcgga gtccacgtgg acaggagtgt cgggtaactc catcactacg 1080
gagtattgta cagcccagaa gtcgctcttc caggatcaga acgtcttcga gaaacatgga 1140
ggcttggaag gaatgggtgc cgcattggcc cagggtatgg tcctcgtcat gtccttgtgg 1200
gacgaccact cggccaacat gctctggttg gattccaact accaccacc tgcctcactg 1260
acgacaccgg gtgtcgcacg cggaacttgt gatatctcct cgggagtgcc tgcagacgtc 1320
gaggcgaacc atcccgacgc ctacgtggtc tactcgaaca ttaaggtggg acccatcggt 1380
tcgacattca actccggagg ctcgaaccct ggaggcggaa cgaccactac tacaacgact 1440
cagccgacaa caacaactac cacagcaggc aaccctggag gtacaggtgt ggcccagcac 1500
tacggacagt gtggcggtat cggatggaca ggacctacta cttgtgcatc gccttatacc 1560
tgtcagaaat tgaacgactg gtactcgcag tgtttgtaa                          1599

SEQ ID NO: 92              moltype = AA   length = 532
FEATURE                    Location/Qualifiers
source                     1..532
                           mol_type = protein
                           organism = Aspergillus fumigatus
SEQUENCE: 92
MLASTFSYRM YKTALILAAL LGSGQAQQVG TSQAEVHPSM TWQSCTAGGS CTTNNGKVVI   60
DANWRWVHKV GDYTNCYTGN TWDTTICPDD ATCASNCALE GANYESTYGV TASGNSLRLN  120
FVTTSQQKNI GSRLYMMKDD STYEMFKLLN QEFTFDVDVS NLPCGLNGAL YFVAMDADGG  180
MSKYPTNKAG AKYGTGYCDS QCPRDLKFIN GQANVEGWQP SSNDANAGTG NHGSCCAEMD  240
IWEANSISTA FTPHPCDTPG QVMCTGDACG GTYSSDRYGG TCDPDGCDFN SFRQGNKTFY  300
GPGMTVDTKS KFTVVTQFIT DDGTSSGTLK EIKRFYVQNG KVIPNSESTW TGVSGNSITT  360
EYCTAQKSLF QDQNVFEKHG GLEGMGAALA QGMVLVMSLW DDHSANMLWL DSNYPTTASS  420
TTPGVARGTC DISSGVPADV EANHPDAYVV YSNIKVGPIG STFNSGGSNP GGGTTTTTTT  480
QPTTTTTTAG NPGGTGVAQH YGQCGGIGWT GPTTCASPYT CQKLNDWYSQ CL          532

SEQ ID NO: 93              moltype = DNA   length = 1705
FEATURE                    Location/Qualifiers
source                     1..1705
                           mol_type = genomic DNA
                           organism = Talaromyces byssochlamydoides
SEQUENCE: 93
atgtttcgac gggctctttt cctgtcctct tccgccttcc ttgctgtcaa agcccagcag   60
atcggcacgg tcagtccgga gaaccatccg cccctggcat gggagcagtg cactgcccct  120
gggagttgca cgactgtgaa tggtgcggtc gtccttgatg cgaactggcg ttgggtccac  180
aatgttgggg gatacaccaa ctgctacact ggcaatacct gggacaccac gtactgccct  240
gacgacgtga cctgcgcaga gaattgtgcg ctggatggc cagattacga gggcacctac  300
ggcgtgacca cctcggggcag ctccctgaag tcgatttcg tcaccgggtc taacgtcgga  360
tctcgtctct acctgttgga gaatgattcg acctatcaga tcttcaagct tctgaaccag  420
gaattcacct ttgacgtcga cgtttccaat cttccgtgcg gattaaacgg cgctctgtac  480
cttgttacca tggctgctga cggcggggtg tctcagtacc gaataacaa ggccggcgca  540
gcgtatggaa ccggttattg cgattcccag tgtccaaggg acttgaagtt atcgatggc  600
caggtatgta gagctgtaat cacccatgtt gtgaaatcat tctcctactg acatggtcag  660
tttataggcc aacgttgagg gctggcagcc gtcttcgaac aacgccaata caggtattgg  720
caaccatggc tcctgctgtg cggagatgga tatctgggaa gccaacagca tctccaatgc  780
ggtgactccg cacccatgcg acacacccgg ccagacaatg tgcgagggga cgactgtgg  840
tggcacgtat tccaccaatc gctatgcagg cacctgcgat cctgacggct gcgacttcaa  900
cccctaccgc atgggcaacc attctttcta cggccctggg gagattgtcg atactaccca  960
```

```
gcccttcact gtcgtgacac agttccttac cgatgatggc acggatactg gcactctcag  1020
cgagatcaaa cgcttctacg tccaaaacgg gaaagtcatt cctcagccga actccgacat  1080
tgccggcgtg actggcaact cgatcaccag cgagtttttgc gatgcccaga agacggcttt  1140
cggcgacatt aacaactttg atacacacg cggtctggcc agtatgggag ctgcgctgca   1200
gcagggtatg gttctggtga tgagtctgtg ggacggtagg tccttgggag acacccggac  1260
gttctatatc aaccagaact gccagaactg acgaattaaa acacttttag attacgcggc  1320
aaacatgctg tggttggaca gcatttatcc aacaaatgca tctgctagca ctcctggtgc  1380
tgctcgtgga acctgttcga cgagctccgg tgtcccatcg caagtcgagt cgcagagccc  1440
caacgcctac gtgacgtact ccaacattaa agttggacca atcaactcga ccttcaccac  1500
ttcgggctcg aaccctggag gcggaacgac cactactaca acgactcagc cgacaacaac  1560
aactaccaca gcaggcaacc ctggaggtac aggtgtggcc cagcactacg gacagtgtgg  1620
cggtatcgga tggacaggac ctactacttg tgcatcgcct tatacctgtc agaaattgaa  1680
cgactggtac tcgcagtgtt tgtaa                                         1705
```

```
SEQ ID NO: 94             moltype = AA   length = 521
FEATURE                   Location/Qualifiers
source                    1..521
                          mol_type = protein
                          organism = Talaromyces byssochlamydoides
SEQUENCE: 94
MFRRALFLSS SAFLAVKAQQ IGTVSPENHP PLAWEQCTAP GSCTTVNGAV VLDANWRWVH   60
NVGGYTNCYT GNTWDTTYCP DDVTCAENCA LDGADYEGTY GVTTSGSSLK LDFVTGSNVG   120
SRLYLLENDS TYQIFKLLNQ EFTFDVDVSN LPCGLNGALY LVTMAADGGV SQYPNNKAGA   180
AYGTGYCDSQ CPRDLKFIDG QANVEGWQPS SNNANTGIGN HGSCCAEMDI WEANSISNAV   240
TPHPCDTPGQ TMCEGNDCGG TYSTNRYAGT CDPDGCDFNP YRMGNHSFYG PGEIVDTTQP   300
FTVVTQFLTD DGTDTGTLSE IKRFYVQNGK VIPQPNSDIA GVTGNSITSE FCDAQKTAFG   360
DINNFDTHGG LASMGAALQQ GMVLVMSLWD DYAANMLWLD SIYPTNASAS TPGAARGTCS   420
TSSGVPSQVE SQSPNAYVTY SNIKVGPINS TFTTSGSNPG GGTTTTTTTQ PTTTTTTAGN   480
PGGTGVAQHY GQCGGIGWTG PTTCASPYTC QKLNDWYSQC L                       521
```

```
SEQ ID NO: 95             moltype = DNA   length = 43
FEATURE                   Location/Qualifiers
misc_feature              1..43
                          note = Synthetic Construct DNA Primer
source                    1..43
                          mol_type = other DNA
                          organism = Synthetic Construct
SEQUENCE: 95
gtacaggtgt ggcccagcac tggggacagt gtggcggtat cgg                     43
```

```
SEQ ID NO: 96             moltype = DNA   length = 31
FEATURE                   Location/Qualifiers
misc_feature              1..31
                          note = Synthetic Construct DNA Primer
source                    1..31
                          mol_type = other DNA
                          organism = Synthetic Construct
SEQUENCE: 96
gtgctgggcc acacctgtac ctccagggtt g                                  31
```

```
SEQ ID NO: 97             moltype = DNA   length = 49
FEATURE                   Location/Qualifiers
misc_feature              1..49
                          note = Synthetic Construct DNA Primer
source                    1..49
                          mol_type = other DNA
                          organism = Synthetic Construct
SEQUENCE: 97
atacctgtca gaaattgaac gactggtact cgcagtgttt gtaagcttc               49
```

```
SEQ ID NO: 98             moltype = DNA   length = 32
FEATURE                   Location/Qualifiers
misc_feature              1..32
                          note = Synthetic Construct DNA Primer
source                    1..32
                          mol_type = other DNA
                          organism = Synthetic Construct
SEQUENCE: 98
gtcgttcaat ttctgacagg tataaggcga tg                                 32
```

```
SEQ ID NO: 99             moltype = DNA   length = 23
FEATURE                   Location/Qualifiers
misc_feature              1..23
                          note = Synthetic Construct DNA Primer
source                    1..23
                          mol_type = other DNA
                          organism = Synthetic Construct
SEQUENCE: 99
cctcagccga actccgacat tgc                                           23
```

```
SEQ ID NO: 100        moltype = DNA  length = 23
FEATURE               Location/Qualifiers
misc_feature          1..23
                      note = Synthetic Construct DNA Primer
source                1..23
                      mol_type = other DNA
                      organism = Synthetic Construct
SEQUENCE: 100
gcaatgtcgg agttcggctg agg                                    23
```

CARBOHYDRATE BINDING MODULE VARIANTS AND HYBRID POLYPEPTIDES COMPRISING SAME

CROSS-REFERENCE TO RELATED APPLICATIONS

This application is a US Divisional Application of U.S. Ser. No. 15/508,631, filed Mar. 3, 2017, which is a 35 U.S.C. 371 national application of international application no. PCT/US2015/048620 filed Sep. 4, 2015, which claims priority or the benefit under 35 U.S.C. 119 of U.S. provisional application No. 62/046,344 filed Sep. 5, 2014, the contents of which are fully incorporated herein by reference.

REFERENCE TO A SEQUENCE LISTING

This application contains a Sequence Listing in computer readable form. The contents of the electronic sequence listing created on Sep. 4, 2015, named SQ_ST25.txt and 251 KB in size, is hereby incorporated by reference in its entirety.

BACKGROUND OF THE INVENTION

Field of the Invention

The present invention relates to polypeptides comprising carbohydrate binding module variants, polynucleotides encoding the variants, methods of producing the variants, and methods of using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

Modified carbohydrate binding modules with reduced binding to lignin have been described (WO 2011/097713 A1; Linder et al., 1995, Protein Science 4: 1056-1064; and Linder et al., 1999, FEBS 447: 13-16). Additional variants of carbohydrate binding modules have been described in WO 2012/135719.

Hybrid polypeptides comprising a cellobiohydrolase catalytic domain and a carbohydrate binding module are described in e.g., WO 2010/060056, WO2013/091577, and WO2014/138672.

It would be an advantage in the art to provide polypeptides comprising carbohydrate binding module variants, e.g., cellobiohydrolase variants, with improved properties, such as increased binding affinity, for converting cellulosic materials to monosaccharides, disaccharides, and polysaccharides.

The present invention provides polypeptides comprising carbohydrate binding module variants with improved properties compared to their parents.

SUMMARY OF THE INVENTION

The present invention relates to carbohydrate binding module variants, comprising a substitution at one or more (e.g., several) positions corresponding to positions 5, 13, 31 and 32 of the carbohydrate binding module of SEQ ID NO: 4, wherein the variants have carbohydrate binding activity. In one aspect, a cellulolytic enzyme comprises a carbohydrate binding module variant of the present invention. In some embodiments, the carbohydrate binding module variants have improved binding activity.

The present invention also relates to isolated cellobiohydrolase variants, comprising a substitution at one or more (e.g., several) positions corresponding to positions 483, 491, 509 and 510 of SEQ ID NO: 2, wherein the variants have cellobiohydrolase activity.

The present invention also relates to isolated hybrid polypeptides comprising a carbohydrate binding module variant described herein and a heterologous catalytic domain of a cellulolytic enzyme. In one aspect, the catalytic domain is a cellobiohydrolase catalytic domain.

The present invention also relates to hybrid polypeptides comprising a carbohydrate binding module variant described herein and a heterologous catalytic domain of a cellulolytic enzyme. In one aspect, the catalytic domain is a cellobiohydrolase catalytic domain.

The present invention also relates to isolated polynucleotides encoding the variants and hybrid polypeptides; nucleic acid constructs, vectors, and host cells comprising the polynucleotides; and methods of producing the variants and hybrid polypeptides.

The present invention also relates to methods for degrading or converting a cellulosic material, comprising: treating the cellulosic material with an enzyme composition in the presence of a cellobiohydrolase variant or a hybrid polypeptide of the present invention. In one aspect, the method further comprises recovering the degraded or converted cellulosic material.

The present invention also relates to methods of producing a fermentation product, comprising: (a) saccharifying a cellulosic material with an enzyme composition in the presence of a cellobiohydrolase variant or a hybrid polypeptide of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a cellobiohydrolase variant or a hybrid polypeptide of the present invention. In one aspect, the fermenting of the cellulosic material produces a fermentation product. In another aspect, the method further comprises recovering the fermentation product from the fermentation.

BRIEF DESCRIPTION OF THE FIGURES

FIG. 1 shows the cDNA sequence (SEQ ID NO: 31) and the deduced amino acid sequence (SEQ ID NO: 2) of a

*Trichoderma reesei* cellobiohydrolase I gene. The signal peptide is shown in italics. The carbohydrate binding module is underlined.

Figure 2:
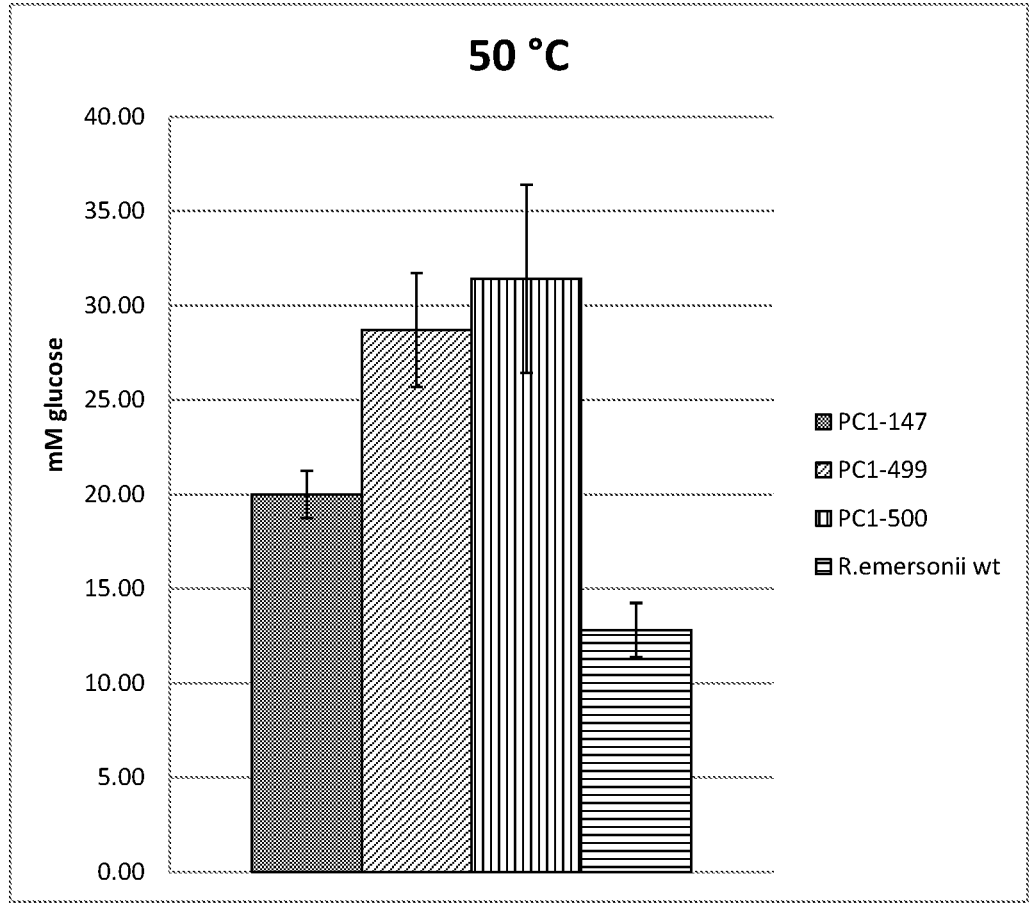

FIG. 2 shows hydrolysis of microcrystalline cellulose by *R. emersonii* wild-type cellobiohydrolase I, and hybrid polypeptides PC1-147, PC1-499 and PC1-500. Values are shown in mM released cellobiose after 24 hours at pH 5 and 50° C.

Figure 3:
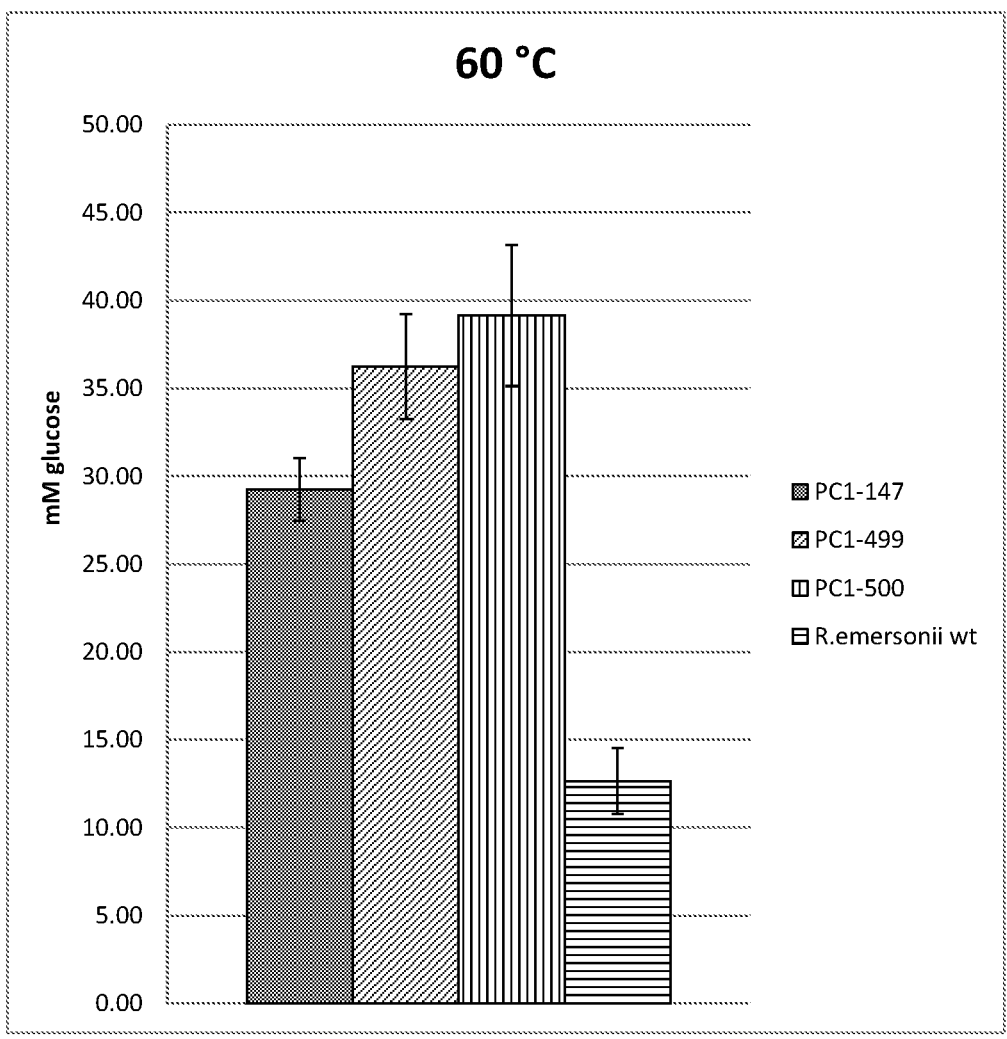

FIG. 3 shows hydrolysis of microcrystalline cellulose by *R. emersonii* wild-type cellobiohydrolase I, and hybrid polypeptides PC1-147, PC1-499 and PC1-500. Values are shown in mM released cellobiose after 24 hours at pH 5 and 60° C.

Figure 4:
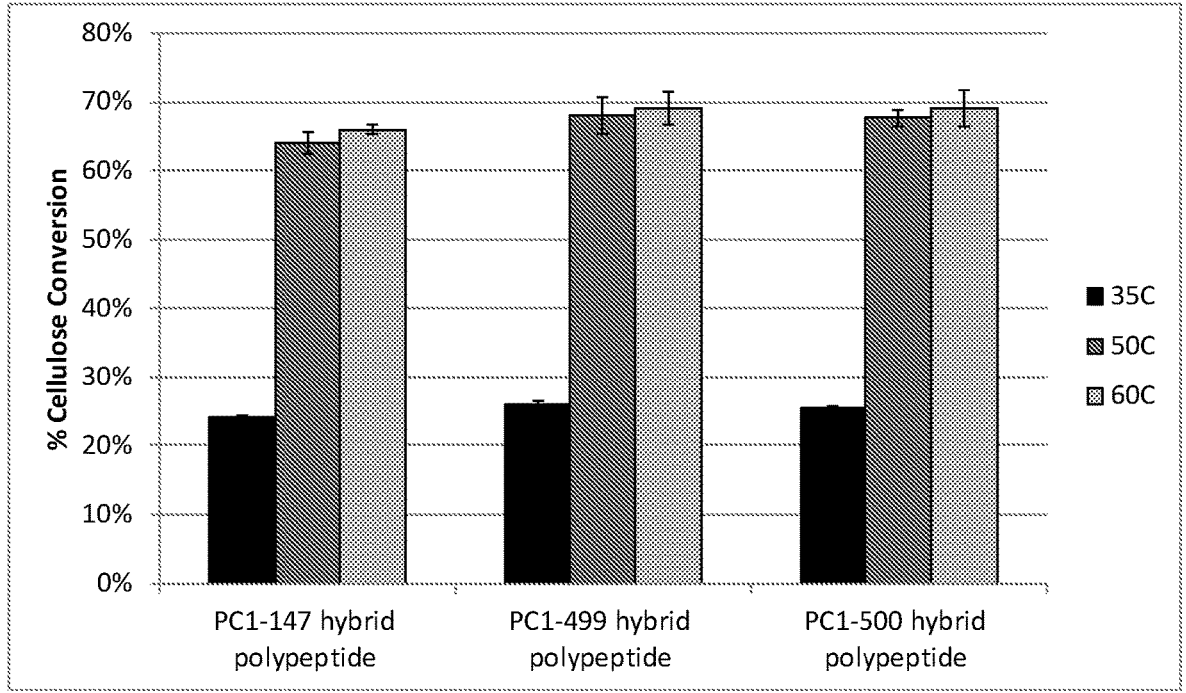

FIG. 4 shows a comparison of percent cellulose conversion of pretreated corn stover at 35° C., 50° C., and 60° C. by enzyme compositions comprising hybrid polypeptides PC1-147, PC1-499 or PC1-500.

Figure 5:
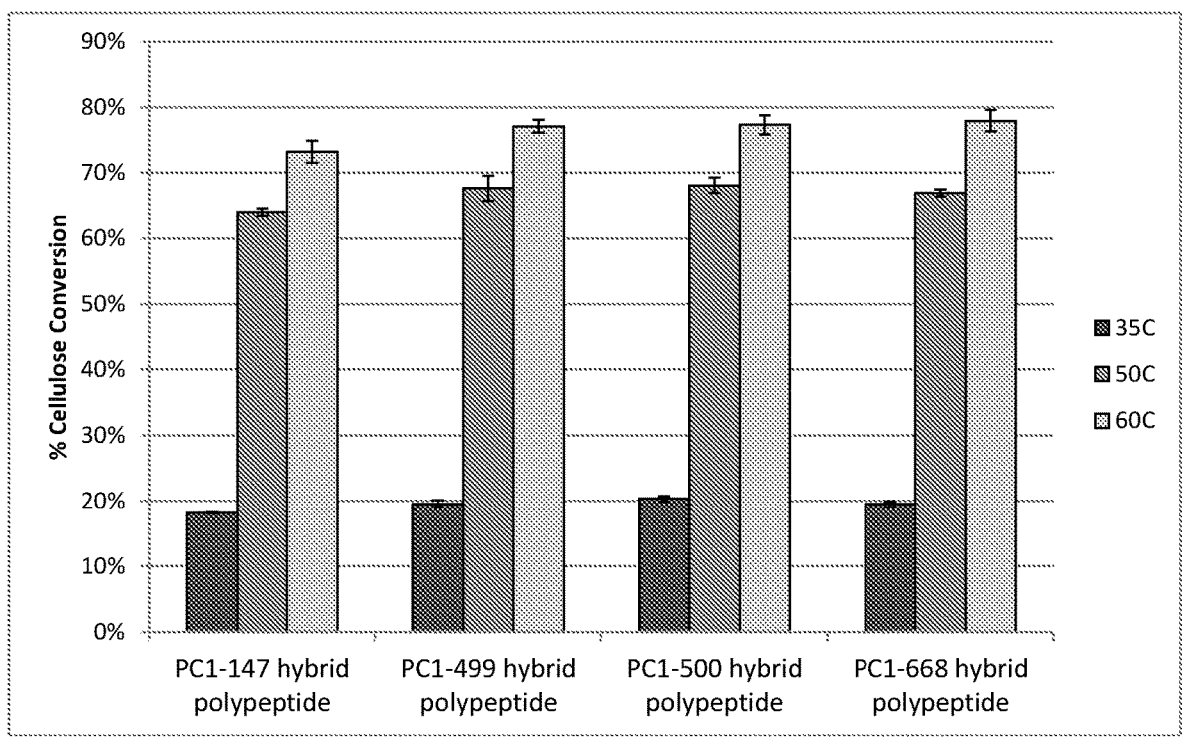

FIG. 5 shows a comparison of percent cellulose conversion of pretreated corn stover at 35° C., 50° C., and 60° C. by enzyme compositions comprising hybrid polypeptides PC1-147, PC1-499, PC1-500, or PC1-668.

Figure 6:
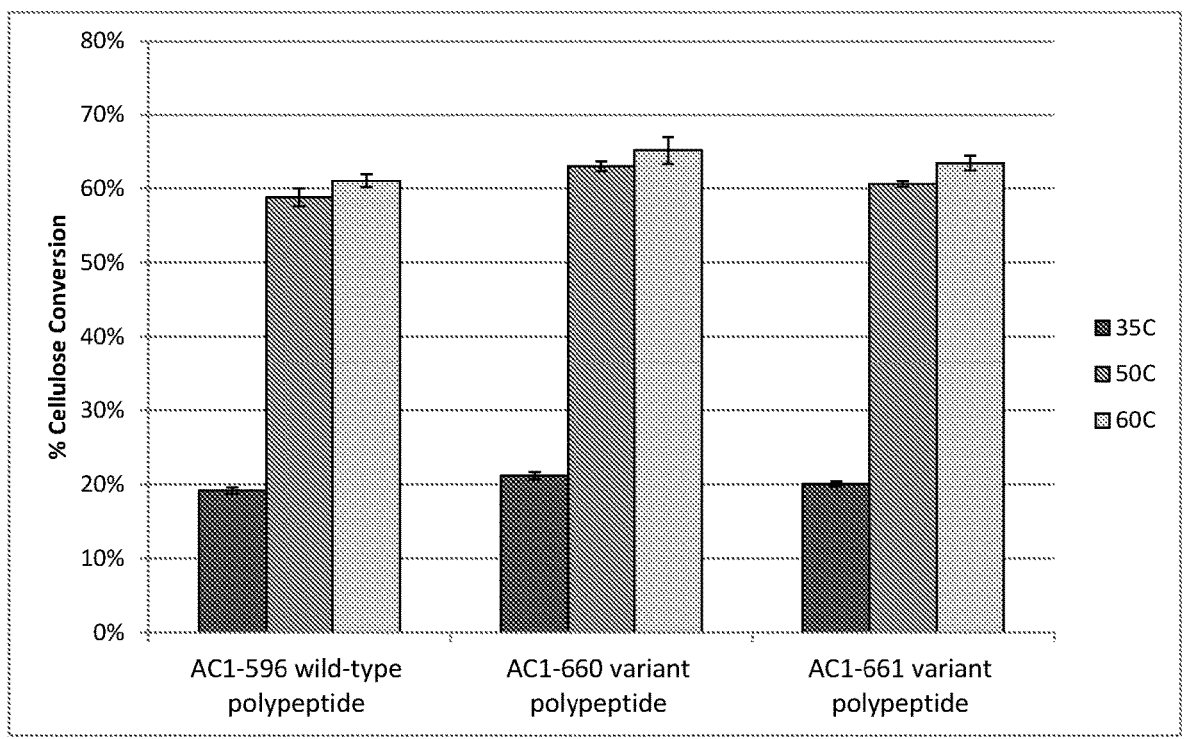

FIG. 6 shows a comparison of percent cellulose conversion of pretreated corn stover at 35° C., 50° C., and 60° C. by enzyme compositions comprising polypeptides AC1-596, AC1-660, or AC1-661.

Figure 7:
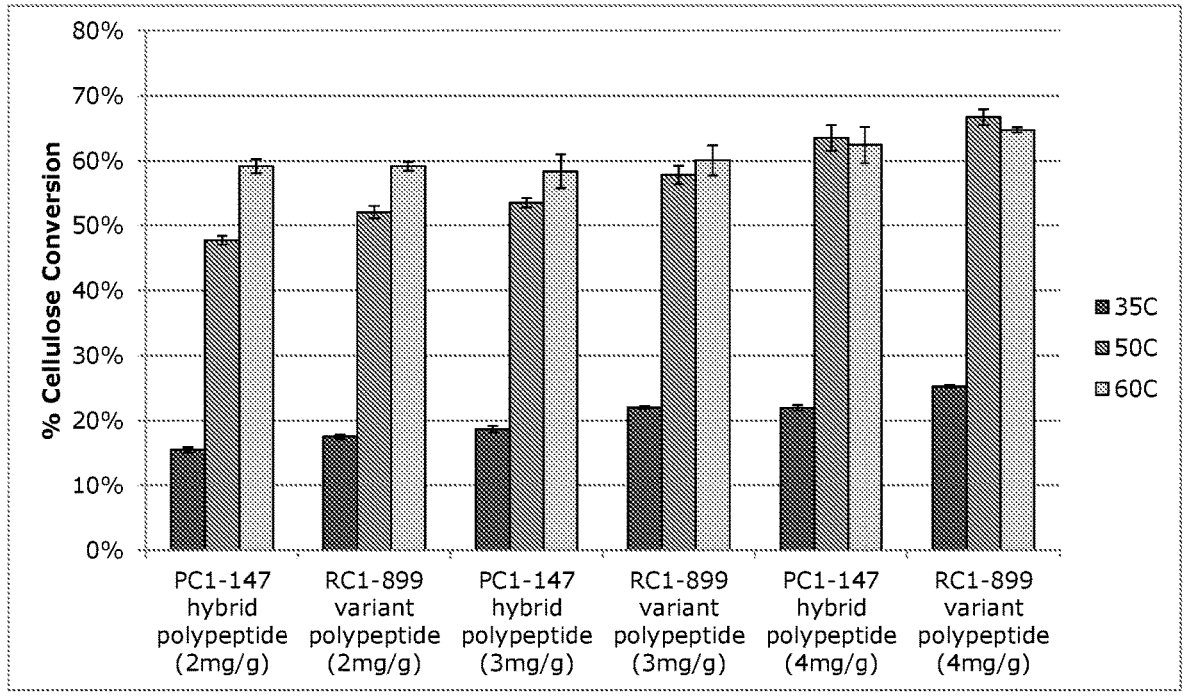

FIG. 7 shows a comparison of percent cellulose conversion of pretreated corn stover at 35° C., 50° C., and 60° C. by enzyme compositions comprising polypeptides PC1-147 or RC1-899.

DEFINITIONS

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, CA, USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C. and a suitable pH, such as 4-9, e.g., 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsvrd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can also be used in the presence of a soluble activating divalent metal cation according to WO 2008/151043 or WO 2012/122518, e.g., manganese or copper.

The AA9 polypeptide can be used in the presence of a dioxy compound, a bicyclic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, J. Basic Microbiol. 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1-4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalase: The term "catalase" means a hydrogen-peroxide:hydrogen-peroxide oxidoreductase (EC 1.11.1.6) that catalyzes the conversion of 2 $H_2O_2$ to $O_2 + 2$ $H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Catalytic domain: The term "catalytic domain" means the region of an enzyme containing the catalytic machinery of the enzyme. In one aspect, the catalytic domain is amino acids 1 to 429 of SEQ ID NO: 30. In another aspect, the catalytic domain is amino acids 1 to 437 of SEQ ID NO: 36. In another aspect, the catalytic domain is amino acids 1 to 440 of SEQ ID NO: 38. In another aspect, the catalytic domain is amino acids 1 to 437 of SEQ ID NO: 40. In another aspect, the catalytic domain is amino acids 1 to 437 of SEQ ID NO: 42. In another aspect, the catalytic domain is amino acids 1 to 438 of SEQ ID NO: 44. In another aspect, the catalytic domain is amino acids 1 to 437 of SEQ ID NO: 46. In another aspect, the catalytic domain is amino acids 1 to 430 of SEQ ID NO: 48. In another aspect, the catalytic domain is amino acids 1 to 433 of SEQ ID NO: 50.

Catalytic domain coding sequence: The term "catalytic domain coding sequence" means a polynucleotide that encodes a catalytic domain having catalytic activity. In one aspect, the catalytic domain coding sequence is nucleotides 52 to 1469 of SEQ ID NO: 29. In another aspect, the catalytic domain coding sequence is nucleotides 52 to 1389 of SEQ ID NO: 31. In another aspect, the catalytic domain coding sequence is nucleotides 52 to 1389 of SEQ ID NO: 32. In another aspect, the catalytic domain coding sequence is nucleotides 79 to 1389 of SEQ ID NO: 35 In another aspect, the catalytic domain coding sequence is nucleotides 52 to 1371 of SEQ ID NO: 37. In another aspect, the catalytic domain coding sequence is nucleotides 55 to 1482 of SEQ ID NO: 39. In another aspect, the catalytic domain coding sequence is nucleotides 76 to 1386 of SEQ ID NO: 41. In another aspect, the catalytic domain is nucleotides 76 to 1386 of SEQ ID NO: 43. In another aspect, the catalytic domain coding sequence is nucleotides 55 to 1504 of SEQ ID NO: 45. In another aspect, the catalytic domain coding sequence is nucleotides 61 to 1350 of SEQ ID NO: 47. In another aspect, the catalytic domain coding sequence is nucleotides 55 to 1353 of SEQ ID NO: 49.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman N21 filter paper as the substrate. The assay was established by the International Union of Pure and Applied Chemistry (IUPAC) (Ghose, 1987, Pure Appl. Chem. 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, CA, USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, sugar cane straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellobiohydrolase activity. In one aspect, a fragment contains at least 425 amino acid residues, e.g., at least 450 amino acid residues or at least 475 amino acid residues of the mature polypeptide of SEQ ID NO: 2. In another aspect, a fragment contains at least 425 amino acid residues, e.g., at least 450 amino acid residues or at least 475 amino acid residues of the mature polypeptide of SEQ ID NO: 6. In another aspect, a fragment contains at least 425 amino acid residues, e.g., at least 450 amino acid residues or at least 475 amino acid residues of the mature polypeptide of SEQ ID NO: 10. In another aspect, a fragment contains at least 425 amino acid residues, e.g., at least 450 amino acid residues or at least 475 amino acid residues of the mature polypeptide of SEQ ID NO: 14. In another aspect, a fragment contains at least 425 amino acid residues, e.g., at least 450 amino acid residues or at least 475 amino acid residues of the mature polypeptide of SEQ ID NO: 18. In another aspect, a fragment contains at least 425 amino acid residues, e.g., at least 450 amino acid residues or at least 475 amino acid residues of the mature polypeptide of SEQ ID NO: 22. In another aspect, a fragment contains at least 425 amino acid residues, e.g., at least 450 amino acid residues or at least 475 amino acid residues of the mature polypeptide of SEQ ID NO: 26.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 40° C., 45°

C., 50° C., 55° C., 60° C., 65° C., 70° C., 75° C., or 80° C., and a suitable pH such as 4-9, e.g., 4.0, 4.5, 5.0, 5.5, 6.0, 6.5, 7.0, 7.5, 8.0, 8.5, or 9.0.

Hemicellulosic material: The term "hemicellulosic material" means any material comprising hemicelluloses. Hemicelluloses include xylan, glucuronoxylan, arabinoxylan, glucomannan, and xyloglucan. These polysaccharides contain many different sugar monomers. Sugar monomers in hemicellulose can include xylose, mannose, galactose, rhamnose, and arabinose. Hemicelluloses contain most of the D-pentose sugars. Xylose is in most cases the sugar monomer present in the largest amount, although in softwoods mannose can be the most abundant sugar. Xylan contains a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono) arabinoxylans, arabinoxylans, and complex heteroxylans. See, for example, Ebringerova et al., 2005, *Adv. Polym. Sci.* 186: 1-67. Hemicellulosic material is also known herein as "xylan-containing material".

Sources for hemicellulosic material are essentially the same as those for cellulosic material described herein.

In the processes of the present invention, any material containing hemicellulose may be used. In a preferred aspect, the hemicellulosic material is lignocellulose.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide in which a region of one polypeptide is fused at the N-terminus or the C-terminus of a region of another (heterologous) polypeptide.

Increased specific performance: The term "increased specific performance" by a variant of the present invention means improved conversion of a cellulosic material to a product, as compared to the same level of conversion by the parent. Increased specific performance is determined per unit protein (e.g., mg protein, or μmole protein). The increased specific performance of the variant relative to the parent can be assessed, for example, under one or more (e.g., several) conditions of pH, temperature, and substrate concentration. In one aspect, the product is glucose. In another aspect, the product is cellobiose. In another aspect, the product is glucose+cellobiose.

In one aspect, the condition is pH. For example, the pH can be any pH in the range of 3 to 7, e.g., 3.0, 3.5, 4.0, 4.5, 5.0, 5.5, 6.0, 6.5, or 7.0 (or in between). Any suitable buffer for achieving the desired pH can be used.

In another aspect, the condition is temperature. For example, the temperature can be any temperature in the range of 25° C. to 90° C., e.g., 25, 30, 35, 40, 45, 50, 55, 60, 65, 70, 75, 80, 85, or 90° C. (or in between).

In another aspect, the condition is substrate concentration. Any cellulosic material defined herein can be used as the substrate. In one aspect, the substrate concentration is measured as the dry solids content. The dry solids content is preferably in the range of about 1 to about 50 wt %, e.g., about 5 to about 45 wt %, about 10 to about 40 wt %, or about 20 to about 30 wt %. In another aspect, the substrate concentration is measured as the insoluble glucan content. The insoluble glucan content is preferably in the range of about 2.5 to about 25 wt %, e.g., about 5 to about 20 wt % or about 10 to about 15 wt %.

In another aspect, a combination of two or more (e.g., several) of the above conditions are used to determine the increased specific performance of the variant relative to the parent, such as any temperature in the range of 25° C. to 90° C., e.g., 25, 30, 35, 40, 45, 50, 55, 60, 65, 70, 75, 80, 85, or 90° C. (or in between) at a pH in the range of 3 to 7, e.g., 3.0, 3.5, 4.0, 4.5, 5.0, 5.5, 6.0, 6.5, or 7.0 (or in between).

The increased specific performance of the variant relative to the parent can be determined using any enzyme assay known in the art for cellobiohydrolases as described herein. Alternatively, the increased specific performance of the variant relative to the parent can be determined using the assays described in Examples 9 and 12.

In another aspect, the specific performance of the variant is at least 1.01-fold, e.g., at least 1.02-fold, at least 1.03-fold, at least 1.04-fold, at least 1.05-fold, at least 1.06-fold, at least 1.07-fold, at least 1.08-fold, at least 1.09-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 5-fold, at least 10-fold, at least 15-fold, at least 20-fold, at least 25-fold, and at least 50-fold higher than the specific performance of the parent.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). Any of the carbohydrate binding module variants, cellobiohydrolase variants, or hybrid polypeptides described herein may be in isolated form.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 514 of SEQ ID NO: 2, amino acids 19 to 525 of SEQ ID NO: 6, amino acids 19 to 530 of SEQ ID NO: 10, amino acids 26 to 537 of SEQ ID NO: 14, amino acids 27 to 532 of SEQ ID NO: 18, amino acids 18 to 526 of SEQ ID NO: 22, amino acids 18 to 525 of SEQ ID NO: 26, amino acids 19 to 519 of SEQ ID NO: 61, amino acids 19 to 519 of SEQ ID NO: 63, amino acids 19 to 519 of SEQ ID NO: 73, amino acids 27 to 532 of SEQ ID NO: 78, amino acids 27 to 532 of SEQ ID NO: 90, amino acids 27 to 532 of SEQ ID NO: 92, amino acids 19 to 521 of SEQ ID NO: 94 based on the SignalP program (Nielsen et al., 1997, *Protein Engineering* 10: 1-6) that predicts amino acids 1 to 17 of SEQ ID NO: 2, amino acids 1 to 18 of SEQ ID NO: 6, amino acids 1 to 18 of SEQ ID NO: 10, amino acids 1 to 25 of SEQ ID NO: 14, amino acids 1 to 26 of SEQ ID NO: 18, amino acids 1 to 17 of SEQ ID NO: 22, and amino acids 1 to 17 of SEQ ID NO: 26, amino acids 1 to 18 of SEQ ID NO: 61, amino acids 1 to 18 of SEQ ID NO: 63, amino acids 1 to 18 of SEQ ID NO: 73, amino acids 1 to 26 of SEQ ID NO: 78, amino acids 1 to 26 of SEQ ID NO: 90, amino acids 1 to 26 of SEQ ID NO: 92, amino acids 1 to 18 of SEQ ID NO: 94, respectively, are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellobiohydrolase activity. In one aspect, the mature polypeptide coding sequence is nucleotides 52 to 1542 of SEQ ID NO: 1, nucleotides 55 to 1635 of SEQ ID NO: 5, nucleotides 55 to 1590 of SEQ ID NO: 9, nucleotides 76 to 1614 of SEQ ID NO: 13, nucleotides 79 to 1596 of SEQ ID NO: 17, nucleotides 52 to 1578 of SEQ ID NO: 21, and nucleotides 52 to 1575 of SEQ ID NO: 25, or the genomic DNA or cDNA sequence thereof, based on the SignalP program (Nielsen et al., supra) that predicts nucleotides 1 to 51 of SEQ ID NO: 1, nucleotides 1 to 54 of SEQ ID NO: 5, nucleotides 1 to 54 of SEQ ID NO: 9, nucleotides 1 to 75 of SEQ ID NO: 13, nucleotides 1 to 78 of SEQ ID NO: 17, nucleotides 1 to 51 of SEQ ID NO: 21, and nucleotides 1 to 51 of SEQ ID NO: 25, respectively, encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent cellobiohydrolase: The term "parent cellobiohydrolase" means a cellobiohydrolase to which an alteration is made to produce the enzyme variants of the present invention. The parent may be a naturally occurring (wild-type) polypeptide or a variant or fragment thereof. The parent cellobiohydrolase may include a carbohydrate binding module.

Parent carbohydrate binding module: The term "parent carbohydrate binding module" means a carbohydrate binding module to which an alteration is made to produce the carbohydrate binding module variants of the present invention. The parent may be a naturally occurring (wild-type) polypeptide or a variant or fragment thereof.

Pretreated cellulosic or hemicellulosic material: The term "pretreated cellulosic or hemicellulosic material" means a cellulosic or hemicellulosic material derived from biomass by treatment with heat and dilute sulfuric acid, alkaline pretreatment, neutral pretreatment, or any pretreatment known in the art.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

$$(\text{Identical Deoxyribonucleotides} \times 100)/(\text{Length of Alignment} - \text{Total Number of Gaps in Alignment})$$

Subsequence: The term "subsequence" means a polynucleotide having one or more (e.g., several) nucleotides absent from the 5' and/or 3' end of a mature polypeptide coding sequence; wherein the subsequence encodes a fragment having cellobiohydrolase activity. In one aspect, a subsequence contains at least 1275 nucleotides, e.g., at least 1350 nucleotides or at least 1425 nucleotides of the mature polypeptide coding sequence of SEQ ID NO: 1. In another aspect, a subsequence contains at least 1275 nucleotides, e.g., at least 1350 nucleotides or at least 1425 nucleotides of the mature polypeptide coding sequence of SEQ ID NO: 5. In another aspect, a subsequence contains at least 1275 nucleotides, e.g., at least 1350 nucleotides or at least 1425 nucleotides of the mature polypeptide coding sequence of SEQ ID NO: 9. In another aspect, a subsequence contains at least 1275 nucleotides, e.g., at least 1350 nucleotides or at least 1425 nucleotides of the mature polypeptide coding sequence of SEQ ID NO: 13. In another aspect, a subsequence contains at least 1275 nucleotides, e.g., at least 1350 nucleotides or at least 1425 nucleotides of the mature polypeptide coding sequence of SEQ ID NO: 17. In another aspect, a subsequence contains at least 1275 nucleotides, e.g., at least 1350 nucleotides or at least 1425 nucleotides of the mature polypeptide coding sequence of SEQ ID NO: 21. In another aspect, a subsequence contains at least 1275 nucleotides, e.g., at least 1350 nucleotides or at least 1425 nucleotides of the mature polypeptide coding sequence of SEQ ID NO: 25.

Variant: The term "variant" means a polypeptide having cellobiohydrolase activity or a carbohydrate binding module comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

A cellobiohydrolase variant of the present invention has at least 20%, e.g., at least 40%, at least 50%, at least 60%, at least 70%, at least 80%, at least 90%, at least 95%, or at least 100% of the cellobiohydrolase activity of the mature polypeptide of SEQ ID NO: 2, SEQ ID NO: 6, SEQ ID NO: 10, SEQ ID NO: 14, SEQ ID NO: 18, SEQ ID NO: 22, or SEQ ID NO: 26. A carbohydrate binding module variant of the present invention has at least 20%, e.g., at least 40%, at least 50%, at least 60%, at least 70%, at least 80%, at least 90%, at least 95%, or at least 100% of the carbohydrate binding activity of SEQ ID NO: 4, SEQ ID NO: 8, SEQ ID NO: 12, SEQ ID NO: 16, SEQ ID NO: 20, SEQ ID NO: 24, or SEQ ID NO: 28.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Wild-type cellobiohydrolase: The term "wild-type" cellobiohydrolase means a cellobiohydrolase expressed by a naturally occurring microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrimann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, MO, USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

The present invention relates to carbohydrate binding module variants, comprising a substitution at one or more (e.g., several) positions corresponding to positions 5, 13, 31 and 32 of the carbohydrate binding module of SEQ ID NO: 4, wherein the variants have carbohydrate binding activity. In one aspect, a cellulolytic enzyme comprises a carbohydrate binding module variant of the present invention (e.g., a hybrid polypeptide).

The present invention also relates to isolated cellobiohydrolase variants, comprising a substitution at one or more (e.g., several) positions corresponding to positions 483, 491, 509 and 510 of SEQ ID NO: 2, wherein the variants have cellobiohydrolase activity.

Conventions for Designation of Variants

For purposes of the present invention, the polypeptide sequence disclosed in SEQ ID NO: 2 or the carbohydrate binding module (CBM) disclosed in SEQ ID NO: 4 is used to determine the corresponding amino acid residue in another cellobiohydrolase or CBM, respectively. The amino acid sequence of another cellobiohydrolase or CBM is aligned with SEQ ID NO: 2 or SEQ ID NO: 4, respectively, and based on the alignment, the amino acid position number corresponding to any amino acid residue in the polypeptide disclosed in SEQ ID NO: 2 or the CBM disclosed in SEQ ID NO: 4 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another cellobiohydrolase or CBM can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 2 or the other CBM has diverged from SEQ ID NO: 4 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of an unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Carbohydrate Binding Module Variants

The present invention relates to variants of a parent carbohydrate binding module comprising a substitution at one or more (e.g., several) positions corresponding to positions 5, 13, 31 and 32 of the carbohydrate binding module of SEQ ID NO: 4, wherein the variant has carbohydrate binding activity.

In one aspect, the carbohydrate binding module variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent carbohydrate binding module.

In another aspect, the carbohydrate binding module variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4, SEQ ID NO: 8, SEQ ID NO: 12, SEQ ID NO: 16, SEQ ID NO: 20, SEQ ID NO: 24, or SEQ ID NO: 28.

In one aspect, the number of substitutions in the carbohydrate binding module variants of the present invention is 1-4, such as 1, 2, 3, or 4 substitutions.

In one aspect, the carbohydrate binding module variant comprises or consists of a substitution at a position corresponding to position 5 of SEQ ID NO: 4. In one embodiment, the amino acid at a position corresponding to position 5 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 5 of SEQ ID NO: 4 is substituted with Trp. In another embodiment, the amino acid at a position corresponding to position 5 of SEQ ID NO: 4 is Tyr substituted with Trp (e.g., Y5W of SEQ ID NO: 4).

In another aspect, the carbohydrate binding module variant comprises or consists of a substitution at a position corresponding to position 13 of SEQ ID NO: 4. In one embodiment, the amino acid at a position corresponding to position 13 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 13 of SEQ ID NO: 4 is substituted with Trp. In another embodiment, the amino acid at a position corresponding to position 13 of SEQ ID NO: 4 is Tyr substituted with Trp (e.g., Y13W of SEQ ID NO: 4).

In another aspect, the carbohydrate binding module variant comprises or consists of a substitution at a position corresponding to position 31 of SEQ ID NO: 4. In one embodiment, the amino acid at a position corresponding to position 31 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 31 of SEQ ID NO: 4 is substituted with Trp. In another embodiment, the amino acid at a position corresponding to position 31 of SEQ ID NO: 4 is Tyr substituted with Trp (e.g., Y31W of SEQ ID NO: 4).

In another aspect, the carbohydrate binding module variant comprises or consists of a substitution at a position corresponding to position 32 of SEQ ID NO: 4. In one embodiment, the amino acid at a position corresponding to position 32 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 32 of SEQ ID NO: 4 is substituted with Trp. In another embodiment, the amino acid at a position corresponding to position 32 of SEQ ID NO: 4 is Tyr substituted with Trp (e.g., Y32W of SEQ ID NO: 4).

In another aspect, the carbohydrate binding module variant comprises or consists of a substitution at two positions corresponding to positions 5, 13, 31 and 32 of SEQ ID NO: 4, such as those described above. In one embodiment, the carbohydrate binding module variant comprises or consists of a substitution at positions corresponding to positions 5 and 13 (e.g., substituted with Trp at positions corresponding to positions 5 and 13, such as Y5W and/or Y13W). In another embodiment, the carbohydrate binding module variant comprises or consists of a substitution at positions corresponding to positions 5 and 31 (e.g., substituted with Trp at positions corresponding to positions 5 and 31, such as Y5W and/or Y31W). In another embodiment, the carbohydrate binding module variant comprises or consists of a substitution at positions corresponding to positions 5 and 32 (e.g., substituted with Trp at positions corresponding to positions 5 and 32, such as Y5W and/or Y32W). In another embodiment, the carbohydrate binding module variant comprises or consists of a substitution at positions corresponding to positions 13 and 31 (e.g., substituted with Trp at positions corresponding to positions 13 and 31, such as Y13W and/or Y31W). In another embodiment, the carbohydrate binding module variant comprises or consists of a substitution at positions corresponding to positions 13 and 32 (e.g., substituted with Trp at positions corresponding to positions 13 and 32, such as Y13W and/or Y32W). In another embodiment, the carbohydrate binding module variant comprises or consists of a substitution at positions corresponding to positions 31 and 32 (e.g., substituted with Trp at positions corresponding to positions 31 and 32, such as Y31W and/or Y32W).

In another aspect, the carbohydrate binding module variant comprises or consists of a substitution at three positions corresponding to positions 5, 13, 31 and 32 of SEQ ID NO: 4, such as those described above. In one embodiment, the carbohydrate binding module variant comprises or consists of a substitution at positions corresponding to positions 5, 13, and 31 (e.g., substituted with Trp at positions corresponding to positions 5, 13, and 31, such as Y5W, Y13W, and/or Y31W). In another embodiment, the carbohydrate binding module variant comprises or consists of a substitution at positions corresponding to positions 5, 13, and 32 (e.g., substituted with Trp at positions corresponding to positions 5, 13, and 32, such as Y5W, Y13W, and/or Y32W). In another embodiment, the carbohydrate binding module variant comprises or consists of a substitution at positions corresponding to positions 5, 31, and 32 (e.g., substituted with Trp at positions corresponding to positions 5, 31, and 32, such as Y5W, Y31W, and/or Y32W). In another embodiment, the carbohydrate binding module variant comprises or consists of a substitution at positions corresponding to positions 13, 31, and 32 (e.g., substituted with Trp at positions corresponding to positions 13, 31, and 32, such as Y13W, Y31W, and/or Y32W).

In another aspect, the carbohydrate binding module variant comprises or consists of a substitution at all four positions corresponding to positions 5, 13, 31 and 32 of SEQ ID NO: 4, such as those described above. In one embodiment, the carbohydrate binding module variant comprises or consists of a Trp substitution at one or more positions corresponding to positions 5, 13, 31 and 32, such as Y5W, Y13W, Y31W and/or Y32W).

The carbohydrate binding module variants may further comprise a substitution, a deletion, and/or an insertion at one or more (e.g., several) other positions, such as one or more (e.g., several) substitutions at positions corresponding to positions disclosed in WO 2012/135719, which is incorporated herein by reference. For example, in one aspect, the carbohydrate binding module variant further comprises a substitution at one or more (e.g., several) positions corresponding to positions 4, 6, and 29 of SEQ ID NO: 4. In another aspect, the carbohydrate binding module variant further comprises a substitution at two positions corresponding to any of positions 4, 6, and 29. In another aspect, the carbohydrate binding module variant further comprises a substitution at each position corresponding to positions 4, 6, and 29.

In another aspect, the carbohydrate binding module variant further comprises or consists of a substitution at a position corresponding to position 4. In another aspect, the amino acid at a position corresponding to position 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Leu, Lys, Phe, or Trp.

In another aspect, the carbohydrate binding module variant further comprises or consists of the substitution H4L of SEQ ID NO: 4. In another aspect, the carbohydrate binding module variant further comprises or consists of the substitution H4K of SEQ ID NO: 4. In another aspect, the carbohydrate binding module variant further comprises or consists of the substitution H4E of SEQ ID NO: 4. In another aspect, the carbohydrate binding module variant further comprises or consists of the substitution H4F of SEQ ID NO: 4. In another aspect, the carbohydrate binding module variant further comprises or consists of the substitution H4W of SEQ ID NO: 4.

In another aspect, the carbohydrate binding module variant further comprises or consists of a substitution at a position corresponding to position 6. In another aspect, the amino acid at a position corresponding to position 6 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the carbohydrate binding module variant further comprises or consists of the substitution G6A of SEQ ID NO: 4.

In another aspect, the carbohydrate binding module variant further comprises or consists of a substitution at a position corresponding to position 29. In another aspect, the amino acid at a position corresponding to position 29 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the carbohydrate binding module variant further comprises or consists of the substitution N29D of SEQ ID NO: 4.

In another aspect, the carbohydrate binding module variant further comprises or consists of a substitution at positions corresponding to positions 4 and 6, such as those described above.

In another aspect, the carbohydrate binding module variant further comprises or consists of substitutions at positions corresponding to positions 4 and 29, such as those described above. In another aspect, the carbohydrate binding module variant further comprises or consists of substitutions at positions corresponding to positions 6 and 29, such as those described above.

In another aspect, the carbohydrate binding module variant further comprises or consists of substitutions at positions corresponding to positions 4, 6, and 29, such as those described above.

In another aspect, the carbohydrate binding module variant further comprises or consists of one or more (e.g., several) substitutions selected from the group consisting of H4L,K,E,F,W, G6A, and N29D or the one or more (e.g., several) substitutions selected from the group consisting of H4L,K,E,F,W, G6A, and N29D corresponding to SEQ ID NO: 4 in other cellulose binding modules described herein.

In another aspect, the carbohydrate binding module variant further comprises or consists of the substitutions H4L+ G6A of SEQ ID NO: 4.

In another aspect, the carbohydrate binding module variant further comprises or consists of the substitutions H4K+ G6A of SEQ ID NO: 4.

In another aspect, the carbohydrate binding module variant further comprises or consists of the substitutions H4E+ G6A of SEQ ID NO: 4.

In another aspect, the carbohydrate binding module variant further comprises or consists of the substitutions H4F+ G6A of SEQ ID NO: 4.

In another aspect, the carbohydrate binding module variant further comprises or consists of the substitutions H4W+ G6A of SEQ ID NO: 4.

In another aspect, the carbohydrate binding module variant further comprises or consists of the substitutions H4L+ N29D of SEQ ID NO: 4.

In another aspect, the carbohydrate binding module variant further comprises or consists of the substitutions H4K+ N29D of SEQ ID NO: 4.

In another aspect, the carbohydrate binding module variant further comprises or consists of the substitutions H4E+ N29D of SEQ ID NO: 4.

In another aspect, the carbohydrate binding module variant further comprises or consists of the substitutions H4F+ N29D of SEQ ID NO: 4.

In another aspect, the carbohydrate binding module variant further comprises or consists of the substitutions H4W+ N29D of SEQ ID NO: 4.

In another aspect, the carbohydrate binding module variant further comprises or consists of the substitutions G6A+ N29D of SEQ ID NO: 4.

In another aspect, the carbohydrate binding module variant further comprises or consists of the substitutions H4L+ G6A+N29D of SEQ ID NO: 4.

In another aspect, the carbohydrate binding module variant further comprises or consists of the substitutions H4K+ G6A+N29D of SEQ ID NO: 4.

In another aspect, the carbohydrate binding module variant further comprises or consists of the substitutions H4E+ G6A+N29D of SEQ ID NO: 4.

In another aspect, the carbohydrate binding module variant further comprises or consists of the substitutions H4F+ G6A+N29D of SEQ ID NO: 4.

In another aspect, the carbohydrate binding module variant further comprises or consists of the substitutions H4W+ G6A+N29D of SEQ ID NO: 4.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding module.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/ Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In some aspects, the carbohydrate binding module variants may consist of 28 to 36 amino acids, inclusive, e.g., 28, 29, 30, 31, 32, 33, 34, 35, or 36 amino acids.

As described in more detail below, the present invention also relates to a polypeptide having cellulolytic activity, comprising a carbohydrate binding module variant as described above. In one aspect, the polypeptide is derived from a "wild-type" cellulolytic enzyme (such as a "wild-type" cellobiohydrolase) having a carbohydrate binding module, wherein the carbohydrate binding module comprises a substitution at one or more (e.g., several) positions corresponding to positions 5, 13, 31 and 32 of SEQ ID NO: 4. In one aspect, a carbohydrate binding module variant of the present invention may be fused to a polypeptide lacking a carbohydrate binding module. In another aspect, a carbohydrate binding module contained in a polypeptide may be replaced with a carbohydrate binding module variant of the present invention. In another aspect, the polypeptide is a cellulolytic enzyme selected from the group consisting of an endoglucanase, a cellobiohydrolase, and a GH61 polypeptide. In one embodiment, the cellulolytic enzyme is an endoglucanase. In another embodiment, the cellulolytic enzyme is a cellobiohydrolase. In another embodiment, the cellulolytic enzyme is a GH61 polypeptide.

In some aspects, the carbohydrate binding module variants have improved binding activity. In some embodiments, carbohydrate binding module variants do not have decreased binding activity compared to the parent. In some embodiments, the carbohydrate binding module variant has at least 1.01-fold, e.g., at least 1.02-fold, at least 1.03-fold, at least 1.04-fold, at least 1.05-fold, at least 1.06-fold, at least 1.07-fold, at least 1.08-fold, at least 1.09-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 5-fold, at least 10-fold, at least 15-fold, at least 20-fold, at least 25-fold, and at least 50-fold higher binding activity compared to the parent.

Cellobiohydrolase Variants

The present invention also relates to variants of a parent cellobiohydrolase comprising a carbohydrate binding module wherein the carbohydrate binding module comprises a substitution at one or more (e.g., several) positions corresponding to positions 5, 13, 31 and 32 of SEQ ID NO: 4. For example, in one aspect is a variant of a parent cellobiohydrolase comprising a substitution at one or more (e.g., several) positions corresponding to positions 483, 491, 509 and 510 of SEQ ID NO: 2, wherein the variant has cellobiohydrolase activity.

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent cellobiohydrolase.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

In one aspect, the number of substitutions in the variants of the present invention is 1-3, such as 1, 2, or 3 substitutions.

In another aspect, the variant comprises or consists of a substitution at a position corresponding to position 483 of SEQ ID NO: 2. In one embodiment, the amino acid at a position corresponding to position 483 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 483 of SEQ ID NO: 2 is substituted with Trp. In another embodiment, the amino acid at a position corresponding to position 483 of SEQ ID NO: 2 is Tyr substituted with Trp (e.g., Y483W of SEQ ID NO: 4).

In another aspect, the variant comprises or consists of a substitution at a position corresponding to position 491 of SEQ ID NO: 2. In one embodiment, the amino acid at a position corresponding to position 491 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 491 of SEQ ID NO: 2 is substituted with Trp. In another embodiment, the amino acid at a position corresponding to position 491 of SEQ ID NO: 2 is Tyr substituted with Trp (e.g., Y491W of SEQ ID NO: 4).

In another aspect, the variant comprises or consists of a substitution at a position corresponding to position 509 of SEQ ID NO: 2. In one embodiment, the amino acid at a position corresponding to position 509 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 509 of SEQ ID NO: 2 is substituted with Trp. In another embodiment, the amino acid at a position corresponding to position 509 of SEQ ID NO: 2 is Tyr substituted with Trp (e.g., Y509W of SEQ ID NO: 4).

In another aspect, the variant comprises or consists of a substitution at a position corresponding to position 510 of SEQ ID NO: 2. In one embodiment, the amino acid at a position corresponding to position 510 is substituted with Ala, Arg, Asn, Asp, Cys, Gin, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 510 of SEQ ID NO: 2 is substituted with Trp. In another embodiment, the amino acid at a position corresponding to position 510 of SEQ ID NO: 2 is Tyr substituted with Trp (e.g., Y510W of SEQ ID NO: 4).

In another aspect, the variant comprises or consists of a substitution at two positions corresponding to positions 483, 491, 509 and 510 of SEQ ID NO: 2, such as those described above. In one embodiment, the variant comprises or consists of a substitution at positions corresponding to positions 483 and 491 (e.g., substituted with Trp at positions corresponding to positions 483 and 491, such as Y483W and/or Y491W). In another embodiment, the variant comprises or consists of a substitution at positions corresponding to positions 483 and 509 (e.g., substituted with Trp at positions corresponding to positions 483 and 509, such as Y483W and/or Y509W). In another embodiment, the variant comprises or consists of a substitution at positions corresponding to positions 483 and 510 (e.g., substituted with Trp at positions corresponding to positions 483 and 510, such as Y483W and/or Y510W). In another embodiment, the variant comprises or consists of a substitution at positions corresponding to positions 491 and 509 (e.g., substituted with Trp at positions corresponding to positions 491 and 509, such as Y491W and/or Y509W). In another embodiment, the variant comprises or consists of a substitution at positions corresponding to positions 491 and 510 (e.g., substituted with Trp at positions corresponding to positions 491 and 510, such as Y491W and/or Y32W). In another embodiment, the variant comprises or consists of a substitution at positions corresponding to positions 509 and 510 (e.g., substituted with Trp at positions corresponding to positions 509 and 510, such as Y509W and/or Y510W).

In another aspect, the variant comprises or consists of a substitution at three positions corresponding to positions 483, 491, 509 and 32 of SEQ ID NO: 2, such as those described above. In one embodiment, the variant comprises or consists of a substitution at positions corresponding to positions 483, 491, and 509 (e.g., substituted with Trp at positions corresponding to positions 483, 491, and 509, such as Y483W, Y491W, and/or Y509W). In another embodiment, the variant comprises or consists of a substitution at positions corresponding to positions 483, 491, and 510 (e.g., substituted with Trp at positions corresponding to positions 483, 491, and 510, such as Y5W, Y491W, and/or Y510W). In another embodiment, the variant comprises or consists of a substitution at positions corresponding to positions 483, 509, and 510 (e.g., substituted with Trp at positions corresponding to positions 483, 509, and 510, such as Y483W, Y509W, and/or Y510W). In another embodiment, the variant comprises or consists of a substitution at positions corresponding to positions 491, 509, and 510 (e.g., substituted with Trp at positions corresponding to positions 491, 509, and 510, such as Y491W, Y509W, and/or Y510W).

In another aspect, the variant comprises or consists of a substitution at all four positions corresponding to positions 483, 491, 509 and 510 of SEQ ID NO: 2, such as those described above. In one embodiment, the variant comprises or consists of a Trp substitution at one or more positions corresponding to positions 483, 491, 509 and 510, such as Y483W, Y491W, Y509W and/or Y510W).

In one aspect, the variant comprises or consists of SEQ ID NO: 90 or SEQ ID NO: 92, or the mature polypeptide sequence thereof.

The cellobiohydrolase variants may further comprise a substitution, a deletion, and/or an insertion at one or more (e.g., several) other positions, such as an alteration at one or more (e.g., several) positions corresponding to positions disclosed in PCT/US2014/022068, WO 2011/050037, WO 2005/028636, WO 2005/001065, WO 2004/016760, and U.S. Pat. No. 7,375,197, which are incorporated herein in their entireties.

For example, in one aspect, a variant comprises an alteration at one or more positions corresponding to positions 214, 215, 216, and 217 of SEQ ID NO: 2 (corresponding to positions 197, 198, 199, and 200 of the mature polypeptide sequence), wherein the alteration at the one or more positions corresponding to positions 214, 215, and 217 is a substitution and the alteration at the position corresponding to position 216 is a deletion. In another aspect, a variant comprises an alteration at two positions corresponding to any of positions 214, 215, 216, and 217 of SEQ ID NO: 2, wherein the alteration at the one or more positions corresponding to positions 214, 215, and 217 is a substitution and the alteration at the position corresponding to position 216 is a deletion. In another aspect, a variant comprises an alteration at three positions corresponding to any of positions 214, 215, 216, and 217 of SEQ ID NO: 2, wherein the alteration at the one or more positions corresponding to positions 214, 215, and 217 is a substitution and the alteration at the position corresponding to position 216 is a deletion. In another aspect, a variant comprises a substitution at each position corresponding to positions 214, 215, and 217 and a deletion at a position corresponding to position 216.

In another aspect, the variant comprises or consists of a substitution at a position corresponding to position 214. In another aspect, the amino acid at a position corresponding to position 214 is substituted with Ala, Arg, Asn, Asp, Cys, Gin, Glu, Gly, His, Ile, Leu, Lys, Met, Phe, Pro, Ser, Thr, Trp, Tyr, or Val, preferably with Ala. In another aspect, the variant comprises or consists of the substitution N214A of SEQ ID NO: 2.

In another aspect, the variant comprises or consists of a substitution at a position corresponding to position 215. In another aspect, the amino acid at a position corresponding to position 215 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution N215A of SEQ ID NO: 2.

In another aspect, the variant comprises or consists of a deletion at a position corresponding to position 216. In another aspect, the amino acid at a position corresponding to position 216 is Ala, Arg, Asn, Asp, Cys, Gin, Glu, Gly, His, Ile, Leu, Lys, Met, Phe, Pro, Ser, Thr, Trp, Tyr, or Val, preferably Ala. In another aspect, the variant comprises or consists of the deletion A216* of SEQ ID NO: 2.

In another aspect, the variant comprises or consists of a substitution at a position corresponding to position 217. In another aspect, the amino acid at a position corresponding to position 217 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Gly, or Trp. In another aspect, the variant comprises or consists of the substitution N217A,G,W of SEQ ID NO: 2.

In another aspect, the variant comprises or consists of an alteration at positions corresponding to positions 214 and 215, such as those described above.

In another aspect, the variant comprises or consists of alterations at positions corresponding to positions 214 and 216, such as those described above.

In another aspect, the variant comprises or consists of alterations at positions corresponding to positions 214 and 217, such as those described above.

In another aspect, the variant comprises or consists of alterations at positions corresponding to positions 215 and 216, such as those described above.

In another aspect, the variant comprises or consists of alterations at positions corresponding to positions 215 and 217, such as those described above.

In another aspect, the variant comprises or consists of alterations at positions corresponding to positions 216 and 217, such as those described above.

In another aspect, the variant comprises or consists of alterations at positions corresponding to positions 214, 215, and 216, such as those described above.

In another aspect, the variant comprises or consists of alterations at positions corresponding to positions 214, 215, and 217, such as those described above.

In another aspect, the variant comprises or consists of alterations at positions corresponding to positions 214, 216, and 217, such as those described above.

In another aspect, the variant comprises or consists of alterations at positions corresponding to positions 215, 216, and 217, such as those described above.

In another aspect, the variant comprises or consists of alterations at positions corresponding to positions 214, 215, 216, and 217, such as those described above.

In another aspect, the variant comprises or consists of one or more alterations selected from the group consisting of N214A, N215A, A216*, and N217A,G,W.

In another aspect, the variant comprises or consists of the alterations N214A+N215A of SEQ ID NO: 2.

In another aspect, the variant comprises or consists of the alterations N214A+A216* of SEQ ID NO: 2.

In another aspect, the variant comprises or consists of the alterations N214A+N217A,G,W of SEQ ID NO: 2.

In another aspect, the variant comprises or consists of the alterations N215A+A216* of SEQ ID NO: 2.

In another aspect, the variant comprises or consists of the alterations N215A+N217A,G,W of SEQ ID NO: 2.

In another aspect, the variant comprises or consists of the alterations A216*+N217A,G,W of SEQ ID NO: 2.

In another aspect, the variant comprises or consists of the alterations N214A+N215A+A216* of SEQ ID NO: 2.

In another aspect, the variant comprises or consists of the alterations N214A+N215A+N217A,G,W of SEQ ID NO: 2.

In another aspect, the variant comprises or consists of the alterations N214A+A216*+N217A,G,W of SEQ ID NO: 2.

In another aspect, the variant comprises or consists of the alterations N215A+A216*+N217A,G,W of SEQ ID NO: 2.

In another aspect, the variant comprises or consists of the alterations N214A+N215A+A216*+N217A,G,W of SEQ ID NO: 2.

Essential amino acids in a parent can be identified according to procedures known in the art, as described herein.

In some aspects, the cellobiohydrolase variants may consist of 310 to 537 amino acids, inclusive, e.g., 310 to 320, 320 to 330, 330 to 340, 340 to 350, 350 to 360, 360 to 370, 370 to 380, 380 to 390, 390 to 400, 400 to 415, 415 to 425, 425 to 435, 435 to 445, 445 to 455, 455 to 465, 465 to 475, 475 to 485, 485 to 495, 495 to 505, 505 to 515, 515 to 525, or 525 to 537 amino acids.

Parent Cellobiohydrolases and Carbohydrate Binding Modules

The parent carbohydrate binding module may be (a) a carbohydrate binding module having at least 60% sequence identity to the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28; (b) a carbohydrate binding module encoded by a polynucleotide that hybridizes under at least low stringency conditions with the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof; or (c) a carbohydrate binding module encoded by a polynucleotide having at least 60% sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27.

The parent cellobiohydrolase may be (a) a polypeptide having at least 60% sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78; (b) a polypeptide encoded by a polynucleotide that hybridizes under at least low stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii); (c) a polypeptide encoded by a polynucleotide having at least 60% sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; or (d) a fragment of (a), (b), or (c), which has cellobiohydrolase activity.

In a first aspect, the parent carbohydrate binding module has a sequence identity to the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have carbohydrate binding activity. In one embodiment, the amino acid sequence of the parent carbohydrate binding module differs by up to 10 amino acids, e.g., 1, 2, 3, 4, 5, 6, 7, 8, 9, or 10, from the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28.

In another embodiment, the parent carbohydrate binding module comprises or consists of the amino acid sequence of SEQ ID NO: 4, SEQ ID NO: 8, SEQ ID NO: 12, SEQ ID NO: 16, SEQ ID NO: 20, SEQ ID NO: 24, or SEQ ID NO: 28.

In another embodiment, the parent carbohydrate binding module is a fragment of the mature polypeptide of SEQ ID NO: 4, SEQ ID NO: 8, SEQ ID NO: 12, SEQ ID NO: 16, SEQ ID NO: 20, SEQ ID NO: 24, or SEQ ID NO: 28 containing at least 28 amino acid residues, e.g., at least 30, at least 32, or at least 34 amino acid residues.

In another embodiment, the parent carbohydrate binding module is an allelic variant of the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28.

In another first aspect, the parent cellobiohydrolase has a sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In one embodiment, the amino acid sequence of the parent cellobiohydrolase differs by up to 10 amino acids, e.g., 1, 2, 3, 4, 5, 6, 7, 8, 9, or 10, from the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

In another embodiment, the parent cellobiohydrolase comprises or consists of the amino acid sequence of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78. In another embodiment, the parent cellobiohydrolase comprises or consists of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78. In another embodiment, the parent cellobiohydrolase comprises or consists of amino acids 18 to 514 of SEQ ID NO: 2, amino acids 19 to 525 of SEQ ID NO: 6, amino acids 19 to 530 of SEQ ID NO: 10, amino acids 26 to 537 of SEQ ID NO: 14, amino acids 27 to 532 of SEQ ID NO: 18, amino acids 18 to 526 of SEQ ID NO: 22, or amino acids 18 to 525 of SEQ ID NO: 26.

In another embodiment, the parent cellobiohydrolase is a fragment containing at least 85% of the amino acid residues, e.g., at least 90% of the amino acid residues or at least 95% of the amino acid residues of the mature polypeptide of the parent cellobiohydrolase.

In another embodiment, the parent cellobiohydrolase is an allelic variant of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

In a second aspect, the parent carbohydrate binding module is encoded by a polynucleotide that hybridizes under very low stringency conditions, low stringency conditions, medium stringency conditions, medium-high stringency conditions, high stringency conditions, or very high stringency conditions with the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof (Sambrook et al., 1989, *Molecular Cloning, A Laboratory Manual,* 2d edition, Cold Spring Harbor, New York).

In another second aspect, the parent cellobiohydrolase is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii) (Sambrook et al., 1989, supra).

The polynucleotide of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, SEQ ID NO: 77, SEQ ID NO: 3, SEQ ID NO: 7, SEQ ID NO: 11, SEQ ID NO: 15, SEQ ID NO: 19, SEQ ID NO: 23, or SEQ ID NO: 27, or a subsequence thereof, as well as the polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78, SEQ ID NO: 4, SEQ ID NO: 8, SEQ ID NO: 12, SEQ ID NO: 16, SEQ ID NO: 20, SEQ ID NO: 24, or SEQ ID NO: 28, or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^3$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, SEQ ID NO: 3, SEQ ID NO: 7, SEQ ID NO: 11, SEQ ID NO: 15, SEQ ID NO: 19, SEQ ID NO: 23, or SEQ ID NO: 27, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; (ii) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; (iii) the genomic DNA or cDNA sequence thereof; (iv) the full-length complement thereof; or (v) a subsequence thereof; or (i) SEQ ID NO: 3, SEQ ID NO: 7, SEQ ID NO: 11, SEQ ID NO: 15, SEQ ID NO: 19, SEQ ID NO: 23, or SEQ ID NO: 27; (ii) the full-length complement thereof; or (iii) a subsequence thereof; under very low to very high stringency conditions. Molecules to which the nucleic acid probe hybridizes under these conditions can be detected using, for example, X-ray film or any other detection means known in the art.

In one embodiment, the nucleic acid probe is the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77. In another embodiment, the nucleic acid probe is nucleotides 52 to 1542 of SEQ ID NO: 1, nucleotides 55 to 1635 of SEQ ID NO: 5, nucleotides 55 to 1590 of SEQ ID NO: 9, nucleotides 76 to 1614 of SEQ ID NO: 13, nucleotides 79 to 1596 of SEQ ID NO: 17, nucleotides 52 to 1578 of SEQ ID NO: 21, or nucleotides 52 to 1575 of SEQ ID NO: 25. In another embodiment, the nucleic acid probe is a polynucleotide that encodes the polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78; the mature polypeptide thereof; or a fragment thereof. In another embodiment, the nucleic acid probe is SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77 or the genomic DNA or cDNA sequence thereof.

In another embodiment, the nucleic acid probe is SEQ ID NO: 3, SEQ ID NO: 7, SEQ ID NO: 11, SEQ ID NO: 15, SEQ ID NO: 19, SEQ ID NO: 23, or SEQ ID NO: 27. In another embodiment, the nucleic acid probe is a polynucleotide that encodes the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28, or a fragment thereof.

For short probes of about 15 nucleotides to about 70 nucleotides in length, stringency conditions are defined as prehybridization and hybridization at about 5° C. to about 10° C. below the calculated T, using the calculation according to Bolton and McCarthy (1962, Proc. Natl. Acad. Sci. USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a third aspect, the parent carbohydrate binding module is encoded by a polynucleotide having a sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encodes a polypeptide having carbohydrate binding activity. In one embodiment, the carbohydrate binding module coding sequence is SEQ ID NO: 3, SEQ ID NO: 7, SEQ ID NO: 11, SEQ ID NO: 15, SEQ ID NO: 19, SEQ ID NO: 23, or SEQ ID NO: 27. In another embodiment, the parent is encoded by a polynucleotide comprising or consisting of SEQ ID NO: 3, SEQ ID NO: 7, SEQ ID NO: 11, SEQ ID NO: 15, SEQ ID NO: 19, SEQ ID NO: 23, or SEQ ID NO: 27.

In another third aspect, the parent cellobiohydrolase is encoded by a polynucleotide having a sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77 or the genomic DNA or cDNA sequence thereof, of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encodes a polypeptide having cellobiohydrolase activity. In one aspect, the mature polypeptide coding sequence is nucleotides 52 to 1542 of SEQ ID NO: 1, nucleotides 55 to 1635 of SEQ ID NO: 5, nucleotides 55 to 1590 of SEQ ID NO: 9, nucleotides 76 to 1614 of SEQ ID NO: 13, nucleotides 79 to 1596 of SEQ ID NO: 17, nucleotides 52 to 1578 of SEQ ID NO: 21, or nucleotides 52 to 1575 of SEQ ID NO: 25, or the genomic DNA or cDNA sequence thereof. In another aspect, the parent cellobiohydrolase is encoded by a polynucleotide comprising or consisting of SEQ ID NO: 1, SEQ ID NO: 5, SEQ ID NO: 9, SEQ ID NO: 13, SEQ ID NO: 17, SEQ ID NO: 21, or SEQ ID NO: 25 or the genomic DNA or cDNA sequence thereof.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial cellobiohydrolase or carbohydrate binding module. For example, the parent may be a Gram-positive bacterial polypeptide such as a Bacillus, Clostridium, Enterococcus, Geobacillus, Lactobacillus, Lactococcus, Oceanobacillus, Staphylococcus, Streptococcus, or Streptomyces cellobiohydrolase, or a Gram-negative bacterial polypeptide such as a Campylobacter, E. coli, Flavobacterium, Fusobacterium, Helicobacter, Ilyobacter, Neisseria, Pseudomonas, Salmonella, or Ureaplasma polypeptide.

In one aspect, the parent is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, or Bacillus thuringiensis polypeptide.

In another aspect, the parent is a Streptococcus equisimilis, Streptococcus pyogenes, Streptococcus uberis, or Streptococcus equi subsp. Zooepidemicus polypeptide.

In another aspect, the parent is a Streptomyces achromogenes, Streptomyces avermitilis, Streptomyces coelicolor, Streptomyces griseus, or Streptomyces lividans polypeptide.

The parent may be a fungal cellobiohydrolase or carbohydrate binding module. For example, the parent may be a yeast cellobiohydrolase or carbohydrate binding module such as a Candida, Kluyveromyces, Pichia, Saccharomyces, Schizosaccharomyces, or Yarrowia polypeptide. For example, the parent may be a filamentous fungal cellobiohydrolase or carbohydrate binding module such as an Acremonium, Agaricus, Alternaria, Aspergillus, Aureobasidium, Botryosphaeria, Ceriporiopsis, Chaetomium, Chrysosporium, Claviceps, Cochliobolus, Coprinopsis, Coptotermes, Corynascus, Cryphonectria, Cryptococcus, Diplodia, Exidia, Fennellia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella, or Xylaria polypeptide.

In another aspect, the parent is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis polypeptide.

In another aspect, the parent is an Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Corynascus thermophilus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum,

*Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Talaromyces byssochlamydoides, Talaromyces emersonii, Thermoascus aurantiacus, Thermoascus crustaceus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polypeptide.

In another aspect, the parent is a *Trichoderma reesei* cellobiohydrolase, e.g., the cellobiohydrolase of SEQ ID NO: 2 or the mature polypeptide thereof, or a *Trichoderma reesei* carbohydrate binding module, e.g., the carbohydrate binding module of SEQ ID NO: 4.

In another aspect, the parent is *Humicola insolens* cellobiohydrolase, e.g., the cellobiohydrolase of SEQ ID NO: 6 or the mature polypeptide thereof, or a *Humicola insolens* carbohydrate binding module, e.g., the carbohydrate binding module of SEQ ID NO: 8.

In another aspect, the parent is a *Chaetomium thermophilum* cellobiohydrolase, e.g., the cellobiohydrolase of SEQ ID NO: 10 or the mature polypeptide thereof, or a *Chaetomium thermophilum* carbohydrate binding module, e.g., the carbohydrate binding module of SEQ ID NO: 12.

In another aspect, the parent is a *Talaromyces byssochlamydoides* cellobiohydrolase, e.g., the cellobiohydrolase of SEQ ID NO: 14 or the mature polypeptide thereof, or a *Talaromyces byssochlamydoides* carbohydrate binding module, e.g., the carbohydrate binding module of SEQ ID NO: 16.

In another aspect, the parent is a *Talaromyces leycettanus* cellobiohydrolase, e.g., the cellobiohydrolase of SEQ ID NO: 42, SEQ ID NO: 44 or the mature polypeptide thereof, or a *Talaromyces leycettanus* carbohydrate binding module, e.g., the carbohydrate binding module of amino acids 472 to 507 of SEQ ID NO: 42 or amino acids 472 to 507 of SEQ ID NO: 44.

In another aspect, the parent is an *Aspergillus fumigatus* cellobiohydrolase, e.g., the cellobiohydrolase of SEQ ID NO: 18, SEQ ID NO: 78, or the mature polypeptide thereof, or an *Aspergillus fumigatus* carbohydrate binding module, e.g., the carbohydrate binding module of SEQ ID NO: 20.

In another aspect, the parent is a *Thielavia terrestris* cellobiohydrolase, e.g., the cellobiohydrolase of SEQ ID NO: 22 or the mature polypeptide thereof, or a *Thielavia terrestris* carbohydrate binding module, e.g., the carbohydrate binding module of SEQ ID NO: 24.

In another aspect, the parent is a *Myceliophthora thermophilum* cellobiohydrolase, e.g., the cellobiohydrolase of SEQ ID NO: 26 or the mature polypeptide thereof, or a *Myceliophthora thermophilum* carbohydrate binding module, e.g., the carbohydrate binding module of SEQ ID NO: 28.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having cellobiohydrolase activity, comprising: (a) introducing into a parent cellobiohydrolase a substitution at one or more (e.g., several) positions corresponding to positions 483, 491, 509 and 510 of SEQ ID NO: 2, wherein the variant has cellobiohydrolase activity; and (b) recovering the variant.

The present invention also relates to methods for obtaining a carbohydrate binding module variant, comprising: (a) introducing into a parent carbohydrate binding module a substitution at one or more (e.g., several) positions corresponding to positions 5, 13, 31 and 32 of the carbohydrate binding module of SEQ ID NO: 4, wherein the variant has carbohydrate binding activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Hybrid Polypeptides

The present invention also relates to hybrid polypeptides comprising a carbohydrate binding module variant described herein and a heterologous catalytic domain of a cellulolytic enzyme. In some embodiments, the hybrid polypeptide has carbohydrate binding activity. In some embodiments, the hybrid polypeptide has cellulolytic activity (e.g., cellobiohydrolase activity). In some embodiments, the hybrid polypeptide has both carbohydrate binding activity and cellulolytic activity (e.g., cellobiohydrolase activity).

The hybrid polypeptide may be formed by fusing a catalytic domain of a cellulolytic enzyme lacking a carbohydrate binding module to a carbohydrate binding module variant described herein, or by replacing an existing catalytic domain of a cellulolytic enzyme comprising the carbohydrate binding module variant (such as a cellobiohydrolase variant described herein) with a catalytic domain of a different cellulolytic enzyme.

In one aspect, the carbohydrate binding module variant is fused to the N-terminus of a heterologous catalytic domain. In another aspect, the carbohydrate binding module variant is fused to the C-terminus of a heterologous catalytic domain.

In one aspect is a hybrid polypeptide having cellulolytic activity, comprising:

(a) a fragment at the N-terminal end of the hybrid polypeptide comprising the heterologous catalytic domain of a cellulolytic enzyme; and (b) a fragment at the C-terminal end of the first polypeptide fragment comprising a carbohydrate binding module variant, wherein the variant comprises a substitution at one or more (e.g., several) positions corresponding to positions 5, 13, 31 and 32 of the carbohydrate binding module of SEQ ID NO: 4.

The catalytic domain used in the hybrid polypeptides may be any suitable catalytic domain of any cellulolytic enzyme described herein (such as the catalytic domain of any cellulolytic enzyme described in the enzyme composition section below), and may be obtained from microorganisms of any genus, as described supra.

For example, the catalytic domain may be obtained from an endoglucanase, a cellobiohydrolase, or a GH61 polypeptide, inter alia. In one embodiment, the catalytic domain is from an endoglucanase. In another embodiment, the catalytic domain is from a cellobiohydrolase. In another embodiment, the catalytic domain is from a GH61 polypeptide.

In one aspect, the catalytic domain of the hybrid polypeptide is a cellobiohydrolase catalytic domain and the hybrid polypeptide has cellobiohydrolase activity.

The catalytic domain of the hybrid polypeptide may be a filamentous fungal cellobiohydrolase. For example, the parent may be a filamentous fungal cellobiohydrolase such as an *Aspergillus, Chaetomium, Chrysosporium, Myceliophthora, Penicillium, Talaromyces, Thermoascus,* or *Trichoderma* cellobiohydrolase.

In one aspect, the catalytic domain of the hybrid polypeptide is an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Chaetomium thermophilum, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Myceliophthora thermophila, Penicillium emersonii, Penicillium funiculosum, Penicillium purpurogenum, Talaromyces byssochlamydoides, Talaromyces emersonii, Talaromyces leycettanus, Trichoderma harzianum, Trichoderma koningii, Trichoderma longibrachiatum, Trichoderma reesei,* or *Trichoderma viride* cellobiohydrolase catalytic domain.

In one embodiment, the catalytic domain is a heterologous catalytic domain of a *Trichoderma reesei* cellobiohydrolase, e.g., the catalytic domain of SEQ ID NO: 30, such as amino acids 1 to 429 of SEQ ID NO: 30

In another embodiment, the catalytic domain is a heterologous catalytic domain of an *Aspergillus fumigatus* cellobiohydrolase, e.g., the catalytic domain of SEQ ID NO: 36, such as amino acids 1 to 437 of SEQ ID NO: 36.

In another embodiment, the catalytic domain is a heterologous catalytic domain of a *Thermoascus aurantiacus* cellobiohydrolase, e.g., the catalytic domain of SEQ ID NO: 38, such as amino acids 1 to 440 of SEQ ID NO: 38.

In another embodiment, the catalytic domain is a heterologous catalytic domain of a *Penicillium emersonii* (*Rasamsonia emersonii*) cellobiohydrolase, e.g., the catalytic domain of SEQ ID NO: 40, such as amino acids 1 to 437 of SEQ ID NO: 40

In another embodiment, the catalytic domain is a heterologous catalytic domain of a *Talaromyces leycettanus* cellobiohydrolase, e.g., the catalytic domain of SEQ ID NO:

42, such as amino acids 1 to 437 of SEQ ID NO: 42 or the catalytic domain of SEQ ID NO: 44 such as amino acids 1 to 438 of SEQ ID NO: 44.

In another embodiment, the catalytic domain is a heterologous catalytic domain of a *Talaromyces byssochlamydoides* cellobiohydrolase, e.g., the catalytic domain of SEQ ID NO: 46, such as amino acids 1 to 437 of SEQ ID NO: 46.

In another embodiment, the catalytic domain is a heterologous catalytic domain of a *Myceliophthora thermophila* cellobiohydrolase, e.g., the catalytic domain of SEQ ID NO: 48, such as amino acids 1 to 430 of SEQ ID NO: 48.

In another embodiment, the catalytic domain is a heterologous catalytic domain of a *Chaetomium thermophilum* cellobiohydrolase, e.g., the catalytic domain of SEQ ID NO: 50, such as amino acids 1 to 433 of SEQ ID NO: 50

In another aspect is a hybrid polypeptide having cellulolytic activity, comprising:

(a) a fragment at the N-terminal end of the hybrid polypeptide comprising the heterologous catalytic domain of a cellulolytic enzyme, wherein the fragment (i) has at least 60% identity to amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, (ii) is encoded by catalytic domain coding sequence that hybridizes under low stringency condition with nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; the cDNA sequence thereof; or the full-length complement of the foregoing;

(iii) is encoded by catalytic domain coding sequence having at least 60% identity to nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; or cDNA sequence thereof;

(iv) is a variant of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, comprising a substitution, deletion, and/or insertion at one or more (e.g., several) positions; or (v) comprises or consists of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50; and (b) a fragment at the C-terminal end of the first polypeptide fragment comprising a carbohydrate binding module variant, wherein the variant comprises a substitution at one or more (e.g., several) positions corresponding to positions 5, 13, 31 and 32 of the carbohydrate binding module of SEQ ID NO: 4.

In one embodiment, the fragment at the N-terminal end of the hybrid polypeptide comprising the heterologous catalytic domain (i) has at least 60% identity to amino acids 1 to 429 of SEQ ID NO: 30; (ii) is encoded by catalytic domain coding sequence that hybridizes under low stringency condition with nucleotides 52 to 1469 of SEQ ID NO: 29, nucleotides 52 to 1389 of SEQ ID NO: 31, or nucleotides 52 to 1389 of SEQ ID NO: 32; the cDNA sequence thereof; or the full-length complement of the foregoing; or (iii) is encoded by catalytic domain coding sequence having at least 60% identity to nucleotides 52 to 1469 of SEQ ID NO: 29, nucleotides 52 to 1389 of SEQ ID NO: 31, or nucleotides 52 to 1389 of SEQ ID NO: 32.

In another embodiment, the fragment at the N-terminal end of the hybrid polypeptide comprising the heterologous catalytic domain (i) has at least 60% identity to amino acids 1 to 437 of SEQ ID NO: 36; (ii) is encoded by catalytic domain coding sequence that hybridizes under low stringency condition with nucleotides 79 to 1389 of SEQ ID NO: 35; the cDNA sequence thereof; or the full-length complement of the foregoing; or (iii) is encoded by catalytic domain coding sequence having at least 60% identity to nucleotides 79 to 1389 of SEQ ID NO: 35.

In another embodiment, the fragment at the N-terminal end of the hybrid polypeptide comprising the heterologous catalytic domain (i) has at least 60% identity to amino acids 1 to 440 of SEQ ID NO: 38; (ii) is encoded by catalytic domain coding sequence that hybridizes under low stringency condition with nucleotides 52 to 1371 of SEQ ID NO: 37; the cDNA sequence thereof; or the full-length complement of the foregoing; or (iii) is encoded by catalytic domain coding sequence having at least 60% identity to nucleotides 52 to 1371 of SEQ ID NO: 37.

In another embodiment, the fragment at the N-terminal end of the hybrid polypeptide comprising the heterologous catalytic domain (i) has at least 60% identity to amino acids 1 to 437 of SEQ ID NO: 40; (ii) is encoded by catalytic domain coding sequence that hybridizes under low stringency condition with nucleotides 55 to 1482 of SEQ ID NO: 39; the cDNA sequence thereof; or the full-length complement of the foregoing; or (iii) is encoded by catalytic domain coding sequence having at least 60% identity to nucleotides 55 to 1482 of SEQ ID NO: 39.

In another embodiment, the fragment at the N-terminal end of the hybrid polypeptide comprising the heterologous catalytic domain (i) has at least 60% identity to amino acids 1 to 437 of SEQ ID NO: 42; (ii) is encoded by catalytic domain coding sequence that hybridizes under low stringency condition with nucleotides 76 to 1386 of SEQ ID NO: 41; the cDNA sequence thereof; or the full-length complement of the foregoing; or (iii) is encoded by catalytic domain coding sequence having at least 60% identity to nucleotides 76 to 1386 of SEQ ID NO: 41.

In another embodiment, the fragment at the N-terminal end of the hybrid polypeptide comprising the heterologous catalytic domain (i) has at least 60% identity to amino acids 1 to 438 of SEQ ID NO: 44; (ii) is encoded by catalytic domain coding sequence that hybridizes under low stringency condition with nucleotides 76 to 1386 of SEQ ID NO: 43; the cDNA sequence thereof; or the full-length complement of the foregoing; or (iii) is encoded by catalytic domain coding sequence having at least 60% identity to nucleotides 76 to 1386 of SEQ ID NO: 43.

In another embodiment, the fragment at the N-terminal end of the hybrid polypeptide comprising the heterologous catalytic domain (i) has at least 60% identity to amino acids 1 to 437 of SEQ ID NO: 46; (ii) is encoded by catalytic domain coding sequence that hybridizes under low stringency condition with nucleotides 55 to 1504 of SEQ ID NO: 45; the cDNA sequence thereof; or the full-length complement of the foregoing; or (iii) is encoded by catalytic domain coding sequence having at least 60% identity to nucleotides 55 to 1504 of SEQ ID NO: 45.

In another embodiment, the fragment at the N-terminal end of the hybrid polypeptide comprising the heterologous catalytic domain (i) has at least 60% identity to amino acids 1 to 430 of SEQ ID NO: 48; (ii) is encoded by catalytic domain coding sequence that hybridizes under low stringency condition with nucleotides 61 to 1350 of SEQ ID NO: 47; the cDNA sequence thereof; or the full-length complement of the foregoing; or (iii) is encoded by catalytic domain coding sequence having at least 60% identity to nucleotides 61 to 1350 of SEQ ID NO: 47.

In another embodiment, the fragment at the N-terminal end of the hybrid polypeptide comprising the heterologous catalytic domain (i) has at least 60% identity to amino acids 1 to 433 of SEQ ID NO: 50; (ii) is encoded by catalytic domain coding sequence that hybridizes under low stringency condition with nucleotides 55 to 1353 of SEQ ID NO: 49; the cDNA sequence thereof; or the full-length complement of the foregoing; or (iii) is encoded by catalytic domain coding sequence having at least 60% identity to nucleotides 55 to 1353 of SEQ ID NO: 49.

In another embodiment, the fragment at the N-terminal end of the hybrid polypeptide comprising the heterologous catalytic domain has a sequence identity to amino acids 1 to 429 of SEQ ID NO: 30 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 429 of SEQ ID NO: 30. In another embodiment, the fragment at the N-terminal end of the hybrid polypeptide comprising the heterologous catalytic domain comprises or consists of amino acids 1 to 429 of SEQ ID NO: 30.

In another embodiment, the fragment at the N-terminal end of the hybrid polypeptide comprising the heterologous catalytic domain has a sequence identity to amino acids 1 to 437 of SEQ ID NO: 36 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 36. In another embodiment, the fragment at the N-terminal end of the hybrid polypeptide comprising the heterologous catalytic domain comprises or consists of amino acids 1 to 437 of SEQ ID NO: 36.

In another embodiment, the fragment at the N-terminal end of the hybrid polypeptide comprising the heterologous catalytic domain has a sequence identity to amino acids 1 to 440 of SEQ ID NO: 38 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 440 of SEQ ID NO: 38. In another embodiment, the fragment at the N-terminal end of the hybrid polypeptide comprising the heterologous catalytic domain comprises or consists of amino acids 1 to 440 of SEQ ID NO: 38.

In another embodiment, the fragment at the N-terminal end of the hybrid polypeptide comprising the heterologous catalytic domain has a sequence identity to amino acids 1 to 437 of SEQ ID NO: 40 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 40. In another embodiment, the fragment at the N-terminal end of the hybrid polypeptide comprising the heterologous catalytic domain comprises or consists of amino acids 1 to 437 of SEQ ID NO: 40.

In another embodiment, the fragment at the N-terminal end of the hybrid polypeptide comprising the heterologous catalytic domain has a sequence identity to amino acids 1 to 437 of SEQ ID NO: 42 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 42. In another embodiment, the fragment at the N-terminal end of the hybrid polypeptide comprising the heterologous catalytic domain comprises or consists of amino acids 1 to 437 of SEQ ID NO: 42.

In another embodiment, the fragment at the N-terminal end of the hybrid polypeptide comprising the heterologous catalytic domain has a sequence identity to amino acids 1 to 438 of SEQ ID NO: 44 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 438 of SEQ ID NO: 44. In another embodiment, the fragment at the N-terminal end of the hybrid polypeptide comprising the heterologous catalytic domain comprises or consists of amino acids 1 to 438 of SEQ ID NO: 44.

In another embodiment, the fragment at the N-terminal end of the hybrid polypeptide comprising the heterologous catalytic domain has a sequence identity to amino acids 1 to 437 of SEQ ID NO: 46 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 46. In another embodiment, the fragment at the N-terminal end of the hybrid polypeptide comprising the heterologous catalytic domain comprises or consists of amino acids 1 to 437 of SEQ ID NO: 46.

In another embodiment, the fragment at the N-terminal end of the hybrid polypeptide comprising the heterologous catalytic domain has a sequence identity to amino acids 1 to 430 of SEQ ID NO: 48 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 430 of SEQ ID NO: 48. In another embodiment, the fragment at the N-terminal end of the hybrid polypeptide comprising the heterologous catalytic domain comprises or consists of amino acids 1 to 430 of SEQ ID NO: 48. In some embodiments, the hybrid polypeptide comprises or consists of SEQ ID NO: 61. In other embodiments, the hybrid polypeptide comprises or consists of SEQ ID NO: 63.

In another embodiment, the fragment at the N-terminal end of the hybrid polypeptide comprising the heterologous catalytic domain has a sequence identity to amino acids 1 to 433 of SEQ ID NO: 50 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 433 of SEQ ID NO: 50. In another embodiment, the fragment at the N-terminal end of the hybrid polypeptide comprising the heterologous catalytic domain comprises or consists of amino acids 1 to 433 of SEQ ID NO: 50.

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 52 to 1469 of SEQ ID NO: 29, nucleotides 52 to 1389 of SEQ ID NO: 31, nucleotides 52 to 1389 of SEQ ID NO: 32; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 79 to 1389 of SEQ ID NO: 35; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 52 to 1371 of SEQ ID NO: 37; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 55 to 1482 of SEQ ID NO: 39; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 76 to 1386 of SEQ ID NO: 41; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 76 to 1386 of SEQ ID NO: 43; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 55 to 1504 of SEQ ID NO: 45; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 61 to 1350 of SEQ ID NO: 47; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 55 to 1353 of SEQ ID NO: 49; the cDNA sequence thereof; or the full-length complement of the foregoing (Sambrook et al., 1989, supra).

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 52 to 1469 of SEQ ID NO: 29, nucleotides 52 to 1389 of SEQ ID NO: 31, nucleotides 52 to 1389 of SEQ ID NO: 32; or the cDNA sequence thereof. In another embodiment, the fragment at the N-terminal end of the hybrid polypeptide comprising the heterologous catalytic domain comprises or consists of nucleotides 52 to 1469 of SEQ ID NO: 29, nucleotides 52 to 1389 of SEQ ID NO: 31, nucleotides 52 to 1389 of SEQ ID NO: 32; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 79 to 1389 of SEQ ID NO: 35; or the cDNA sequence thereof. In another embodiment, the fragment at the N-terminal end of the hybrid polypeptide comprising the heterologous catalytic domain comprises or consists of nucleotides 79 to 1389 of SEQ ID NO: 35; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 52 to 1371 of SEQ ID NO: 37; or the cDNA sequence thereof. In another embodiment, the fragment at the N-terminal end of the hybrid polypeptide comprising the heterologous catalytic domain comprises or consists of nucleotides 52 to 1371 of SEQ ID NO: 37; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 55 to 1482 of SEQ ID NO: 39; or the cDNA sequence thereof. In another embodiment, the fragment at the N-terminal end of the hybrid polypeptide comprising the heterologous catalytic domain comprises or consists of nucleotides 55 to 1482 of SEQ ID NO: 39; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 76 to 1386 of SEQ ID NO: 41; or the cDNA sequence thereof. In another embodiment, the fragment at the N-terminal end of the hybrid polypeptide comprising the heterologous catalytic domain comprises or consists of nucleotides 76 to 1386 of SEQ ID NO: 41; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 76 to 1386 of SEQ ID NO: 43; or the cDNA sequence thereof. In another embodiment, the fragment at the N-terminal end of the hybrid polypeptide comprising the heterologous catalytic domain comprises or consists of nucleotides 76 to 1386 of SEQ ID NO: 43; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 55 to 1504 of SEQ ID NO: 45; or the cDNA sequence thereof. In another embodiment, the fragment at the N-terminal end of the hybrid polypeptide comprising the heterologous catalytic domain comprises or consists of nucleotides 55 to 1504 of SEQ ID NO: 45; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 61 to 1350 of SEQ ID NO: 47; or the cDNA sequence thereof. In another embodiment, the fragment at the N-terminal end of the hybrid polypeptide comprising the heterologous catalytic domain comprises or consists of nucleotides 61 to 1350 of SEQ ID NO: 47; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 55 to 1353 of SEQ ID NO: 49; or the cDNA sequence thereof. In another embodiment, the fragment at the N-terminal end of the hybrid polypeptide comprising the heterologous catalytic domain comprises or consists of nucleotides 55 to 1353 of SEQ ID NO: 49; or the cDNA sequence thereof.

The fragment at the N-terminal end of the hybrid polypeptide comprising the heterologous catalytic domain of the hybrid polypeptide may further comprise a substitution, a deletion, and/or an insertion at one or more (e.g., several) other positions, such as an alteration at one or more (e.g., several) positions corresponding to positions disclosed in PCT/US2014/022068, WO 2011/050037, WO 2005/028636, WO 2005/001065, WO 2004/016760, and U.S. Pat. No. 7,375,197, which are incorporated herein in their entireties.

For example, in one aspect, the fragment at the N-terminal end comprising the heterologous catalytic domain is a cellobiohydrolase comprising an alteration at one or more positions corresponding to positions 197, 198, 199, and 200 of SEQ ID NO: 30, wherein the alteration at the one or more positions corresponding to positions 197, 198, and 200 is a substitution and the alteration at the position corresponding to position 199 is a deletion. In another aspect, the fragment comprises an alteration at two positions corresponding to any of positions 197, 198, 199, and 200 of SEQ ID NO: 30, wherein the alteration at the one or more positions corresponding to positions 197, 198, and 200 is a substitution and the alteration at the position corresponding to position 199 is a deletion. In another aspect, the fragment comprises an alteration at three positions corresponding to any of positions 197, 198, 199, and 200 of SEQ ID NO: 30, wherein the alteration at the one or more positions corresponding to positions 197, 198, and 200 is a substitution and the alteration at the position corresponding to position 199 is a deletion. In another aspect, the fragment comprises a substitution at each position corresponding to positions 197, 198, and 200 and a deletion at a position corresponding to position 199.

In another aspect, the fragment at the N-terminal end comprising the heterologous catalytic domain comprises or consists of a substitution at a position corresponding to position 197 of SEQ ID NO: 30. In another aspect, the amino acid at a position corresponding to position 197 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the fragment comprises or consists of the substitution N197A of SEQ ID NO: 30.

In another aspect, the fragment at the N-terminal end comprising the heterologous catalytic domain comprises or consists of a substitution at a position corresponding to position 198 of SEQ ID NO: 30. In another aspect, the amino acid at a position corresponding to position 198 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the fragment comprises or consists of the substitution N198A of SEQ ID NO: 30.

In another aspect, the fragment at the N-terminal end comprising the heterologous catalytic domain comprises or consists of a deletion at a position corresponding to position 199 of SEQ ID NO: 30. In another aspect, the amino acid at a position corresponding to position 199 is Ala, Arg, Asn, Asp, Cys, Gln, Glu, Gly, His, Ile, Leu, Lys, Met, Phe, Pro, Ser, Thr, Trp, Tyr, or Val, preferably Ala. In another aspect, the variant comprises or consists of the deletion A199* of SEQ ID NO: 30.

In another aspect, the fragment at the N-terminal end comprising the heterologous catalytic domain comprises or consists of a substitution at a position corresponding to position 200 of SEQ ID NO: 30. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Gly, or Trp. In another aspect, the fragment comprises or consists of the substitution N200A,G,W of the mature polypeptide of SEQ ID NO: 30.

In another aspect, the fragment at the N-terminal end comprising the heterologous catalytic domain comprises or consists of an alteration at positions corresponding to positions 197 and 198 of SEQ ID NO: 30, such as those described above.

In another aspect, the fragment at the N-terminal end comprising the heterologous catalytic domain comprises or consists of alterations at positions corresponding to positions 197 and 199 of SEQ ID NO: 30, such as those described above.

In another aspect, the fragment at the N-terminal end comprising the heterologous catalytic domain comprises or consists of alterations at positions corresponding to positions 197 and 200 of SEQ ID NO: 30, such as those described above.

In another aspect, the fragment at the N-terminal end comprising the heterologous catalytic domain comprises or consists of alterations at positions corresponding to positions 198 and 199 of SEQ ID NO: 30, such as those described above.

In another aspect, the fragment at the N-terminal end comprising the heterologous catalytic domain comprises or consists of alterations at positions corresponding to positions 198 and 200 of SEQ ID NO: 30, such as those described above.

In another aspect, the fragment at the N-terminal end comprising the heterologous catalytic domain comprises or consists of alterations at positions corresponding to positions 199 and 200 of SEQ ID NO: 30, such as those described above.

In another aspect, the fragment at the N-terminal end comprising the heterologous catalytic domain comprises or consists of alterations at positions corresponding to positions 197, 198, and 199 of SEQ ID NO: 30, such as those described above.

In another aspect, the fragment at the N-terminal end comprising the heterologous catalytic domain comprises or consists of alterations at positions corresponding to positions 197, 198, and 200 of SEQ ID NO: 30, such as those described above.

In another aspect, the fragment at the N-terminal end comprising the heterologous catalytic domain comprises or consists of alterations at positions corresponding to positions 197, 199, and 200 of SEQ ID NO: 30, such as those described above.

In another aspect, the fragment at the N-terminal end comprising the heterologous catalytic domain comprises or consists of alterations at positions corresponding to positions 198, 199, and 200 of SEQ ID NO: 30, such as those described above.

In another aspect, the fragment at the N-terminal end comprising the heterologous catalytic domain comprises or consists of alterations at positions corresponding to positions 197, 198, 199, and 200 of SEQ ID NO: 30, such as those described above.

In another aspect, the fragment at the N-terminal end comprising the heterologous catalytic domain comprises or consists of one or more alterations selected from the group consisting of N197A, N198A, A199*, and N200A,G,W.

In another aspect, the fragment at the N-terminal end comprising the heterologous catalytic domain comprises or consists of the alterations N197A+N198A of SEQ ID NO: 30.

In another aspect, the fragment at the N-terminal end comprising the heterologous catalytic domain comprises or consists of the alterations N197A+A199* of SEQ ID NO: 30.

In another aspect, the fragment at the N-terminal end comprising the heterologous catalytic domain comprises or consists of the alterations N197A+N200A,G,W of SEQ ID NO: 30.

In another aspect, the fragment at the N-terminal end comprising the heterologous catalytic domain comprises or consists of the alterations N198A+A199* of SEQ ID NO: 30.

In another aspect, the fragment at the N-terminal end comprising the heterologous catalytic domain comprises or consists of the alterations N198A+N200A,G,W of SEQ ID NO: 30.

In another aspect, the fragment at the N-terminal end comprising the heterologous catalytic domain comprises or consists of the alterations A199*+N200A,G,W of SEQ ID NO: 30.

In another aspect, the fragment at the N-terminal end comprising the heterologous catalytic domain comprises or consists of the alterations N197A+N198A+A199* of SEQ ID NO: 30.

In another aspect, the fragment at the N-terminal end comprising the heterologous catalytic domain comprises or consists of the alterations N197A+N198A+N200A,G,W of SEQ ID NO: 30.

In another aspect, the fragment at the N-terminal end comprising the heterologous catalytic domain comprises or consists of the alterations N197A+A199*+N200A,G,W of SEQ ID NO: 30.

In another aspect, the fragment at the N-terminal end comprising the heterologous catalytic domain comprises or consists of the alterations N198A+A199*+N200A,G,W of SEQ ID NO: 30.

In another aspect, the fragment at the N-terminal end comprising the heterologous catalytic domain comprises or consists of the alterations N197A+N198A+A199*+N200A, G,W of SEQ ID NO: 30.

The carbohydrate binding module variant of the hybrid polypeptides may be any suitable carbohydrate binding module variant described supra.

In one aspect, the carbohydrate binding module variant of the hybrid polypeptide has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent carbohydrate binding module.

In another aspect, the carbohydrate binding module variant of the hybrid polypeptide has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4, SEQ ID NO: 8, SEQ ID NO: 12, SEQ ID NO: 16, SEQ ID NO: 20, SEQ ID NO: 24, or SEQ ID NO: 28.

In one aspect, the number of substitutions in the carbohydrate binding module variants of the hybrid polypeptide is 1-4, such as 1, 2, 3, or 4 substitutions.

In one aspect, the carbohydrate binding module variant of the hybrid polypeptide comprises or consists of a substitution at a position corresponding to position 5 of SEQ ID NO: 4. In one embodiment, the amino acid at a position corresponding to position 5 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 5 of SEQ ID NO: 4 is substituted with Trp. In another embodiment, the amino acid at a position corresponding to position 5 of SEQ ID NO: 4 is Tyr substituted with Trp (e.g., Y5W of SEQ ID NO: 4).

In another aspect, the carbohydrate binding module variant of the hybrid polypeptide comprises or consists of a substitution at a position corresponding to position 13 of SEQ ID NO: 4. In one embodiment, the amino acid at a position corresponding to position 13 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 13 of SEQ ID NO: 4 is substituted with Trp. In another embodiment, the amino acid at a position corresponding to position 13 of SEQ ID NO: 4 is Tyr substituted with Trp (e.g., Y13W of SEQ ID NO: 4).

In another aspect, the carbohydrate binding module variant of the hybrid polypeptide comprises or consists of a substitution at a position corresponding to position 31 of SEQ ID NO: 4. In one embodiment, the amino acid at a position corresponding to position 31 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 31 of SEQ ID NO: 4 is substituted with Trp. In another embodiment, the amino acid at a position corresponding to position 31 of SEQ ID NO: 4 is Tyr substituted with Trp (e.g., Y31W of SEQ ID NO: 4).

In another aspect, the carbohydrate binding module variant of the hybrid polypeptide comprises or consists of a substitution at a position corresponding to position 32 of SEQ ID NO: 4. In one embodiment, the amino acid at a position corresponding to position 32 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 32 of SEQ ID NO: 4 is substituted with Trp. In another embodiment, the amino acid at a position corresponding to position 32 of SEQ ID NO: 4 is Tyr substituted with Trp (e.g., Y5W of SEQ ID NO: 4).

In another aspect, the carbohydrate binding module variant of the hybrid polypeptide comprises or consists of a substitution at two positions corresponding to positions 5, 13, 31 and 32 of SEQ ID NO: 4, such as those described above. In one embodiment, the carbohydrate binding module variant comprises or consists of a substitution at positions corresponding to positions 5 and 13 (e.g., substituted with Trp at positions corresponding to positions 5 and 13, such as Y5W and/or Y13W). In another embodiment, the carbohydrate binding module variant comprises or consists of a substitution at positions corresponding to positions 5 and 31 (e.g., substituted with Trp at positions corresponding to positions 5 and 31, such as Y5W and/or Y31W). In another embodiment, the carbohydrate binding module variant comprises or consists of a substitution at positions corresponding to positions 5 and 32 (e.g., substituted with Trp at positions corresponding to positions 5 and 32, such as Y5W and/or Y32W). In another embodiment, the carbohydrate binding module variant comprises or consists of a substitution at positions corresponding to positions 13 and 31 (e.g., substituted with Trp at positions corresponding to positions 13 and 31, such as Y13W and/or Y31W). In another embodiment, the carbohydrate binding module variant comprises or consists of a substitution at positions corresponding to positions 13 and 32 (e.g., substituted with Trp at positions corresponding to positions 13 and 32, such as Y13W and/or Y32W). In another embodiment, the carbohydrate binding module variant comprises or consists of a substitution at positions corresponding to positions 31 and 32 (e.g., substituted with Trp at positions corresponding to positions 31 and 32, such as Y31W and/or Y32W).

In another aspect, the carbohydrate binding module variant of the hybrid polypeptide comprises or consists of a substitution at three positions corresponding to positions 5, 13, 31 and 32 of SEQ ID NO: 4, such as those described above. In one embodiment, the carbohydrate binding module variant comprises or consists of a substitution at positions corresponding to positions 5, 13, and 31 (e.g., substituted with Trp at positions corresponding to positions 5, 13, and 31, such as Y5W, Y13W, and/or Y31W). In another embodiment, the carbohydrate binding module variant comprises or consists of a substitution at positions corresponding to positions 5, 13, and 32 (e.g., substituted with Trp at positions corresponding to positions 5, 13, and 32, such as Y5W, Y13W, and/or Y32W). In another embodiment, the carbohydrate binding module variant comprises or consists of a substitution at positions corresponding to positions 5, 31, and 32 (e.g., substituted with Trp at positions corresponding to positions 5, 31, and 32, such as Y5W, Y31W, and/or Y32W). In another embodiment, the carbohydrate binding module variant comprises or consists of a substitution at positions corresponding to positions 13, 31, and 32 (e.g., substituted with Trp at positions corresponding to positions 13, 31, and 32, such as Y13W, Y31W, and/or Y32W).

In another aspect, the carbohydrate binding module variant of the hybrid polypeptide comprises or consists of a substitution at all four positions corresponding to positions 5, 13, 31 and 32 of SEQ ID NO: 4, such as those described above. In one embodiment, the carbohydrate binding module variant comprises or consists of a Trp substitution at one or more positions corresponding to positions 5, 13, 31 and 32, such as Y5W, Y13W, Y31W and/or Y32W). The carbohydrate binding module variant of the hybrid polypeptide may further comprise a substitution, a deletion, and/or an insertion at one or more (e.g., several) other positions, such as one or more (e.g., several) substitutions at positions corresponding to positions disclosed in WO 2012/135719, which is incorporated herein by reference. For example, in one aspect, the carbohydrate binding module variant of the hybrid polypeptide further comprises a substitution at one or more (e.g., several) positions corresponding to positions 4, 6, and 29 of SEQ ID NO: 4. In another aspect, the carbohydrate binding module variant of the hybrid polypeptide further comprises a substitution at two positions corresponding to any of positions 4, 6, and 29. In another aspect, the carbohydrate binding module variant of the hybrid polypeptide further comprises a substitution at each position corresponding to positions 4, 6, and 29.

In another aspect, the carbohydrate binding module variant of the hybrid polypeptide further comprises or consists of a substitution at a position corresponding to position 4. In another aspect, the amino acid at a position corresponding to position 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Leu, Lys, Phe, or Trp. In another aspect, the carbohydrate binding module variant of the hybrid polypeptide further comprises or consists of the substitution H4L of SEQ ID NO: 4. In another aspect, the carbohydrate binding module variant of the hybrid polypeptide further comprises or consists of the substitution H4K of SEQ ID NO: 4. In another aspect, the carbohydrate binding module variant of the hybrid polypeptide further comprises or consists of the substitution H4E of SEQ ID NO: 4. In another aspect, the carbohydrate binding module variant of the hybrid polypeptide further comprises or consists of the substitution H4F of SEQ ID NO: 4. In another aspect, the carbohydrate binding module variant of the hybrid polypeptide further comprises or consists of the substitution H4W of SEQ ID NO: 4.

In another aspect, the carbohydrate binding module variant of the hybrid polypeptide further comprises or consists of a substitution at a position corresponding to position 6. In another aspect, the amino acid at a position corresponding to position 6 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the carbohydrate binding module variant of the hybrid polypeptide further comprises or consists of the substitution G6A of SEQ ID NO: 4.

In another aspect, the carbohydrate binding module variant of the hybrid polypeptide further comprises or consists of a substitution at a position corresponding to position 29. In another aspect, the amino acid at a position corresponding to position 29 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the carbohydrate binding module variant of the hybrid polypeptide further comprises or consists of the substitution N29D of SEQ ID NO: 4.

In another aspect, the carbohydrate binding module variant of the hybrid polypeptide further comprises or consists of a substitution at positions corresponding to positions 4 and 6, such as those described above.

In another aspect, the carbohydrate binding module variant of the hybrid polypeptide further comprises or consists of substitutions at positions corresponding to positions 4 and 29, such as those described above.

In another aspect, the carbohydrate binding module variant of the hybrid polypeptide further comprises or consists of substitutions at positions corresponding to positions 6 and 29, such as those described above.

In another aspect, the carbohydrate binding module variant of the hybrid polypeptide further comprises or consists of substitutions at positions corresponding to positions 4, 6, and 29, such as those described above.

In another aspect, the carbohydrate binding module variant of the hybrid polypeptide further comprises or consists of one or more (e.g., several) substitutions selected from the group consisting of H4L,K,E,F,W, G6A, and N29D or the one or more (e.g., several) substitutions selected from the group consisting of H4L,K,E,F,W, G6A, and N29D corresponding to SEQ ID NO: 4 in other cellulose binding modules described herein.

In another aspect, the carbohydrate binding module variant of the hybrid polypeptide further comprises or consists of the substitutions H4L+G6A of SEQ ID NO: 4.

In another aspect, the carbohydrate binding module variant of the hybrid polypeptide further comprises or consists of the substitutions H4K+G6A of SEQ ID NO: 4.

In another aspect, the carbohydrate binding module variant of the hybrid polypeptide further comprises or consists of the substitutions H4E+G6A of SEQ ID NO: 4.

In another aspect, the carbohydrate binding module variant of the hybrid polypeptide further comprises or consists of the substitutions H4F+G6A of SEQ ID NO: 4.

In another aspect, the carbohydrate binding module variant of the hybrid polypeptide further comprises or consists of the substitutions H4W+G6A of SEQ ID NO: 4.

In another aspect, the carbohydrate binding module variant of the hybrid polypeptide further comprises or consists of the substitutions H4L+N29D of SEQ ID NO: 4.

In another aspect, the carbohydrate binding module variant of the hybrid polypeptide further comprises or consists of the substitutions H4K+N29D of SEQ ID NO: 4.

In another aspect, the carbohydrate binding module variant of the hybrid polypeptide further comprises or consists of the substitutions H4E+N29D of SEQ ID NO: 4.

In another aspect, the carbohydrate binding module variant of the hybrid polypeptide further comprises or consists of the substitutions H4F+N29D of SEQ ID NO: 4.

In another aspect, the carbohydrate binding module variant of the hybrid polypeptide further comprises or consists of the substitutions H4W+N29D of SEQ ID NO: 4.

In another aspect, the carbohydrate binding module variant of the hybrid polypeptide further comprises or consists of the substitutions G6A+N29D of SEQ ID NO: 4.

In another aspect, the carbohydrate binding module variant of the hybrid polypeptide further comprises or consists of the substitutions H4L+G6A+N29D of SEQ ID NO: 4.

In another aspect, the carbohydrate binding module variant of the hybrid polypeptide further comprises or consists of the substitutions H4K+G6A+N29D of SEQ ID NO: 4.

In another aspect, the carbohydrate binding module variant of the hybrid polypeptide further comprises or consists of the substitutions H4E+G6A+N29D of SEQ ID NO: 4.

In another aspect, the carbohydrate binding module variant of the hybrid polypeptide further comprises or consists of the substitutions H4F+G6A+N29D of SEQ ID NO: 4.

In another aspect, the carbohydrate binding module variant of the hybrid polypeptide further comprises or consists of the substitutions H4W+G6A+N29D of SEQ ID NO: 4.

In some embodiments, the hybrid polypeptide comprises or consists of SEQ ID NO: 61. In other embodiments, the hybrid polypeptide is encoded by the coding sequence of SEQ ID NO: 60.

In other embodiments, the hybrid polypeptide comprises or consists of SEQ ID NO: 63. In other embodiments, the hybrid polypeptide is encoded by the coding sequence of SEQ ID NO: 62.

In other embodiments, the hybrid polypeptide comprises or consists of SEQ ID NO: 73. In other embodiments, the hybrid polypeptide is encoded by the coding sequence of SEQ ID NO: 72.

In other embodiments, the hybrid polypeptide comprises or consists of SEQ ID NO: 94. In other embodiments, the hybrid polypeptide is encoded by the coding sequence of SEQ ID NO: 93.

Essential amino acids in a parent can be identified according to procedures known in the art, as described herein.

Techniques for producing fusion polypeptides are known in the art, and include ligating the coding sequences encoding the polypeptides so that they are in frame and expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

Polynucleotides

The present invention also relates to isolated polynucleotides encoding the carbohydrate binding module variants, cellobiohydrolase variants, and hybrid polypeptides of the present invention.

Nucleic Acid Constructs

The present invention also relates to nucleic acid constructs comprising a polynucleotide encoding a carbohydrate binding module variant, cellobiohydrolase variant, or hybrid polypeptide of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V,

*Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases).

A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucormiehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a carbohydrate binding module variant, cellobiohydrolase variant, or hybrid polypeptide of the present invention, together with a promoter, and transcriptional and translational stop signals. The various nucleotide and control sequences may be joined together to produce a recombinant expression vector that may include one or more convenient restriction sites to allow for insertion or substitution of the polynucleotide encoding the variant sequence at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a carbohydrate binding module variant, cellobiohydrolase variant, or hybrid polypeptide of the present invention operably linked to one or more control sequences that direct the production of the desired variant polypeptide. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis*,

*Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, eds, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology, Volume* 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a carbohydrate binding module variant, cellobiohydrolase variant, or hybrid polypeptide described herein, comprising: (a) cultivating a recombinant host cell of the present invention under conditions suitable for production of the carbohydrate binding module variant, cellobiohydrolase variant, or hybrid polypeptide; and optionally (b) recovering the carbohydrate binding module variant, cellobiohydrolase variant, or hybrid polypeptide.

The host cells are cultivated in a nutrient medium suitable for production of the variant using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the carbohydrate binding module variant, cellobiohydrolase variant, or hybrid polypeptide described herein to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a carbohydrate binding module variant, cellobiohydrolase variant, or hybrid polypeptide of the present invention. The fermentation broth product further comprises additional ingredients used in the fermentation process, such as, for example, cells (including, the host cells containing the gene encoding a variant of the present invention which are used to produce the variant of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a carbohydrate binding module variant, cellobiohydrolase variant, or hybrid polypeptide of the present invention. Preferably, the compositions are enriched in such a polypeptide. The term "enriched" indicates that the cellobiohydrolase activity or the cellulolytic enzyme activity of the composition has been increased, e.g., with an enrichment factor of at least 1.1.

The composition may comprise a carbohydrate binding module variant, cellobiohydrolase variant, or hybrid polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, expansin, glucoamylase, invertase, laccase, lipase, mannosidase, mutanase, oxidase, pectinolytic enzyme, peroxidase, phytase, polyphenoloxidase, proteolytic enzyme, ribonuclease, swollenin, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following methods for using the cellobiohydrolase variants described herein, or hybrid polypeptides comprising a carbohydrate binding module variant and a heterologous catalytic domain of a cellulolytic enzyme described herein, as well as compositions thereof.

The present invention relates to methods for degrading or converting a cellulosic material, comprising: treating the cellulosic material with an enzyme composition in the presence of a cellobiohydrolase variant or a cellulolytic enzyme comprising a carbohydrate binding module variant of the present invention. In one aspect, the methods further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to methods of producing a fermentation product, comprising: (a) saccharifying a cellulosic material with an enzyme composition in the presence of a cellobiohydrolase variant or a cellulolytic enzyme comprising a carbohydrate binding module variant of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a cellobiohydrolase variant or a cellulolytic enzyme comprising a carbohydrate binding module variant of the present invention. In one aspect, the fermenting of the cellulosic material produces a fermentation product. In another aspect, the method further comprises recovering the fermentation product from the fermentation.

The methods of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of the cellulosic material (Chandra et al., 2007, Substrate pretreatment: The key to effective enzymatic hydrolysis of lignocellulosics?

*Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, Appl. Biochem. Biotechnol. 129-132: 496-508; Varga et al., 2004, Appl. Biochem. Biotechnol. 113-116: 509-523; Sassner et al., 2006, Enzyme Microb. Technol. 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, Bioresource Technol. 91: 179-188; Lee et al., 1999, Adv. Biochem. Eng. Biotechnol. 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, Bioresource Technol. 96: 1959-1966; Mosier et al., 2005, Bioresource Technol. 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, Bioresource Technol. 64: 139-151; Palonen et al., 2004, Appl. Biochem. Biotechnol. 117: 1-17; Varga et al., 2004, Biotechnol. Bioeng. 88: 567-574; Martin et al., 2006, J. Chem. Technol. Biotechnol. 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, Appl. Biochem. Biotechnol. 98: 23-35; Chundawat et al., 2007, Biotechnol. Bioeng. 96: 219-231; Alizadeh et al., 2005, Appl. Biochem. Biotechnol. 121: 1133-1141; Teymouri et al., 2005, Bioresource Technol. 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, Biotechnol.

Bioeng. 90: 473-481; Pan et al., 2006, Biotechnol. Bioeng. 94: 851-861; Kurabi et al., 2005, Appl. Biochem. Biotechnol. 121: 219-230). Sulphuric acid is usually added as a catalyst. In organosolv pretreatment, the majority of hemicellulose and lignin is removed.

Other examples of suitable pretreatment methods are described by Schell et al., 2003, Appl. Biochem. and Biotechnol. Vol. 105-108, p. 69-85, and Mosier et al., 2005, Bioresource Technology 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in Handbook on Bioethanol: Production and Utilization, Wyman, C. E., ed., Taylor & Francis, Washington, DC, 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a cellobiohydrolase variant or a cellulolytic enzyme comprising a carbohydrate binding module variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the methods of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and cellobiohydrolase variants or cellulolytic enzymes comprising a carbohydrate binding module variant depend on several factors including, but not limited to, the mixture of component cellulolytic enzymes and/or hemicellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another preferred aspect, an effective amount of a cellobiohydrolase variant or a cellulolytic enzyme comprising a carbohydrate binding module variant to the cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably about 0.025 to about 1.5 mg, more preferably about 0.05 to about 1.25 mg, more preferably about 0.075 to about 1.25 mg, more preferably about 0.1 to about 1.25 mg, even more preferably about 0.15 to about 1.25 mg, and most preferably about 0.25 to about 1.0 mg per g of the cellulosic material.

In another preferred aspect, an effective amount of a cellobiohydrolase variant or a cellulolytic enzyme comprising a carbohydrate binding module variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity, (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus,*

*Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Rohm GmbH), FIBREZYME® LDI (Dyadic International, Inc.), FIBREZYME®

LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, Gene 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia* carotovara endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM 324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, Gene 173: 287-288), *Aspergillus fumigatus* (WO 2005/047499), *Aspergillus niger* (Dan et al., 2000, J. Biol. Chem. 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In the methods of the present invention, any GH61 polypeptide having cellulolytic enhancing activity can be used.

In a first aspect, the GH61 polypeptide having cellulolytic enhancing activity comprises the following motifs:

```
                        (SEQ ID NO: 27 or SEQ ID NO: 28)
[ILMV]-P-X(4,5)-G-X-Y-[ILMV]-X-R-X-

[EQ]-X(4)-[HNQ]
and

[FW)-[TF]-K-[AIV],
``` wherein X is any amino acid, X(4,5) is any amino acid at 4 or 5 contiguous positions, and X(4) is any amino acid at 4 contiguous positions.

The polypeptide comprising the above-noted motifs may further comprise:

```
                        (SEQ ID NO: 29 or SEQ ID NO: 30)
H-X(1,2)-G-P-X(3)-[YW]-[AILMV], (SEQ ID NO: 31)
[EQ]-X-Y-X(2)-C-X-[EHQN]-[FILV]-X-[ILV],
or (SEQ ID NO: 32 or SEQ ID NO: 33)
H-X(1,2)-G-P-X(3)-[YW]-[AILMV]
and (SEQ ID NO: 34)
[EQ]-X-Y-X(2)-C-X-[EHQN]-[FILV]-X-[ILV],
``` wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the GH61 polypeptide having cellulolytic enhancing activity further comprises H-X(1,2)-G-P-X(3)-[YW]-[AILMV] (SEQ ID NO: 29 or SEQ ID NO:

30). In another preferred aspect, the GH61 polypeptide having cellulolytic enhancing activity further comprises [EQ]-X-Y-X(2)-C-X-[EHQN]-[FILV]-X-[ILV] (SEQ ID NO: 31). In another preferred aspect, the GH61 polypeptide having cellulolytic enhancing activity further comprises H-X(1,2)-G-P-X(3)-[YW]-[AILMV] (SEQ ID NO: 32 or SEQ ID NO: 33) and [EQ]-X—Y-X(2)-C-X-[EHQN]-[FILV]-X-[ILV] (SEQ ID NO: 34).

In a second aspect, the GH61 polypeptide having cellulolytic enhancing activity comprises the following motif:

```
                    (SEQ ID NO: 35 or SEQ ID NO: 36)
    [ILMV]-P-x(4,5)-G-x-Y-[ILMV]- x-R-x-[EQ]-x(3)-A-[HNQ],
``` wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

Examples of GH61 polypeptides having cellulolytic enhancing activity useful in the methods of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In another aspect, the GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1, 2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; $\alpha$-hydroxy-$\gamma$-butyrolactone; ribonic $\gamma$-lactone; aldohexuronicaldohexuronic acid $\gamma$-lactone; gluconic acid $\delta$-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6, 7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 $\mu$M to about 1 M, e.g., about 0.5 $\mu$M to about 0.75 M, about 0.75 $\mu$M to about 0.5 M, about 1 $\mu$M to about 0.25 M, about 1 $\mu$M to about 0.1 M, about 5 $\mu$M to about 50 mM, about 10 $\mu$M to about 25 mM, about 50 $\mu$M to about 25 mM, about 10 $\mu$M to about 10 mM, about 5 $\mu$M to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/ 057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/ TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/ 108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4VWV45), *Aspergillus niger* (Uniprot accession number Q96WX9), *Aspergillus terreus* (SwissProt accession number Q0CJP9), *Humicola insolens* (WO 2010/ 014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation. The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces,* and *Saccharomyces,* e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Preferred xylose fermenting yeast include strains of *Candida,* preferably *C. sheatae* or *C. sonorensis;* and strains of *Pichia,* preferably *P. stipitis,* such as *P. stipitis* CBS 5773. Preferred pentose fermenting yeast include strains of *Pachysolen,* preferably *P. tannophilus.* Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, 1996, supra).

Other fermenting organisms include strains of *Bacillus,* such as *Bacillus coagulans; Candida,* such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium,* such as *C. acetobutylicum, C. thermocellum,* and *C. phytofermentans; E. coli,* especially *E. coli* strains that have been genetically modified to improve the yield of ethanol; *Geobacillus* sp.; *Hansenula,* such as *Hansenula anomala; Klebsiella,* such as *K. oxytoca; Kluyveromyces,* such as *K. marxianus, K. lactis, K. thermotolerans,* and *K. fragilis; Schizosaccharomyces,* such as *S. pombe; Thermoanaerobacter,* such as *Thermoanaerobacter saccharolyticum;* and *Zymomonas,* such as *Zymomonas mobilis.*

In a preferred aspect, the yeast is a *Bretannomyces.* In a more preferred aspect, the yeast is *Bretannomyces clausenii.* In another preferred aspect, the yeast is a *Candida.* In another more preferred aspect, the yeast is *Candida sonorensis.* In another more preferred aspect, the yeast is *Candida boidinii.* In another more preferred aspect, the yeast is *Candida blankii.* In another more preferred aspect, the yeast is *Candida brassicae.* In another more preferred aspect, the yeast is *Candida diddensii.* In another more preferred aspect, the yeast is *Candida entomophiliia.* In another more preferred aspect, the yeast is *Candida pseudotropicalis.* In another more preferred aspect, the yeast is *Candida scehatae.* In another more preferred aspect, the yeast is *Candida utilis.* In another preferred aspect, the yeast is a *Clavispora.* In another more preferred aspect, the yeast is *Clavispora lusitaniae.* In another more preferred aspect, the yeast is *Clavispora opuntiae.* In another preferred aspect, the yeast is a *Kluyveromyces.* In another more preferred aspect, the yeast is *Kluyveromyces fragilis.* In another more preferred aspect, the yeast is *Kluyveromyces marxianus.* In another more preferred aspect, the yeast is *Kluyveromyces thermotolerans.* In another preferred aspect, the yeast is a *Pachysolen.* In another more preferred aspect, the yeast is *Pachysolen tannophilus.* In another preferred aspect, the yeast is a *Pichia.* In another more preferred aspect, the yeast is a *Pichia stipitis.* In another preferred aspect, the yeast is a *Saccharomyces* spp. In another more preferred aspect, the yeast is *Saccharomyces cerevisiae.* In another more preferred aspect, the yeast is *Saccharomyces distaticus.* In another more preferred aspect, the yeast is *Saccharomyces uvarum.*

In a preferred aspect, the bacterium is a *Bacillus.* In a more preferred aspect, the bacterium is *Bacillus coagulans.* In another preferred aspect, the bacterium is a *Clostridium.* In another more preferred aspect, the bacterium is *Clostridium acetobutylicum.* In another more preferred aspect, the bacterium is *Clostridium phytofermentans.* In another more preferred aspect, the bacterium is *Clostridium thermocellum.* In another more preferred aspect, the bacterium is *Geobacillus* sp. In another more preferred aspect, the bacterium is a *Thermoanaerobacter.* In another more preferred aspect, the bacterium is *Thermoanaerobacter saccharolyticum.* In another preferred aspect, the bacterium is a *Zymomonas.* In another more preferred aspect, the bacterium is *Zymomonas mobilis.*

Commercially available yeast suitable for ethanol production include, e.g., BIOFERM™ AFT and XR (NABC—

North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis,* Science 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis.* In another preferred aspect, the genetically modified fermenting microorganism is *Escherichia coli.* In another preferred aspect, the genetically modified fermenting microorganism is *Klebsiella oxytoca.* In another preferred aspect, the genetically modified fermenting microorganism is *Kluyveromyces marxianus.* In another preferred aspect, the genetically modified fermenting microorganism is *Saccharomyces cerevisiae.* In another preferred aspect, the genetically modified fermenting microorganism is *Zymomonas mobilis.*

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7.

However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, Water Science and Technology 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to isolated plants, e.g., a transgenic plant, plant part, or plant cell, comprising a polynucleotide of the present invention so as to express and produce the carbohydrate binding module variant, cellobiohydrolase variant, or hybrid polypeptide of the present invention in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyma, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, Cell 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, *Bio/Technology* 8: 535; Shimamoto et al., 1989, Nature 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The present invention may be further described by the following numbered paragraphs:

[1] An isolated carbohydrate binding module (CBM) variant, comprising a substitution at one or more (e.g., several) positions corresponding to positions 5, 13, 31 and 32 of SEQ ID NO: 4, wherein the variant has carbohydrate binding activity.

[2] The variant of paragraph [1], which is a variant of a parent carbohydrate binding module selected from: (a) a carbohydrate binding module having at least 60% sequence identity to the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28; (b) a carbohydrate binding module encoded by a polynucleotide that hybridizes under at least low stringency conditions with the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof; (c) a carbohydrate binding module encoded by a polynucleotide having at least 60% sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27.

[3] The variant of paragraph [2], wherein the parent carbohydrate binding module has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 4, SEQ ID NO: 8, SEQ ID NO: 12, SEQ ID NO: 16, SEQ ID NO: 20, SEQ ID NO: 24, or SEQ ID NO: 28.

[4] The variant of paragraph [2] or [3], wherein the parent carbohydrate binding module is encoded by a polynucleotide that hybridizes under low stringency conditions, medium stringency conditions, medium-high stringency conditions, high stringency conditions, or very high stringency conditions with SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof.

[5] The variant of any of paragraphs [2]-[4], wherein the parent carbohydrate binding module is encoded by a polynucleotide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27.

[6] The variant of any of paragraphs [2]-[5], wherein the parent carbohydrate binding module comprises or consists of SEQ ID NO: 4, SEQ ID NO: 8, SEQ ID NO: 12, SEQ ID NO: 16, SEQ ID NO: 20, SEQ ID NO: 24, or SEQ ID NO: 28.

[7] The variant of any of paragraphs [2]-[6], wherein the parent carbohydrate binding module is a fragment of SEQ ID NO: 4, SEQ ID NO: 8, SEQ ID NO: 12, SEQ ID NO: 16, SEQ ID NO: 20, SEQ ID NO: 24, or SEQ ID NO: 28, wherein the fragment has carbohydrate binding activity.

[8] The variant of any of paragraphs [2]-[7], which has at least 60%, e.g., at least 65%, at least 70%, at least 75%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the amino acid sequence of the parent carbohydrate binding module.

[9] The variant of any of paragraphs [1]-[8], which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 4, SEQ ID NO: 8, SEQ ID NO: 12, SEQ ID NO: 16, SEQ ID NO: 20, SEQ ID NO: 24, or SEQ ID NO: 28.

[10] The variant of any of paragraphs [1]-[9], wherein the carbohydrate binding module variant consists of 28 to 36 amino acids, e.g., 28, 29, 30, 31, 32, 33, 34, 35, or 36 amino acids.

[11] The variant of any of paragraphs [1]-[10], wherein the number of substitutions is 1-4, e.g., 1, 2, 3 or 4 substitutions.

[12] The variant of any of paragraphs [1]-[11], which comprises a substitution at the position corresponding to position 5 of SEQ ID NO: 4.

[13] The variant of paragraph [12], wherein the substitution is with Tyr, Phe, or Trp, such as Trp (e.g., Y5W).

[14] The variant of any of paragraphs [1]-[13], which comprises a substitution at the position corresponding to position 13 of SEQ ID NO: 4.

[15] The variant of paragraph [14], wherein the substitution is with Tyr, Phe, or Trp, such as Trp (e.g., Y13W).

[16] The variant of any of paragraphs [1]-[15], which comprises a substitution at the position corresponding to position 31 of SEQ ID NO: 4.

[17] The variant of paragraph [16], wherein the substitution is with Tyr, Phe, or Trp, such as Trp (e.g., Y31W).

[18] The variant of any of paragraphs [1]-[17], which comprises a substitution at a position corresponding to position 32 of SEQ ID NO: 4.

[19] The variant of paragraph [18], wherein the substitution is with Tyr, Phe, or Trp, such as Trp (e.g., Y32W).

[20] The variant of any one of paragraphs [1]-[19], which comprises a substitution at two positions corresponding to positions 5 and 13; 5 and 31; 5 and 32; 13 and 31; 13 and 32; or 31 and 32.

[21] The variant of paragraph [20], which comprises the substitutions Y5W+Y13W; Y5W+Y31W; Y5W+Y32W; Y13W+Y31W; Y13W+Y32W; or Y31W+Y32W.

[22] The variant of any one of paragraphs [1]-[19], which comprises a substitution at three positions corresponding to positions 5, 13, and 31; 5, 13, and 32; 5, 31, and 32; or 13, 31, and 32.

[23] The variant of paragraph [22], which comprises the substitutions Y5W, Y13W, +Y31W; Y5W, Y13W, +Y32W; Y5W, Y31W, +Y32W; or Y13W, Y31W, +Y32W.

[24] The variant of any one of paragraphs [1]-[19], which comprises a substitution at all four positions corresponding to positions 5, 13, 31, and 32.

[25] The variant of paragraph [24], which comprises the substitutions Y5W, Y13W, Y31W, and Y32W.

[26] The variant of any of paragraphs [1]-[25], which further comprises a substitution at one or more (e.g., several) positions corresponding to positions 4, 6, and 29 of SEQ ID NO: 4.

[27] An isolated polypeptide having cellulolytic activity, comprising the carbohydrate binding module variant of any of paragraphs [1]-[26].

[28] The polypeptide of paragraph [27], which is selected from the group consisting of an endoglucanase, a cellobiohydrolase, and a GH61 polypeptide.

[29] A composition comprising the variant of any of paragraphs [1]-[28].

[30] An isolated polynucleotide encoding the variant of any of paragraphs [1]-[28].

[31] A nucleic acid construct comprising the polynucleotide of paragraph [30].

[32] An expression vector comprising the polynucleotide of paragraph [30].

[33] A host cell comprising the polynucleotide of paragraph [30].

[34] A method of producing a variant, comprising: cultivating the host cell of paragraph [33] under conditions suitable for expression of the variant.

[35] The method of paragraph [34], further comprising recovering the variant.

[36] A transgenic plant, plant part or plant cell transformed with the polynucleotide of paragraph [30].

[37] A method of producing the variant of any of paragraphs [1]-[28], comprising: cultivating a transgenic plant, plant part or a plant cell comprising a polynucleotide encoding the variant under conditions conducive for production of the variant.

[38] The method of paragraph [37], further comprising recovering the variant.

[39] A method for obtaining a variant of a parent carbohydrate binding module, comprising introducing into the carbohydrate binding module a substitution at one or more (e.g., several) positions corresponding to positions 5, 13, 31, and 32 of SEQ ID NO: 4, wherein the variant has carbohydrate binding activity; and recovering the variant.

[40] An isolated cellobiohydrolase variant, comprising a substitution at one or more (e.g., several) positions corresponding to positions 483, 491, 509 and 510 of SEQ ID NO: 2, wherein the variant has cellobiohydrolase activity.

[41] The variant of paragraph [40], which is a variant of a parent cellobiohydrolase selected from: (a) a polypeptide having at least 60% sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78; (b) a polypeptide encoded by a polynucleotide that hybridizes under at least low stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii); (c) a polypeptide encoded by a polynucleotide having at least 60% sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; and (d) a fragment of (a), (b), or (c), which has cellobiohydrolase activity

[42] The variant of paragraph [41], wherein the parent cellobiohydrolase has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

[43] The variant of paragraph [41] or [42], wherein the parent cellobiohydrolase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii).

[44] The variant of any of paragraphs [41]-[43], wherein the parent cellobiohydrolase is encoded by a polynucleotide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77 or the genomic DNA or cDNA sequence thereof.

[45] The variant of any of paragraphs [41]-[44], wherein the parent cellobiohydrolase comprises or consists of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

[46] The variant of any of paragraphs [41]-[44], wherein the parent cellobiohydrolase is a fragment of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78, wherein the fragment has cellobiohydrolase activity.

[47] The variant of any of paragraphs [41]-[46], which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the amino acid sequence of the parent cellobiohydrolase.

[48] The variant of any of paragraphs [40]-[47], which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

[49] The variant of any of paragraphs [40]-[48], wherein the variant consists of 310 to 537 amino acids, e.g., 310 to 320, 320 to 330, 330 to 340, 340 to 350, 350 to 360, 360 to 370, 370 to 380, 380 to 390, 390 to 400, 400 to 415, 415 to 425, 425 to 435, 435 to 445, 445 to 455, 455 to 465, 465 to 475, 475 to 485, 485 to 495, 495 to 505, 505 to 515, 515 to 525, or 525 to 537 amino acids.

[50] The variant of any of paragraphs [40]-[49], wherein the number of substitutions is 1-4, e.g., 1, 2, 3 or 4 substitutions.

[51] The variant of any of paragraphs [40]-[50], which comprises a substitution at a position corresponding to position 483.

[52] The variant of paragraph [51], wherein the substitution is with Tyr, Phe, or Trp, such as Trp (e.g., Y483W).

[53] The variant of any of paragraphs [40]-[52], which comprises a substitution at a position corresponding to position 491.

[54] The variant of paragraph [53], wherein the substitution is with Tyr, Phe, or Trp, such as Trp (e.g., Y491W).

[55] The variant of any of paragraphs [40]-[54], which comprises a substitution at a position corresponding to position 509.

[56] The variant of paragraph [55], wherein the substitution is with Tyr, Phe, or Trp, such as Trp (e.g., Y509W).

[57] The variant of any of paragraphs [40]-[56], which comprises a substitution at a position corresponding to position 510.

[58] The variant of paragraph [57], wherein the substitution is with Tyr, Phe, or Trp, such as Trp (e.g., Y510W).

[59] The variant of paragraph [40]-[58], which comprises a substitution at two positions corresponding to positions 483 and 491; 483 and 509; 483 and 510; 483 and 509; 483 and 510; or 509 and 510.

[60] The variant of paragraph [59], which comprises the substitutions Y483W+Y491W; Y483W+Y509W; Y483W+Y510W; Y483W+Y509W; Y483W+Y510W; or Y509W+Y510W.

[61] The variant of any one of paragraphs [40]-[50], which comprises a substitution at three positions corresponding to positions 483, 491, and 509; 483, 491, and 510; 483, 509, and 510; or 491, 509, and 510.

[62] The variant of paragraph [61], which comprises the substitutions Y483W, Y491W, +Y509W; Y483W, Y491W, +Y510W; Y483W, Y509W, +Y510W; or Y491W, Y509W, +Y510W.

[63] The variant of any one of paragraphs [40]-[58], which comprises a substitution at all four positions corresponding to positions 483, 491, 509, and 510.

[64] The variant of paragraph [63], which comprises the substitutions Y5W, Y13W, Y31W, +Y32W.

[65] The variant of any of paragraphs [40]-[64], which further comprises a substitution at one or more (e.g., several) positions corresponding to positions 214, 215, 216, and 217 of SEQ ID NO: 2.

[66] The variant of any one of paragraphs [40]-[58] comprising or consisting of SEQ ID NO: 90 or SEQ ID NO: 92, or the mature polypeptide sequence thereof.

[67] A composition comprising the variant of any of paragraphs [40]-[66].

[68] An isolated polynucleotide encoding the variant of any of paragraphs [40]-[66]. [69] A nucleic acid construct comprising the polynucleotide of paragraph [68].

[70] An expression vector comprising the polynucleotide of paragraph [68].

[71] A host cell comprising the polynucleotide of paragraph [68].

[72] A method of producing a variant of a parent cellobiohydrolase, comprising: cultivating the host cell of paragraph [71] under conditions suitable for expression of the variant.

[73] The method of paragraph [72], further comprising recovering the variant.

[74] A transgenic plant, plant part or plant cell transformed with the polynucleotide of paragraph [68].

[75] A method of producing the variant of any of paragraphs [40]-[66], comprising: cultivating a transgenic plant, plant part or a plant cell comprising a polynucleotide encoding the variant under conditions conducive for production of the variant.

[76] The method of paragraph [75], further comprising recovering the variant.

[77] A method for obtaining a variant of a parent cellobiohydrolase, comprising introducing into the parent cellobiohydrolase a substitution at one or more (e.g., several) positions corresponding to positions 483, 491, 509, and 510 of the mature polypeptide of SEQ ID NO: 2, wherein the variant has cellobiohydrolase activity; and recovering the variant.

[78] A hybrid polypeptide comprising a carbohydrate binding module variant of any one of paragraphs [1]-[26], and a heterologous catalytic domain of a cellulolytic enzyme.

[79] The hybrid polypeptide of paragraph [78], having cellulolytic activity (e.g., cellobiohydrolase activity).

[80] A hybrid polypeptide having cellulolytic activity, comprising:
   (a) a fragment at the N-terminal end of the hybrid polypeptide comprising the heterologous catalytic domain of a cellulolytic enzyme; and
   (b) a fragment at the C-terminal end of the first polypeptide fragment comprising a carbohydrate binding module variant of any one of paragraphs [1]-[26].

[81] The hybrid polypeptide of any one of paragraphs [78]-[80], having carbohydrate binding activity.

[82] A hybrid polypeptide having cellulolytic activity, comprising:
   (a) a fragment at the N-terminal end of the hybrid polypeptide comprising the heterologous catalytic domain of a cellulolytic enzyme, wherein the fragment
      (i) has at least 60% identity to amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, (ii) is encoded by catalytic domain coding sequence that hybridizes under low stringency condition with nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; the cDNA sequence thereof; or the full-length complement of the foregoing;
      (iii) is encoded by catalytic domain coding sequence having at least 60% identity to nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; or cDNA sequence thereof;
      (iv) is a variant of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, comprising a substitution, deletion, and/or insertion at one or more (e.g., several) positions; or
      (v) comprises or consists of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50; and
   (b) a fragment at the C-terminal end of the first polypeptide fragment comprising a carbohydrate binding module variant, wherein the variant comprises a substitution at one or more (e.g., several) positions corresponding to positions 5, 13, 31 and 32 of the carbohydrate binding module of SEQ ID NO: 4 (e.g., a carbohydrate binding module variant of any one of paragraphs [1]-[26]).

[83] The hybrid polypeptide of any one of paragraphs [78]-[82] comprising or consisting of SEQ ID NO: 61, SEQ ID NO: 63, SEQ ID NO: 73, or SEQ ID NO: 94, or the mature polypeptide thereof.

[84] The hybrid polypeptide of any of paragraphs [78]-[83], which further comprises a substitution at one or more (e.g., several) positions corresponding to positions 214, 215, 216, and 217 of SEQ ID NO: 2.

[85] A composition comprising the hybrid polypeptide of any of paragraphs [78]-[84].

[86] An isolated polynucleotide encoding the hybrid polypeptide of any of paragraphs [78]-[84].

[87] A nucleic acid construct comprising the polynucleotide of paragraph [86].

[88] An expression vector comprising the polynucleotide of paragraph [86].

[89] A host cell comprising the polynucleotide of paragraph [86].

[90] A method of producing a hybrid polypeptide, comprising: cultivating the host cell of paragraph [89] under conditions suitable for expression of the hybrid polypeptide.

[91] The method of paragraph [90], further comprising recovering the hybrid polypeptide.

[92] A transgenic plant, plant part or plant cell transformed with the polynucleotide of paragraph [86].

[93] A method of producing the hybrid polypeptide of any of paragraphs [78]-[84], comprising: cultivating a transgenic plant, plant part or a plant cell comprising a polynucleotide encoding the hybrid polypeptide under conditions conducive for production of the hybrid polypeptide.

[94] A method for degrading or converting a cellulosic material, comprising: treating the cellulosic material with an enzyme composition in the presence of the variant of any of paragraphs [40]-[66] or the hybrid polypeptide of any of paragraphs [78]-[84].

[95] The method of paragraph [94], wherein the cellulosic material is pretreated.

[96] The method of paragraph [94] or [95], wherein the enzyme composition comprises one or more enzymes selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

[97] The method of paragraph [96], wherein the cellulase is one or more enzymes selected from the group consisting of an endoglucanase, a cellobiohydrolase, and a beta-glucosidase.

[98] The method of paragraph [96], wherein the hemicellulase is one or more enzymes selected from the group consisting of a xylanase, an acetylxylan esterase, a feruloyl esterase, an arabinofuranosidase, a xylosidase, and a glucuronidase.

[99] The method of any of paragraphs [94]-[98], further comprising recovering the degraded cellulosic material.

[100] The method of paragraph [99], wherein the degraded cellulosic material is a sugar.

[101] The method of paragraph [100], wherein the sugar is selected from the group consisting of glucose, xylose, mannose, galactose, and arabinose.

[102] A method for producing a fermentation product, comprising: (a) saccharifying a cellulosic material with an enzyme composition in the presence of the variant of any of paragraphs [40]-[66] or the hybrid polypeptide of any of paragraphs [78]-[84]; (b) fermenting the saccharified cellulosic material with one or more fermenting microorganisms to produce the fermentation product; and (c) recovering the fermentation product from the fermentation.

[103] The method of paragraph [102], wherein the cellulosic material is pretreated.

[104] The method of paragraph [102] or [103], wherein the enzyme composition comprises the enzyme composition comprises one or more enzymes selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

[105] The method of paragraph [104], wherein the cellulase is one or more enzymes selected from the group consisting of an endoglucanase, a cellobiohydrolase, and a beta-glucosidase.

[106] The method of paragraph [104], wherein the hemicellulase is one or more enzymes selected from the group consisting of a xylanase, an acetylxylan esterase, a feruloyl esterase, an arabinofuranosidase, a xylosidase, and a glucuronidase.

[107] The method of any of paragraphs [102]-[106], wherein steps (a) and (b) are performed simultaneously in a simultaneous saccharification and fermentation.

[108] The method of any of paragraphs [102]-[107], wherein the fermentation product is an alcohol, an organic acid, a ketone, an amino acid, an alkane, a cycloalkane, an alkene, isoprene, polyketide, or a gas.

[109] A method of fermenting a cellulosic material, comprising: fermenting the cellulosic material with one or more fermenting microorganisms, wherein the cellulosic material is saccharified with an enzyme composition in the presence of the variant of any of paragraphs [40]-[66] or the hybrid polypeptide of any of paragraphs [78]-[84].

[110] The method of paragraph [109], wherein the fermenting of the cellulosic material produces a fermentation product.

[111] The method of paragraph [110], further comprising recovering the fermentation product from the fermentation.

[112] The method of any of paragraphs [109]-[111], wherein the cellulosic material is pretreated before saccharification.

[113] The method of any of paragraphs [109]-[112], wherein the enzyme composition comprises one or more enzymes selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

[114] The method of paragraph [113], wherein the cellulase is one or more enzymes selected from the group consisting of an endoglucanase, a cellobiohydrolase, and a beta-glucosidase.

[115] The method of paragraph [113], wherein the hemicellulase is one or more enzymes selected from the group consisting of a xylanase, an acetylxylan esterase, a feruloyl esterase, an arabinofuranosidase, a xylosidase, and a glucuronidase.

[116] The method of any of paragraphs [110]-[115, wherein the fermentation product is an alcohol, an organic acid, a ketone, an amino acid, an alkane, a cycloalkane, an alkene, isoprene, polyketide, or a gas.

[117] A whole broth formulation or cell culture composition comprising the variant of any of paragraphs [40]-[66] or the hybrid polypeptide of any of paragraphs [78]-[84].

The present invention is further described by the following examples that should not be construed as limiting the scope of the invention.

EXAMPLES

Strains

*Aspergillus oryzae* strain MT3568 was used as a host for expression of the carbohydrate binding module variants and hybrid polypeptides thereof. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene.

Media and Solutions

COVE sucrose plates or slants were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and then acetamide to 10 mM, CsCl to 15 mM, and TRITON® X-100 (50 μl/500 ml) were added.

COVE salt solution was composed of 26 g of $MgSO_4·7H_2O$, 26 g of KCl, 26 g of $KH_2PO_4$, 50 ml of COVE trace metals solution, and deionized water to 1 liter.

COVE trace metals solution was composed of 0.04 g of $Na_2B_4O_7·10H_2O$, 0.4 g of $CuSO_4·5H_2O$, 1.2 g of $FeSO_4·7H_2O$, 0.7 g of $MnSO_4·H_2O$, 0.8 g of $Na_2MoO_4·2H_2O$, 10 g of $ZnSO_4·7H_2O$, and deionized water to 1 liter.

DAP-4C medium was composed of 20 g of dextrose, 10 g of maltose, 11 g of $MgSO_4·7H_2O$, 1 g of $KH_2PO_4$, 2 g of citric acid, 5.2 g of $K_3PO_4·H_2O$, 0.5 g of yeast extract (Difco), 1 ml of antifoam, 0.5 ml of KU6 trace metals solution, 2.5 g of $CaCO_3$, and deionized water to 1 liter. The medium was sterilized by autoclaving at 15 psi for 15 minutes (Bacteriological Analytical Manual, 8th Edition, Revision A, 1998). Before use, 3.5 ml of sterile 50% $(NH_4)_2HPO_4$ and 5 ml of sterile 20% lactic acid were added per 150 ml.

G2-Gly medium was composed of 18 g of yeast extract, 24 g of glycerol (86-88%), 1 ml of antifoam, and deionized water to 1 liter.

KU6 trace metals solution was composed of 0.13 g of $NiCl_2$, 2.5 g of $CuSO_4·5H_2O$, 13.9 g of $FeSO_4·7H_2O$, 8.45 g of $MnSO_4·H_2O$, 6.8 g of $ZnCl_2$, 3 g of citric acid, and deionized water to 1 liter.

LB medium was composed of 10 g of Bacto-Tryptone, 5 g of yeast extract, 10 g of sodium chloride, and deionized water to 1 liter.

LB plates were composed of 10 g of Bacto-Tryptone, 5 g of yeast extract, 10 g of sodium chloride, 15 g of Bacto-agar, and deionized water to 1 liter.

PDA plates were composed of potato infusion made by boiling 300 g of sliced (washed but unpeeled) potatoes in water for 30 minutes and then decanting or straining the broth through cheesecloth. Distilled water was then added until the total volume of the suspension was 1 liter. Then 20 g of dextrose and 20 g of agar powder were added. The medium was sterilized by autoclaving at 15 psi for 15 minutes (Bacteriological Analytical Manual, 8th Edition, Revision A, 1998).

TAE buffer was composed of 40 mM Tris base, 20 mM sodium acetate, and 1 mM disodium EDTA.

YP+2% glucose medium was composed of 1% yeast extract, 2% peptone, and 2% glucose in deionized water.

YP+2% maltose medium was composed of 10 g of yeast extract, 20 g of peptone, 20 g of maltose, and deionized water to 1 liter.

Example 1: Source of DNA Sequence Information for *Trichoderma reesei* Cellobiohydrolase I The genomic DNA sequence and deduced amino acid sequence of the *Trichoderma reesei* GH7 cellobiohydrolase I gene is shown in SEQ ID NO: 1 and SEQ ID NO: 2, respectively.

Genomic sequence information was generated by the U.S. Department of Energy Joint Genome Institute (JGI) and published by Martinez et al., 2008, *Nature Biotechnology* 26 (5): 553-560. The amino acid sequence of the full-length cellobiohydrolase I is publicly available from the National Center for Biotechnology Information (NCBI) and annotated as GenBank: EGR44817.1 (SEQ ID NO: 2). The cDNA sequence of the *Trichoderma reesei* cellobiohydrolase I gene is shown in SEQ ID NO: 31.

Based on the publicly available amino acid sequence, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 32) was synthesized by the GENEART® Gene Synthesis service (Life Technologies Corp., San Diego. CA, USA) with a 5' Bam HI restriction site, a 3' Hind III restriction site, and a Kozac consensus sequence (CACC) situated between the start codon and the Bam HI restriction site.

Example 2: Construction of an *Aspergillus oryzae* Expression Vector Containing a *Trichoderma reesei* cDNA Sequence Encoding Cellobiohydrolase I The kanamycin-resistant *E. coli* cloning vector provided by GENEART® Gene Synthesis encoding the *T. reesei* cellobiohydrolase I (SEQ ID NO: 4) was digested with Fast Digest Bam HI and Hind III (Fermentas Inc., Glen Burnie, MD, USA) according to manufacturer's instructions. The reaction products were isolated by 1.0% agarose gel electrophoresis using TAE buffer where a 1552 bp product band was excised from the gel and purified using an ILLUS-TRA™ GFX™ DNA Purification Kit (GE Healthcare Life Sciences, Brondby, Denmark).

The 1552 bp fragment was then cloned into pDau109 (WO 2005/042735) digested with Bam HI and Hind III using T4 DNA ligase (New England Biolabs, Ipswich, MA, USA). The Bam HI-Hind III digested pDau109 and the Bam HI/Hind III fragment containing the *T. reesei* cellobiohydrolase I coding sequence were mixed in a molar ratio of 1:3 (i.e., mass ratio approximately 2.5:1 or 20 ng:50 ng) and ligated with 50 units of T4 DNA ligase in 1× T4 DNA ligase buffer (New England Biolabs, Ipswich, MA, USA) with 1 mM ATP at 16° C. over-night in accordance with the manufacturer's instructions. Cloning of the *T. reesei* cellobiohydrolase I gene into the Bam HI-Hind III digested pDau109 resulted in transcription of the *T. reesei* cellobiohydrolase I gene under the control of a NA2-tpi double promoter. The NA2-tpi promoter is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, colonies were observed growing under selection on the LB ampicillin plates Insertion of the *T. reesei* cellobiohydrolase I gene into pDau109 was verified by PCR on colonies as described below using the following primers.

```
Primer F-pDau109
                              (SEQ ID NO: 51)
5'-CCCTTGTCGATGCGATGTATC-3'

Primer R-pDau109
                              (SEQ ID NO: 52)
5'-ATCCTCAATTCCGTCGGTCGA-3'
```

A 1.1λ REDDYMIX® Master Mix (Thermo Fisher Scientific, Roskilde, Denmark) was used for the PCR. The PCR solution was composed of 10 μl of 1.1λ REDDYMIX® Master Mix, 0.5 μl of primer F-pDau109 (10 μM), and 0.5

µl of primer R-pDau109 (10 µM). A toothpick was used to transfer a small amount of cells to the PCR solution. The PCR was performed using a PTC-200 DNA Engine programmed for 1 cycle at 94° C. for 3 minutes; 30 cycles each at 94° C. for 30 seconds, 50° C. for 1 minute, and 72° C. for 2 minutes; and 1 cycle at 72° C. for 1 minute. The PCR solution was then held at 15° C. until removed from the PCR machine.

The PCR products were analyzed by 1.0% agarose gel electrophoresis using TAE buffer where a 1860 bp PCR product band was observed confirming insertion of the *T. reesei* cellobiohydrolase I coding sequence into pDau109.

An *E. coli* transformant containing the *T. reesei* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pKHJN0036.

Example 3: Source of DNA Sequence Information for *Rasamsonia emersonii* Cellobiohydrolase I The genomic DNA sequence and deduced amino acid sequence of the wild-type *Rasamsonia emersonii* GH7 cellobiohydrolase I gene is shown in SEQ ID NO: 39 and SEQ ID NO: 40, respectively. The gene sequence is 99% identical to Genbank entry AF439935.4. The cDNA sequence and deduced amino acid sequence of the *Rasamsonia emersonii* cellobiohydrolase I gene is shown in SEQ ID NO: 53 and SEQ ID NO: 40, respectively.

Based on the cDNA sequence for *Rasamsonia emersonii* cellobiohydrolase I, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 54) was synthesized by the GENEART® Gene Synthesis service (Life Technologies Corp., San Diego. CA, USA) with a 5' Bam HI restriction site, a 3' Hind III restriction site, and a Kozac consensus sequence (CACC) situated between the start codon and the Bam HI restriction site.

Example 4: Construction of an *Aspergillus oryzae* Expression Vector Containing a *Rasamsonia emersonii* DNA Sequence Encoding Cellobiohydrolase I The kanamycin-resistant *E. coli* cloning vector provided by GENEART® Gene Synthesis encoding the *Rasamsonia emersonii* cellobiohydrolase I was digested with Fast Digest Bam HI and Hind III (Fermentas Inc., Glen Burnie, MD, USA) according to manufacturer's instructions. The reaction products were isolated by 1.0% agarose gel electrophoresis using TAE buffer where a 1375 bp product band was excised from the gel and purified using an ILLUSTRA™ GFX™ DNA Purification Kit.

The 1375 bp fragment was then cloned into pDau109 digested with Bam HI and Hind III using T4 DNA ligase. The Bam HI-Hind III digested pDau109 and the Bam HI/Hind III fragment containing the *T. reesei* cellobiohydrolase I coding sequence were mixed in a molar ratio of 1:3 (i.e., mass ratio approximately 2.5:1 or 20 ng:50 ng) and ligated with 50 units of T4 DNA ligase in 1× T4 DNA ligase buffer with 1 mM ATP at 16° C. over-night in accordance with the manufacturer's instructions. Cloning of the *Rasamsonia emersonii* cellobiohydrolase I gene into Bam HI-Hind III digested pDau109 resulted in the transcription of the

*Rasamsonia emersonii* cellobiohydrolase I gene under the control of a NA2-tpi double promoter.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Insertion of the *Rasamsonia emersonii* cellobiohydrolase I gene into pDau109 was verified by PCR on the transformants as described below using primers F-pDau109 and R-pDau109.

A 1.1× REDDYMIX® Master Mix (Thermo Fisher Scientific, Roskilde, Denmark) was used for the PCR. The PCR solution was composed of 10 µl of 1.1λ REDDYMIX® Master Mix, 0.5 µl of primer F-pDau109 (10 µM), and 0.5 µl of primer R-pDau109 (10 µM). A toothpick was used to transfer a small amount of cells to the PCR solution. The PCR was performed using a PTC-200 DNA Engine programmed for 1 cycle at 94° C. for 3 minutes; 30 cycles each at 94° C. for 30 seconds, 50° C. for 1 minute, and 72° C. for 2 minutes; and 1 cycle at 72° C. for 1 minute. The PCR solution was then held at 15° C. until removed from the PCR machine.

The PCR products were analyzed by 1.0% agarose gel electrophoresis using TAE buffer where a 1600 bp PCR product band was observed confirming insertion of the *Rasamsonia emersonii* cellobiohydrolase I coding sequence into pDau109.

An *E. coli* transformant containing the *Rasamsonia emersonii* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pKHJN0135.

Example 5: Construction of a Hybrid Polypeptide of *Rasamsonia emersonii* Cellobiohydrolase I with Linker and Carbohydrate Binding Module from *Trichoderma reesei* Cellobiohydrolase I (PC1-147)

The codon-optimized synthetic gene encoding the *T. reesei* (*H. jecorina*) cellobiohydrolase I is described in Example 1.

The codon-optimized synthetic gene encoding the *R. emersonii* cellobiohydrolase I is described in Example 3.

To generate a gene encoding a hybrid polypeptide of *R. emersonii* cellobiohydrolase I with linker and carbohydrate binding module (CBM) from *T. reesei* cellobiohydrolase I (SEQ ID NOs: 55 and 56 for the hybrid polypeptide DNA and amino acid sequences, respectively), a DNA fragment encoding *T. reesei* cellobiohydrolase I linker and CBM was assembled to the 3'-end of the gene encoding the *R. emersonii* cellobiohydrolase I using splicing overlap extension (SOE) PCR.

The DNA fragment encoding the *T. reesei* cellobiohydrolase I linker and CBM was amplified using primer F-SOE and primer R-pDau109 shown below.

```
Primer F-SOE:
                                    (SEQ ID NO: 57)
5'-GGTCC CATCA ACTCG ACATT CACAG CCTCG

GGTGG AAACC CTCCT GGCGG AAACC CTC-3'
```

-continued

```
Primer R-pDau109:
                              (SEQ ID NO: 58)
5'-ATCCTCAATTCCGTCGGTCGA-3'

Primer F-pDau109:
                              (SEQ ID NO: 59)
5'-CCACACTTCTCTTCCTTCCTCAATCCTC-3'
```

The amplification of the DNA fragment encoding the *T. reesei* cellobiohydrolase I linker and CBM was performed using a PHUSION® High-Fidelity PCR Kit. The PCR solution was composed of 10 μl of 5λ HF buffer, 1 μl of dNTPs (10 mM), 0.5 μl of PHUSION® DNA polymerase (0.2 units/μl), 0.25 μl of primer F-SOE (100 μM), 0.25 μl of primer R-pDau109 (100 μM), 10 μl of template DNA (pDAu222—*T. reesei* cellobiohydrolase I, 1 ng/μl), and 28 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 405 bp PCR fragment encoding the *T. reesei* a linker and CBM was excised from the gel and purified using a MinElute Gel Extraction Kit (QIAGEN Inc., Valencia, CA, USA).

A DNA fragment encoding the *R. emersonii* cellobiohydrolase I was amplified using primer F-pDau109 and primer R-pDau109 above.

The amplification of the DNA fragment encoding the *R. emersonii* wild-type cellobiohydrolase I was performed using a PHUSION® High-Fidelity PCR Kit. The PCR solution was composed of 10 μl of 5λ HF buffer, 1 μl of dNTPs (10 mM), 0.5 μl of PHUSION® DNA polymerase (0.2 units/μl), 0.25 μl of primer F-pDAu109 (100 μM), 0.25 μl of primer R-pDau109 (100 μM), 10 μl of template DNA (pDAu222-*R. emersonii* cellobiohydrolase I, 1 ng/μl), and 28 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 1600 bp fragment encoding the *R. emersonii* wild-type cellobiohydrolase I was excised from the gel and purified using a MinElute Gel Extraction Kit.

The two purified DNA fragments were assembled using SOE PCR and a PHUSION® High-Fidelity PCR Kit. The PCR solution was composed of 10 μl of 5× HF buffer, 1 μl of dNTPs (10 mM), 0.5 μl of PHUSION® DNA polymerase (0.2 units/μl), 0.25 μl of primer F-pDAu109 (100 μM), 10 μl of gel purified fragment encoding *T. reesei* cellobiohydrolase 1 linker and CBM, 2 μl of DNA fragment encoding *R. emersonii* cellobiohydrolase I, and 26 μl of deionized water in a total volume of 50 μl. The PCR was performed using a GeneAmp® PCR System 9700 programmed for 1 cycle at 98° C. for 30 seconds; and 30 cycles each at 98° C. for 20 seconds, 55° C. for 30 seconds, and 72° C. for 1 minute. The PCR solution was then held at 8° C. until removed from the PCR machine.

The PCR generated DNA fragment was then digested with Bam HI (New England Biolabs, Ipswich, MA, USA) and Hind III (New England Biolabs, Ipswich, MA, USA) as follows. Forty μl of PCR product were mixed with 5 μl buffer 2 (New England Biolabs, Ipswich, MA, USA), 1 μl of Bam HI, and 1 μl of Hind III and incubated for 4 hours at 37° C. The resulting DNA product was submitted to 1% agarose gel electrophoresis using TAE buffer. A band of approximately 1567 bp was excised from the gel and purified using a MinElute Gel Extraction Kit.

The purified 1567 bp fragment encoding the *R. emersonii* cellobiohydrolase I with linker and carbohydrate binding module (CBM) from *T. reesei* cellobiohydrolase I was cloned into pDAu109 digested with Bam HI and Hind III using T4 DNA ligase. The Bam HI-Hind III digested pDau109 and the Bam HI/Hind III fragment containing the *R. emersonii* cellobiohydrolase I with linker and carbohydrate binding module (CBM) from *T. reesei* cellobiohydrolase I coding sequence were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Two transformants were cultivated in LB medium supplemented with 0.15 mg of ampicillin per ml and plasmids were isolated using a QIAPREP® Spin Miniprep Kit.

The insertion of the DNA fragment encoding the *R. emersonii* cellobiohydrolase I with linker and carbohydrate binding module (CBM) from *T. reesei* cellobiohydrolase I into pDAu109 was verified by sequencing. The isolated plasmids were sequenced using an Applied Biosystems 3730xl DNA Analyzer with vector primers F-pDau109 and R-pDau109 in order to determine a representative plasmid that was free of PCR errors and contained the correct insertion.

One plasmid clone free of PCR errors and containing the DNA fragment encoding the *R. emersonii* cellobiohydrolase I with linker and carbohydrate binding module (CBM) from *T. reesei* cellobiohydrolase I was chosen and designated plasmid pE147. The corresponding hybrid polypeptide was designated as PC1-147.

Example 6: Site-Directed Mutagenesis of the Hybrid Polypeptide of *Rasamsonia emersonii* Cellobiohydrolase I with Linker and Carbohydrate Binding Module from *Trichoderma reesei* Cellobiohydrolase I (PC1-499, PC1-500)

The plasmid pE147 containing the DNA fragment encoding the hybrid polypeptide of *Rasamsonia emersonii* cellobiohydrolase I with linker and carbohydrate binding module from *Trichoderma reesei* cellobiohydrolase I was described in Example 5.

To generate the hybrid polypeptide PC1-499 containing a Y→W substitution corresponding to Y32W of the carbohydrate binding module of the hybrid polypeptide PC1-147 supra, a TAT codon encoding position 515 of SEQ ID NO: 56 was replaced with a TGG codon in the gene encoding PC1-147. The mutant DNA sequence and corresponding polypeptide sequence are designated as SEQ ID NO: 60 and SEQ ID NO: 61, respectively.

To generate the hybrid polypeptide PC1-500 containing a Y→W substitution corresponding to Y5W of the carbohydrate binding module of the hybrid polypeptide PC1-147 supra, a TAC codon encoding position 488 of SEQ ID NO:

56 was replaced with a TGG codon in the gene encoding PC1-147. The mutant DNA sequence and corresponding polypeptide sequence are designated as SEQ ID NO: 62 and SEQ ID NO: 63, respectively.

Two synthetic primers for each site-directed mutagenesis were designed as shown below using an SOE primer design tool. The introduced site-directed mutation changed a TAT codon encoding position 515 of SEQ ID NO: 56 to a TGG codon and a TAC codon encoding position 488 of SEQ ID NO: 56 to a TGG codon.

```
    Primer F-Y497W:
                                    (SEQ ID NO: 64)
    5'-CTGTC AGGTC TTGAA CCCTT ACTGG

TCGCA GTGTC TCTAA G-3'

Primer R-Y497W:
                                    (SEQ ID NO: 65)
    5'-GTAAG GGTTC AAGAC CTGAC AGGTT

GTGCC GG-3'

Primer F-Y470W:
                                    (SEQ ID NO: 66)
    5'-CTGGA CCGAC CCAGT CCCAC TGGGG

ACAGT GTGGA GGCAT CGG-3'

Primer R-Y470W:
                                    (SEQ ID NO: 67)
    5'-GTGGG ACTGG GTCGG TCCAG GGGAC GAACC-3'
```

Site-directed mutagenesis was facilitated by PCR amplifications of the pDau109 vector containing the coding sequence for the hybrid polypeptide PC1-147. The gene was previously cloned into Bam HI-Hind III digested pDau109 resulting in transcription of the gene under the control of a NA2-tpi double promoter.

The mutations were introduced by PCR using a PHUSION® High-Fidelity PCR Kit. The PCR solution was composed of 10 µl of 5× HF buffer, 1 µl of dNTPs (10 mM), 0.5 µl of PHUSION® DNA polymerase (0.2 units/µl), 0.25 µl of primer F-Y497W (100 µM), 0.25 µl of primer R-Y497W (100 µM), 10 µl of plasmid pE147 DNA (1 ng/µl), and 28 µl of deionized water in a total volume of 50 µl. For the TAC to TGG mutation 0.25 µl of primer F-Y470W (100 µM), 0.25 µl of primer R-Y470W (100 µM) were used. The PCR was performed using a GeneAmp® PCR System 9700 programmed for 1 cycle at 98° C. for 30 seconds; and 19 cycles each at 98° C. for 30 seconds, 55° C. for 1 minute, and 72° C. for 4 minutes. The PCR solution was then held at 8° C. until removed from the PCR machine.

Following the PCR, 10 units of Dpn I were added directly to the PCR solution and incubated at 37° C. for 1 hour. Then 1 µl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.15 mg of ampicillin per ml and plasmids were isolated using a QIAPREP® Spin Miniprep Kit.

The isolated plasmids were sequenced using an Applied Biosystems 3730xl DNA Analyzer with primers F-p147, F-Central1, R-Central2 and R-pDau109, in order to determine a representative plasmid that was free of PCR errors and contained the desired mutations.

```
    Primer F-p147
                                    (SEQ ID NO: 68)
    5'CCACACTTCTCTTCCTTCCTCAATCCTC-3'

Primer F-Central1
                                    (SEQ ID NO: 69)
    5'GTGAG GCGAA CGTGG AAGGA TG-3'

Primer R-Central2
                                    (SEQ ID NO: 70)
    5'-GTACC TGTGT CCGTG CCGTC ATCTG-3'

Primer R-pDau109
                                    (SEQ ID NO: 71)
    5'-ATCCT CAATT CCGTC GGTCG A-3'
```

One plasmid clone free of PCR errors and containing the TAT to TGG mutation was chosen and designated plasmid pE499. The corresponding fusion polypeptide was designated as PC1-499.

One plasmid clone free of PCR errors and containing the TAC to TGG mutation was chosen and designated plasmid pE500. The corresponding fusion polypeptide was designated as PC1-500.

Example 7: Expression of Hybrid Polypeptides PC1-147, PC1-499 and PC1-500

The expression plasmids pE147, pE499 and pE500 (supra) were transformed into *Aspergillus oryzae* MT3568 protoplasts according to Christensen et al., 1988, supra and WO 2004/032648. *A. oryzae* MT3568 protoplasts were prepared according to the method of EP 0238023 B1, pages 14-15.

Transformants were purified on COVE sucrose plates without CsCl through single conidia. Spores of the transformants were inoculated into 96 deep well plates containing 0.50 ml of YP+2% maltose+0.5% glucose medium and incubated stationary at 34° C. for 6 days. Production of hybrid polypeptides by the transformants were analyzed from culture supernatants of the 96 deep well cultivations. Expression was verified by measuring released reducing sugars from hydrolysis of microcrystalline cellulose. The hydrolysis was performed in 96 well microtiter plates (NUNC Thermo Fisher Scientific, Roskilde, Denmark) at 25° C. and 1100 rpm. Each hydrolysis reaction mixture contained 167 µl of microcrystalline cellulose at 90 g/liter in 50 mM sodium acetate pH 5.0, 0.01% TRITON® X-100, 20 µl of culture supernatant, and 63 µl of 50 mM sodium acetate pH 5.0, 0.01% TRITON® X-100. The plates were sealed with tape. The hydrolysis reaction was stopped by spinning the plate at 3500 rpm for 3 minutes. Then 50 µl of the reaction supernatant were added to 75 µl of stop solution in a 96 well PCR plate (Thermo Fisher Scientific, Roskilde, Denmark). The stop solution was composed of 15 mg/ml 4-hydroxybenzhydrazide (Sigma Chemical Co., Inc., St. Louis, MO, USA), 50 mg/ml K-Na-tartrate (Sigma Chemical Co., Inc., St. Louis, MO, USA) in 2% (w/v) NaOH. The plate was sealed with a lid and the mixture was incubated at 95° C. for 10 minutes and 5 minutes at 20° C. Then 100 µl was transferred to a microtiter plate and absorbance at 410 nm was measured using a SPECTRAMAX® Plus 384 (Molecular Devices, Sunnyvale, CA, USA). The concentration of reducing sugar was proportional to the absorbance at 410 nm of the oxidized 4-hydroxybenzhydrazide. The reducing sugar content in the culture supernatants was measured by adding 4 µl of culture supernatant to a mixture of 75 µl of stop solution and 46 µl of milliQ water in a 96 well PCR plate. The plate was sealed with a lid and the mixture was incubated at 95° C. for 10 minutes and 5 minutes at 20° C. Then 100 µl was transferred to a microtiter plate and the absorbance at 410 nm was measured. The absorbance at 410 nm from the cell culture supernatant was subtracted from the absorbance at 410 nm of the hydrolysis reaction, to measure the amount of reducing sugar released by the enzymes.

Based on the level of hydrolysis of the microcrystalline cellulose one transformant for each of the hybrid polypeptides PC1-147, PC1-499 and PC1-500 was selected and designated *A. oryzae* PC1-147, *A. oryzae* PC1-499 and *A. oryzae* PC1-500, respectively.

For larger scale production, *A. oryzae* PC1-147 or *A. oryzae* PC1-499 or PC1-500 spores were spread onto COVE sucrose slants and incubated for five days at 37° C. The confluent spore slants were washed twice with 5 ml of G2-Gly medium. The spore suspensions were then used to inoculate 500 ml flasks containing 150 ml of G2-Gly medium. These pre-cultures were incubated at 30° C. with constant shaking at 150 rpm. After one day, each of the pre-cultures was used to inoculate four 500 ml flasks containing 150 ml of DAP-4C medium. At day four post-inoculation, the culture broths were collected by filtration through a bottle top MF75 Supor MachV 0.2 µm PES filter.

Example 8: Purification of Hybrid Polypeptides PC1-147, PC1-499 and PC1-500

The fermentation broths were filtered through a PES Bottle top filter with a 0.22 µm cut-off. Ammonium sulphate was added to the filtered fermentation broths to a concentration of 1.8 M.

The desired hybrid polypeptides were purified from the fermentation broths by HIC/affinity chromatography followed by IEX/affinity chromatography.

In the HIC/affinity chromatographic step, the fermentation broths were applied to a 200 ml Phenyl SEPHAROSE® 6 Fast Flow column (high sub) (GE Healthcare, Piscataway, NJ, USA) which had been pre-equilibrated with 1.8 M ammonium sulphate, 25 mM HEPES pH 7.0. After applying the sample, the column was washed with 2 column volumes of 1.8 M ammonium sulphate followed by 1 column volume of 0.54 M ammonium sulphate. The bound proteins were batch eluted with 25 mM HEPES pH 7.0.

The elution of the protein was monitored at 280 nm. Fractions with high 280 nm absorbance were analyzed on SDS-PAGE using 12-well NUPAGE® 4-12% Bis-Tris gel (GE Healthcare, Piscataway, NJ, USA) for their cellobiohydrolase I content. Fractions with high content of this protein were pooled and collected for further purification. The pooled fractions were desalted on a SEPHADEX™ G-25 (medium) column (GE Healthcare, Piscataway, NJ, USA) equilibrated with 25 mM MES pH 6.0. The elution of the protein was monitored at 280 nm and fractions with high absorbance at 280 nm were chosen for the second chromatographic step.

The pooled fractions were applied to the 60 ml RESOURCE™ 15Q column (GE Healthcare, Piscataway, NJ, USA) equilibrated with 25 mM MES pH 6.0 and bound proteins were eluted with a linear 100-200 mM sodium chloride gradient for 1.5 column volumes followed by 1.5 column volumes of 300 mM sodium chloride, followed by 1.5 column volumes of 1 M sodium chloride. The elution of the protein was monitored at 280 nm and fractions with high absorbance at 280 nm were analyzed on SDS-PAGE.

Fractions with high content of cellobiohydrolase I were pooled.

Example 9: Activity Measurement on Microcrystalline Cellulose of Hybrid Polypeptides PC1-147, PC1-499 and PC1-500

The activities of the purified hybrid polypeptides PC1-147, PC1-499 and PC1-500 (supra) were compared to the purified wild-type *R. emersonii* cellobiohydrolase I using washed microcrystalline cellulose (AVICEL® PH101; Sigma-Aldrich, St. Louis, MO, USA) as a substrate (see PCT/US2014/022068).

The purified hybrid polypeptides were diluted in 50 mM sodium acetate, 2 mM $CaCl_2$) pH 5. The diluted hybrid polypeptides and β-glucosidase were added to each well (microwell plate 96F 26960 Thermo scientific). Washed AVICEL then was added to each well and the microtiter plate was quickly transferred to a thermomixer (eppendorf) and incubated for 24 hours at 1100 rpm and 50° C. or 60° C. The final concentration of hybrid polypeptides in the reaction was 3 µM and the concentration of AVICEL was 76 g/l. The reaction was stopped by centrifugation at 3500 rpm for 3 min at 5° C. (Hereaus multifuge 3 S-R). The supernatants diluted and transferred to PCR sample tubes (Thermoscientific 0.2 ml non-skirtet 96-well PCR plate AB0600). PAH-BAH (4-hydroxy-benzhydrazid) (Sigma, H 9882) was dissolved in buffer (0.18 M K-Na-tartrate (Merck, 1.08087) and 0.5 M NaOH) to make a 15 mg/ml solution. 75 µl of the PAHBAH solution was added to the supernatants in the PCR samples tubes.

The PCR sample tubes were placed in a Peltier Thermal Cycler and incubated at 95° C. for 10 min and 20° C. for 5 min. After incubation 100 µl were transferred to a 96 well microtiter plate (microwell plate 96F 26960 Thermo scientific) and the absorbance was measured at 410 nm. For each run a standard was included. The standard used was glucose diluted in 50 mM sodium acetate, 2 mM $CaCl_2$) pH 5 to a concentration of 0.008, 0.016, 0.0312, 0.0625, 0.125, 0.25, 0.5, 1 mM. In addition to the standard, a blank (without cellobiohydrolase) for each run was included. For all the measurement, the blank measurement was subtracted. The absorbance data were normalized to glucose concentration using the standards.

The results as shown in FIG. 2 demonstrated that at 50° C., the hybrid polypeptides PC1-500 (containing an *R. emersonii* cellobiohydrolase I catalytic domain linked to a *T. reesei* carbohydrate binding module variant with a substitution corresponding to Y5W of the CBM) and PC1-499 (containing an *R. emersonii* cellobiohydrolase I catalytic domain linked to a *T. reesei* carbohydrate binding module variant with a substitution corresponding to Y32W of the CBM) had an approximately 145% and 124% increase, respectively, toward microcrystalline cellulose compared to the wild-type cellobiohydrolase I and an increase of 57% and 44%, respectively, compared with the hybrid polypeptide lacking either substitution corresponding to Y5W or Y32W of the CBM.

The results as shown in FIG. 3 demonstrated that at 60° C., the hybrid polypeptides PC1-500 and PC1-499 showed an increase of 209% and 186%, respectively, compared to the wild-type cellobiohydrolase I and an increase of 34% and 24%, respectively, compared with the hybrid polypeptide lacking either substitution corresponding to Y5W or Y32W of the CBM.

Example 10: Pretreated Corn Stover Hydrolysis
Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of the PCS to 5.0 by addition of 10 M NaOH with extensive mixing, and then autoclaving for 20 minutes at 120° C. The dry weight of the whole slurry PCS was 29%.

A 96-well plate was generated by machining a teflon plate of depth ¼ inch with 96, cone-shaped wells, diameter ¼ inch at the upper surface and diameter ⅛ inch at the lower surface. The center of each well was at an equivalent position to the center of a corresponding well in a standard 96-well microtiter plate, approximately 23/64 inch on center. The resulting volume of each well was approximately 135 μl. This 96-well aluminum plate is hereinafter referred to as the "fill plate". The pH-adjusted corn stover was used to fill the holes in the fill plate by applying a suitable volume of the corn stover to the upper surface of the plate, then using a spatula to spread the material over the surface and into the holes. Holes were deemed sufficiently full when corn stover was extruded through the hole in the bottom surface, forming noodle-like tubes. A MULTISCREEN® Column Loader Scraper (Millipore) held perpendicular to the fill plate surface was used to scrape excess corn stover from the top and bottom surfaces of the fill plate, leaving the surfaces of the corn stover in each well flush with the surfaces of the fill plate. The fill plate was then placed on the top of a 2.2 ml deep well plate (Axygen, Union City, CA, USA) with the top surface adjacent to the open end of the well plate (e.g. the top of the well plate), and the wells aligned with the corn stover-filled holes in the fill plate. The fill plate was secured in this position, and the assembly centrifuged at 2500 rpm (1350×g) for 5 minutes in a Sorvall Legend RT+(Thermo Scientific, Waltham, MA, USA). Following centrifugation, the corn stover had been transferred to the deep well plate. A 3 mm glass bead (Fisher Scientific, Waltham, MA, USA) was placed in each well for mixing.

The hydrolysis of PCS was conducted in a total reaction volume of 0.2 ml. The hydrolysis was performed with 50 mg of insoluble PCS solids containing 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 20 μl to 50 μl, for a final volume of 0.2-0.50 ml in each reaction. The plate was then sealed using an ALPS-300™ plate heat sealer (Abgene, Epsom, United Kingdom), mixed thoroughly, and incubated at a specific temperature for 72 hours.

Following hydrolysis, samples were filtered using a 0.45 μm MULTISCREEN® 96-well filter plate (Millipore, Bedford, MA, USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, CA, USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, CA, USA) calibrated by pure sugar samples. The resultant glucose and cellobiose equivalents were used to calculate the percentage of cellulose conversion for each reaction.

Glucose and cellobiose were measured individually. Measured sugar concentrations were adjusted for the appropriate dilution factor. The net concentrations of enzymatically-produced sugars from unwashed PCS were determined by adjusting the measured sugar concentrations for corresponding background sugar concentrations in unwashed PCS at zero time point. All HPLC data processing was performed using MICROSOFT EXCEL™ software (Microsoft, Richland, WA, USA).

The degree of glucose conversion to glucose was calculated using the following equation: % cellulose conversion= (glucose concentration)/(glucose concentration in a limit digest)×100. In order to calculate % glucose conversion, a 100% conversion point was set based on a cellulase control (100 mg of *T. reesei* cellulase supplemented with *Thermoascus aurantiacus* GH61A polypeptide, *Aspergillus fumigatus* GH10 xylanase (xyn3), and *Talaromyces emersonii* beta-xylosidase per gram cellulose). Quadruplicate data points were averaged and standard deviation was calculated.

Example 11: Preparation of an Enzyme
Composition without Cellobiohydrolase I

The *Talaromyces leycettanus* GH6 cellobiohydrolase II (GENESEQP:AZY49446) was prepared recombinantly in *Aspergillus oryzae* as described in WO 2012/103288. The filtered broth of the *Talaromyces leycettanus* GH6 cellobiohydrolase II was concentrated and buffer exchanged into 20 mM Tris pH 8.0 using a 400 ml SEPHADEX™ G-25 column (GE Healthcare, United Kingdom). The fractions were pooled, and 3 M ammonia sulfate, 20 mM Tris pH 8.0 was added to the desalted protein to a final concentration of 1.2 M ammonia sulfate, 20 mM Tris pH 8.0. The protein was loaded onto a Phenyl Sepharose™ 6 Fast Flow column (high sub) (GE Healthcare, Piscataway, NJ, USA) equilibrated in 20 mM Tris pH 8.0 with 1.2 M ammonium sulfate, and bound proteins were eluted with 20 mM Tris pH 8.0 with no ammonium sulfate. Fractions were analyzed by 8-16% Tris-HCl SDS-PAGE gels (Bio-Rad, Hercules, CA, USA), and pooled. The pooled protein was buffer exchanged into 20 mM MES pH 6.0 using a Vivaflow 200 with 10 kDa molecular weight cut-off tangential flow membrane (Sartorius, Bohemia, NY, USA).

The *Trichoderma reesei* GH5 endoglucanase II (GENESEQP:AZI04858) was prepared recombinantly according to WO 2011/057140 using *Aspergillus oryzae* as a host. The filtered broth of the *T. reesei* endoglucanase II was desalted and buffer-exchanged into 20 mM Tris pH 8.0 using a tangential flow concentrator (Pall Filtron, Northborough, MA, USA) equipped with a 10 kDa polyethersulfone membrane (Pall Filtron, Northborough, MA, USA).

*Thermoascus aurantiacus* CGMCC 0583 GH61A polypeptide having cellulolytic enhancing activity (GENESEQP: AEC05922) was recombinantly prepared according to WO 2005/074656 using *Aspergillus oryzae* JaL250 as a host. The broth was filtered using a 0.22 μm EXPRESS™ Plus Membrane (Millipore, Bedford, MA, USA).

The *Aspergillus fumigatus* GH10 xylanase (xyn3) (GENESEQP:AZI04884) was prepared recombinantly according to WO 2006/078256 using *Aspergillus oryzae* BECh2 (WO 2000/39322) as a host. The filtered broth of the *A. fumigatus* xylanase was desalted and buffer-exchanged into 50 mM sodium acetate pH 5.0 using a HIPREP® 26/10 Desalting Column (GE Healthcare, Piscataway, NJ, USA).

The *Aspergillus fumigatus* Cel3A beta-glucosidase 4M mutant (GENESEQP:AZU67153) was recombinantly prepared according to WO 2012/044915. The filtered broth of *Aspergillus fumigatus* Cel3A beta-glucosidase 4M was concentrated and buffer exchanged using a tangential flow concentrator (Pall Filtron, Northborough, MA, USA) equipped with a 10 kDa polyethersulfone membrane (Pall Filtron, Northborough, MA, USA) with 50 mM sodium acetate pH 5.0 containing 100 mM sodium chloride.

The *Talaromyces emersonii* CBS 393.64 beta-xylosidase (GENESEQP:AZI04896) was prepared recombinantly according to Rasmussen et al., 2006, *Biotechnology and Bioengineering* 94: 869-876 using *Aspergillus oryzae* JaL355 as a host (WO 2003/070956). The filtered broth was concentrated and desalted with 50 mM sodium acetate pH 5.0 using a tangential flow concentrator equipped with a 10 kDa polyethersulfone membrane (Pall Filtron, Northborough, MA, USA).

The protein concentration for each of the monocomponents described above was determined using a Microplate BCA™ Protein Assay Kit (Thermo Fischer Scientific, Waltham, MA, USA) in which bovine serum albumin was used as a protein standard. An enzyme composition was prepared composed of each monocomponent as follows: 39.7% *Talaromyces leycettanus* GH6 cellobiohydrolase II, 15.9% *Trichoderma reesei* GH5 endoglucanase II, 23.8% *Thermoascus aurantiacus* GH61A polypeptide, 7.9% *Aspergillus fumigatus* GH10 xylanase, 7.9% *Aspergillus fumigatus* beta-glucosidase, and 4.8% *Talaromyces emersonii* beta-xylosidase. The enzyme composition is designated herein as "cellulolytic enzyme composition without cellobiohydrolase I".

Example 12: Comparison of the Effect of Hybrid Polypeptides PC1-147, PC1-499 and PC1-500 on the Hydrolysis of Unwashed PCS by a Cellulase Enzyme Composition The hybrid polypeptides PC1-499 and PC1-500 (containing a substitution corresponding to Y32W and Y5W of the cellulose binding module, respectively) were added to the cellulolytic enzyme composition without cellobiohydrolase I (supra) at 35° C., 50° C. and 60° C. using unwashed PCS as a substrate, and compared against the hybrid polypeptide PC1-147 (lacking either substitution corresponding to Y5W or Y32W of the cellulose binding module). Each cellobiohydrolase I was added individually at 3.33 mg enzyme protein per g cellulose to 5.67 mg enzyme protein of the cellulase enzyme composition without cellobiohydrolase I per g cellulose.

The assay was performed as described in supra. The reactions with unwashed PCS (20% total solids) were conducted for 72 hours at 35° C., 50° C. and 60° C. in 50 mM sodium acetate pH 5.0 buffer containing 1 mM manganese sulfate. All reactions were performed in quadruplicate and shaking at 200 rpm throughout the hydrolysis.

The results shown in FIG. 4 demonstrated that the cellulase enzyme composition containing the hybrid polypeptide PC1-499 (containing an *R. emersonii* cellobiohydrolase I catalytic domain linked to a *T. reesei* carbohydrate binding module (CBM) variant with a substitution corresponding to Y32W of the CBM) had significantly higher cellulose conversion at all temperatures compared to the cellulase enzyme composition that included the hybrid polypeptide PC1-147 lacking either substitution corresponding to Y5W or Y32W of the CBM. In addition, the hybrid polypeptide PC1-500 (containing an *R. emersonii* cellobiohydrolase I catalytic domain linked to a *T. reesei* carbohydrate binding module variant with a substitution corresponding to Y5W of the CBM) had significantly higher cellulose conversion at all temperatures compared to PC1-147.

Example 13: Site-Directed Mutagenesis of the Hybrid Polypeptide of *Rasamsonia emersonii* Cellobiohydrolase I with Linker and Carbohydrate Binding Module from *Trichoderma reesei* Cellobiohydrolase I (PC1-668)

The plasmid pE147 contains the DNA fragment encoding the hybrid polypeptide of *Rasamsonia emersonii* cellobiohydrolase I with linker and carbohydrate binding module from *Trichoderma reesei* cellobiohydrolase I was described in Example 5.

To generate the hybrid polypeptide PC1-668 containing a Y→W substitution corresponding to Y13W of the carbohydrate binding module of the hybrid polypeptide PC1-147 supra, a TAT codon encoding position 496 of SEQ ID NO: 56 was replaced with a TGG codon in the gene encoding PC1-147. The mutant DNA sequence and corresponding polypeptide sequence are designated as SEQ ID NO: 72 and SEQ ID NO: 73, respectively.

Two synthetic primers for each site-directed mutagenesis were designed as shown below using an SOE primer design tool. The introduced site-directed mutation changed a TAT codon encoding position 496 of SEQ ID NO: 56 to a TGG codon.

```
Primer F-Y478W:
                                (SEQ ID NO: 74)
5'GGACA GTGTG GAGGC ATCGG TTGGT

CCGGT CCGAC CGTCT GTGC-3'

Primer R-Y478W:
                                (SEQ ID NO: 75)
5'-ACCGA TGCCT CCACA CTGTC CGTAG

TGGGA CT-3'
```

Site-directed mutagenesis was facilitated by PCR amplifications of the pDau109 vector containing the coding sequence for the hybrid polypeptide PC1-147. The gene was previously cloned into Bam HI-Hind III digested pDau109 resulting in transcription of the gene under the control of a NA2-tpi double promoter.

The mutation was introduced by PCR using a PHUSION® High-Fidelity PCR Kit. The PCR solution was composed of 10 μl of 5× HF buffer, 1 μl of dNTPs (10 mM), 0.5 μl of PHUSION® DNA polymerase (0.2 units/μl), 0.25 μl of primer F-Y478W (100 μM), 0.25 μl of primer R-Y478W (100 μM), 10 μl of plasmid pE147 DNA (1 ng/μl), and 28 μl of deionized water in a total volume of 50 μl. The PCR was performed using a GeneAmp® PCR System 9700 programmed for 1 cycle at 98° C. for 30 seconds; and 19 cycles each at 98° C. 15 for 30 seconds, 55° C. for 1 minute, and 72° C. for 4 minutes. The PCR solution was then held at 8° C. until removed from the PCR machine.

Following the PCR, 10 units of Dpn I were added directly to the PCR solution and incubated at 37° C. for 1 hour. Then 1 μl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.15 mg of ampicillin per ml and plasmids were isolated using a QIAPREP® Spin Miniprep Kit.

The isolated plasmids were sequenced using an Applied Biosystems 3730xl DNA Analyzer with primers F-p147, F-Central1, R-Central2 and R-pDau109, in order to determine a representative plasmid that was free of PCR errors and contained the desired mutations.

```
Primer F-p147
                              (SEQ ID NO: 68)
5'-CCACA CTTCT CTTCC TTCCT CAATC CTC-3'

Primer F-Central1
                              (SEQ ID NO: 69)
5'-GTGAG GCGAA CGTGG AAGGA TG-3'

Primer R-Central2
                              (SEQ ID NO: 70)
5'GTACC TGTGT CCGTG CCGTC ATCTG-3'

Primer R-pDau109
                              (SEQ ID NO: 71)
5'-ATCCT CAATT CCGTC GGTCG A-3'
```

One plasmid clone free of PCR errors and containing the TAT to TGG mutation was chosen and designated plasmid pE668. The corresponding fusion polypeptide was designated as PC1-668.

Example 14: Source of DNA Sequence Information for *Aspergillus fumigatus* Cellobiohydrolase I The genomic DNA sequence and deduced amino acid sequence of the *Aspergillus fumigatus* Af293 GH7 cellobiohydrolase I gene is shown in SEQ ID NO: 76 and SEQ ID NO: 78, respectively. Genomic sequence information was generated by The Institute for Genomic Research, Rockville, Maryland 20850, USA and published by Nierman, W. C. et al., 2005, *Nature* 438 (7071): 1151-1156. The amino acid sequence of the full-length cellobiohydrolase I is publicly available from the National Center for Biotechnology Information (NCBI) and annotated as GenBank: EAL89006.1 The cDNA sequence and deduced amino acid sequence of the *Aspergillus fumigatus* cellobiohydrolase I gene is shown in SEQ ID NO: 77 and SEQ ID NO: 78, respectively.

Based on the publicly available amino acid sequence, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 79) was synthesized by the GENEART® Gene Synthesis service (Life Technologies Corp., San Diego. CA, USA) with a 5' Bam HI restriction site, a 3' Hind III restriction site, and a Kozac consensus sequence (CACC) situated between the start codon and the Bam HI restriction site.

Example 15: Construction of an *Aspergillus oryzae* Expression Vector Containing an *Aspergillus fumigatus* DNA Sequence Encoding Cellobiohydrolase I The ampicillin-resistant *E. coli* cloning vector provided by GENEART® Gene Synthesis encoding the *A. fumigatus* cellobiohydrolase I (Example 14) was digested with Bam HI and Hind III (New England Biolabs, MA, USA) according to manufacturer's instructions. The reaction products were isolated by 1.0% agarose gel electrophoresis using TAE buffer where a 1606 bp product band was excised from the gel and purified using a MinElute Gel Extraction Kit (QIAGEN Inc., Valencia, CA, USA).

The purified 1606 bp fragment encoding the *A. fumigatus* cellobiohydrolase I was cloned into pDau109 (WO 2005/042735) digested with Bam HI and Hind III using T4 DNA ligase (New England Biolabs, MA, USA). The Bam HI-Hind III digested pDau109 and the Bam HI/Hind III fragment containing the *A. fumigatus* cellobiohydrolase I were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

Cloning of the *A. fumigatus* cellobiohydrolase I gene into the Bam HI-Hind III digested pDau109 will result in transcription of the *A. fumigatus* cellobiohydrolase I gene under the control of a NA2-tpi double promoter. The NA2-tpi promoter is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligation mixture was transformed into ONE SHOT® TOP10F Chemically Competent *E. coli* cells according to the manufacturer's protocol and spread onto LB plates supplemented with 0.1 mg of ampicillin per ml. After incubation at 37° C. overnight, colonies were observed growing under selection on the LB ampicillin plates.

Insertion of the *A. fumigatus* cellobiohydrolase I gene into pDau109 was verified by DNA sequencing. The isolated plasmids were sequenced using an Applied Biosystems 3730xl DNA Analyzer with vector primers and *A. fumigatus* cellobiohydrolase I gene specific primers, shown below, in order to determine a representative plasmid that was free of PCR errors and contained the desired insert.

```
Primer F-pDau109
                              (SEQ ID NO: 59)
5'-CCCTT GTCGA TGCGA TGTAT C-3'

Primer R-pDau109
                              (SEQ ID NO: 58)
5'-ATCCT CAATT CCGTC GGTCG A-3'

Primer F-pE596
                              (SEQ ID NO: 80)
5'-GTGAT ACACC CGGAC AGGTG ATGTG-3'

Primer R-pE596
                              (SEQ ID NO: 81)
5'-CCATA TCGAT CCGAC GAGTA GGTTC-3'
```

An *E. coli* transformant containing the *A. fumigatus* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pE596 and the corresponding polypeptide was designated as AC1-596.

Example 16: Construction of an *Aspergillus oryzae* Expression Vector Containing a *Rasamsonia byssochlamydoides* DNA Sequence Encoding Cellobiohydrolase I The genomic DNA sequence and deduced amino acid sequence of the *Rasamsonia byssochlamydoides* (*Talaromyces byssochlamydoides*) strain CB5413.71 GH7 cellobiohydrolase I gene is shown in SEQ ID NO: 82 and SEQ ID NO: 83, respectively. The GH7 cellobiohydrolase I gene is 1507 bp including the stop codon with two predicted introns (604 to 667 and 1236 to 1310). Cloning of the *R. byssochlamydoides* GH7 gene into pDau109 vector is described patent WO2012/103300 (the content of which is hereby encorporated by reference). The plasmid of pDau109 containing the *R. byssochlamydoides* GH7 gene was designated pE637.

Example 17: Construction of a Fusion Polypeptide of *Rasamsonia byssochlamydoides* Cellobiohydrolase I with Linker and Carbohydrate Binding Module from *Aspergillus fumigatus* Cellobiohydrolase I (RC1-638)

The codon-optimized synthetic gene encoding the *Aspergillus fumigatus* cellobiohydrolase I is described in Examples 14 and 15.

The gene encoding the *R. byssochlamydoides* cellobiohydrolase I is described in Example 16.

To generate a gene encoding a fusion polypeptide of *R. byssochlamydoides* cellobiohydrolase I with linker and carbohydrate binding module (CBM) from *A. fumigatus* cellobiohydrolase I (SEQ ID NOs: 84 and 85 for the fusion polypeptide DNA and amino acid sequences, respectively), a DNA fragment encoding *A. fumigatus* cellobiohydrolase I linker and CBM was assembled to the 3'-end of the gene encoding the *R. byssochlamydoides* cellobiohydrolase I using splicing overlap extension (50E) PCR.

The DNA fragment encoding the *A. fumigatus* cellobiohydrolase I linker and CBM was amplified using primer F-50E638 and primer R-50E638 shown below.

```
Primer F-SOE638:
                            (SEQ ID NO: 86)
5'-CAATC AACTC GACCT TCACC ACTTC GGGCT

CGAAC CCTGG AGGCG GAACG-3'

Primer R-SOE638:
                            (SEQ ID NO: 87)
5'-CTAGA TCTCG AGTTA CAAAC ACTGC GAGTA

GTAG-3'
```

The amplification of the DNA fragment encoding the *A. fumigatus* cellobiohydrolase I linker and CBM was performed using a PHUSION® High-Fidelity PCR Kit. The PCR solution was composed of 10 µl of 5× HF buffer, 4 µl of dNTPs (2.5 mM), 0.5 µl of PHUSION® DNA polymerase (0.2 units/µl), 0.25 µl of primer F-50E638 (100 µM), 0.25 µl of primer R-50E638 (100 µM), 10 µl of template DNA (pE596 cellobiohydrolase I, 1 ng/µl), and 25 µl of deionized water in a total volume of 50 µl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 239 bp PCR fragment encoding the *A. fumigatus* cellobiohydrolase I linker and CBM was excised from the gel and purified using a MinElute Gel Extraction Kit (QIAGEN Inc., Valencia, CA, USA).

A DNA fragment encoding the *R. byssochlamydoides* cellobiohydrolase I was amplified using primer F-pDau109 and primer R-50E637 shown below.

```
Primer F-pDau109:
                            (SEQ ID NO: 59)
5'CCACA CTTCT CTTCC TTCCT CAATC CTC-3'

Primer R-SOE637
                            (SEQ ID NO: 88)
5'-CGAAG TGGTG AAGGT CGAGT TGATT G-3'
```

The amplification of the DNA fragment encoding the *R. byssochlamydoides* wild-type cellobiohydrolase I was performed using a PHUSION® High-Fidelity PCR Kit. The PCR solution was composed of 10 µl of 5× HF buffer, 4 µl of dNTPs (2.5 mM), 0.5 µl of PHUSION® DNA polymerase (0.2 units/µl), 0.25 µl of primer F-pDAu109 (100 µM), 0.25 µl of primer R-50E637 (100 µM), 10 µl of template DNA (pE637-R. *byssochlamydoides* cellobiohydrolase I, 1 ng/µl), and 25 µl of deionized water in a total volume of 50 µl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 1658 bp fragment encoding the *R. byssochlamydoides* wild-type cellobiohydrolase I was excised from the gel and purified using a MinElute Gel Extraction Kit.

The two purified DNA fragments were assembled using SOE PCR and a PHUSION® High-Fidelity PCR Kit. The PCR solution was composed of 10 µl of 5× HF buffer, 4 µl of dNTPs (2.5 mM), 0.5 µl of PHUSION® DNA polymerase (0.2 units/µl), 0.25 µl of primer F-pDAu109 (100 µM), 0.25 µl of R-pDAu109 (100 µM), 2 µl of gel purified fragment encoding *A. fumigatus* cellobiohydrolase I linker and CBM, 2 µl of DNA fragment encoding *R. byssochlamydoides* cellobiohydrolase 1, and 31 µl of deionized water to give a final volume of 50 µl. The PCR was performed using a GeneAmp® PCR System 9700 programmed for 1 cycle at 98° C. for 2 min; then 10 cycles of 98° C. for 20 seconds, 65° C. for 20 seconds, and 72° C. for 4 minutes; then followed by 20 cycles of 98° C. for 20 seconds, 55° C. for 20 seconds, and 72° C. for 6 minutes. The PCR solution was then held at 6° C. until removed from the PCR machine.

The PCR generated DNA fragment was then digested with Bam HI (New England Biolabs, Ipswich, MA, USA) and XhoI (New England Biolabs, Ipswich, MA, USA) as follows. Twenty µl of PCR product were mixed with 2.3 µl buffer 3.1 (New England Biolabs, Ipswich, MA, USA), 0.8 µl of Bam HI, and 0.6 µl of XhoI and incubated at 37° C. overnight. The resulting DNA product was submitted to 1% agarose gel electrophoresis using TAE buffer. A band of approximately 1717 bp was excised from the gel and purified using a MinElute Gel Extraction Kit.

The 1717 bp fragment encoding the *R. byssochlamydoides* cellobiohydrolase I with linker and carbohydrate binding module (CBM) from *A. fumigatus* cellobiohydrolase I was cloned into pDAu109 digested with Bam HI and XhoI using T4 DNA ligase. The Bam HI-XhoI digested pDau109 and the Bam HI/XhoI fragment containing the *R. byssochlamydoides* cellobiohydrolase I with linker and carbohydrate binding module (CBM) from *A. fumigatus* cellobiohydrolase I coding sequence were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Two transformants were cultivated in LB medium supplemented with 0.15 mg of ampicillin per ml and plasmids were isolated using a QIAPREP® Spin Miniprep Kit.

The insertion of the DNA fragment encoding the *R. byssochlamydoides* cellobiohydrolase I with linker and carbohydrate binding module (CBM) from *A. fumigatus* cellobiohydrolase I into pDAu109 was verified by sequencing. The isolated plasmids were sequenced using an Applied Biosystems 3730xl DNA Analyzer with vector primers F-pDau109 and R-pDau109 in order to determine a representative plasmid that was free of PCR errors and contained the correct insertion.

One plasmid clone free of PCR errors and containing the DNA fragment encoding the *R. byssochlamydoides* cellobiohydrolase I with linker and carbohydrate binding module (CBM) from *A. fumigatus* cellobiohydrolase I was chosen and designated plasmid pE638. The corresponding hybrid polypeptide was designated as RC1-638.

Example 18: Site-Directed Mutagenesis of the *Aspergillus fumigatus* Cellobiohydrolase I (AC1-660 and AC1-661) and of the Fusion Polypeptide of *Rasamsonia byssochlamydoides* Cellobiohydrolase I with Linker and Carbohydrate Binding Module from *Aspergillus fumigatus* Cellobiohydrolase I (RC1-899)

Plasmid pE596 (Example 15) was used for the construction of the *A. fumigatus* cellobiohydrolase I variants AC1-660 and AC1-661.

AC1-660 (SEQ ID NO: 89 for the mutant DNA sequence and SEQ ID NO: 90 for the variant) contains a Y→W substitution at position 501 (corresponding to Y5W of the carbohydrate binding module) and was generated by replacing a TAC codon (Y501) with a TGG codon (501W).

AC1-661 (SEQ ID NO: 91 for the mutant DNA sequence and SEQ ID NO: 92 for the variant) contains a Y→W substitution at position 527 (corresponding to Y31W of the carbohydrate binding module) and was generated by replacing a TAC codon (Y527) with a TGG codon (527W).

Plasmid pE638 (Example 17) was used to generate *R. byssochlamydoides-A. fumigatus* fusion cellobiohydrolase I variant (RC1-899). RC1-899 (SEQ ID NO: 93 for the mutant DNA sequence and SEQ ID NO: 94 for the variant) contains a Y→W substitution at position 516 (corresponding to Y31W of the carbohydrate binding module) and was generated by replacing a TAC codon (Y516) with a TGG codon (516W).

Two synthetic primers for each site-directed mutagenesis were designed using a SOE primer design tool. Site-directed mutagenesis of the synthetic gene encoding the wild-type *A.*

*fumigatus* cellobiohydrolase I was facilitated by PCR amplifications of pE596 using the primers and procedure described below. Site-directed mutageneis of the fusion gene encoding *R. byssochlamydoides* cellobiohydrolase I with linker and carbohydrate binding module (CBM) from *A. fumigatus* cellobiohydrolase I was facilitated by PCR amplification of pE638 using primers F-Y527W and R-Y527W and the procedure described below.

```
Primer F-Y501W:
                                    (SEQ ID NO: 95)
5'-GTACA GGTGT GGCCC AGCAC TGGGG

ACAGT GTGGC GGTAT CGG-3'

Primer R-Y501W:
                                    (SEQ ID NO: 96)
5'-GTGCT GGGCC ACACC TGTAC CTCCA

GGGTT G-3'

Primer F-Y527W:
                                    (SEQ ID NO: 97)
5'-ATACC TGTCA GAAAT TGAAC GACTG

GTACT CGCAG TGTTT GTAAG CTTC-3'

Primer R-Y527W:
                                    (SEQ ID NO: 98)
5'-GTCGT TCAAT TTCTG ACAGG TATAA

GGCGA TG-3'
```

The mutation was introduced by PCR using a PHUSION® High-Fidelity PCR Kit (New England Biolabs Inc. MA, USA). The PCR solutions were composed of 10 µl of 5× HF buffer, 4 µl of dNTPs (2.5 mM), 0.5 µl of PHUSION® DNA polymerase (0.2 units/µl), 0.25 µl of primer F-Y501W or F-Y527W (100 µM), 0.25 µl of primer R-Y501W or R-Y527W (100 µM), 5 µl of template DNA (pE596, 1 ng/µl or pE638, 1 ng/µl), and 30 µl of deionized water in a total volume of 50 µl. he PCR was performed using an Applied Biosystems® Veriti® 96 well thermal cycler programmed for 1 cycle at 98° C. for 30 seconds; and 19 cycles each at 98° C. for 30 seconds, 55° C. for 1 minute, and 72° C. for 7 minutes. The PCR solution was then held at 8° C. until removed from the PCR machine.

Following the PCR, 10 units of Dpn I were added directly to the PCR solution and incubated at 37° C. for 1 hour. Then 1 µl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.10 mg of ampicillin per ml and plasmids were isolated using a QIAPREP® Spin Miniprep Kit (QIAGEN Inc., Valencia, CA, USA).

The isolated mutant plasmids of pE596 were sequenced using an Applied Biosystems 3730xl DNA Analyzer (Applied Biosystems, Foster City, CA, USA) with primers F-pDau109 (SEQ ID NO: 59), R-pDau109 (SEQ ID NO: 58), F-pE596 (SEQ ID NO: 80) and R-pE596 (SEQ ID NO: 81), in order to determine a representative plasmid that was free of PCR errors and contained the desired mutations.

```
Primer F-pDau109:
                                  (SEQ ID NO: 59)
5'CCACACTTCTCTTCCTTCCTCAATCCTC-3'

Primer R-pDau109:
                                  (SEQ ID NO: 58)
5'ATCCTCAATTCCGTCGGTCGA-3'

Primer F-pE596
                                  (SEQ ID NO: 80)
5'GTGAT ACACC CGGAC AGGTG ATGTG-3'

Primer R-pE596
                                  (SEQ ID NO: 81)
5'-CCATA TCGAT CCGAC GAGTA GGTTC-3'
```

One plasmid clone free of PCR errors and containing the TAC (Y501) to TGG (501W) mutation (corresponding to Y5W of the carbohydrate binding module) was chosen and designated plasmid pE660 and the corresponding polypeptide was designated as AC1-660.

One plasmid clone free of PCR errors and containing the TAC (Y527) to TGG (527W) mutation corresponding to Y31W of the carbohydrate binding module) was chosen and designated plasmid pE661 and the corresponding polypeptide was designated as AC1-661.

The isolated mutant plasmids of pE638 were sequenced using an Applied Biosystems 3730xl DNA Analyzer (Applied Biosystems, Foster City, CA, USA) with primers F-pDau109 (SEQ ID NO: 59), R-pDau109 (SEQ ID NO: 58), F-pE638 (SEQ ID NO: 99) and R-pE638 (SEQ ID NO: 100), in order to determine a representative plasmid that was free of PCR errors and contained the desired mutations.

```
Primer F-pDau109:
                                  (SEQ ID NO: 59)
5'CCACACTTCTCTTCCTTCCTCAATCCTC-3'

Primer R-pDau109:
                                  (SEQ ID NO: 58)
5'ATCCTCAATTCCGTCGGTCGA-3'

Primer F-pE638:
                                  (SEQ ID NO: 99)
5'CCTCA GCCGA ACTCC GACAT TGC-3'

Primer R-pE638:
                                  (SEQ ID NO: 100)
5'-GCAAT GTCGG AGTTC GGCTG AGG-3'
```

One plasmid clone free of PCR errors and containing the TAC (Y516) to TGG (516W) mutation (corresponding to Y31W of the carbohydrate binding module) was chosen and designated plasmid pE899 and the corresponding polypeptide was designated as RC1-899.

Example 19: Expression of the Wild Type *A. fumigatus* Cellobiohydrolase I AC1-596, the *A. fumigatus* Variants AC1-660 and AC1-661, *R. emersonii* Fusion Protein Variant PC1-668 and the *R. byssochlamydoides-A. fumigatus* Fusion Protein Variant RC1-899

The expression plasmids pE596 (Example 15), pE660 and pE661 (Example 18), pE668 (Example 13) and pE899 (Example 18) were transformed into *Aspergillus oryzae* MT3568 protoplasts according to Christensen et al., 1988, supra and WO 2004/032648. *A. oryzae* MT3568 protoplasts were prepared according to the method of EP 0238023 B1, pages 14-15.

Transformants were purified on COVE sucrose plates without Triton X-100 through single conidia. Spores of the transformants were inoculated into 96 deep well plates containing 0.50 ml of DAP-4C medium and incubated stationary at 34° C. for 6 days.

Production of the wild type *A. fumigatus* cellobiohydrolase I AC1-596, *A. fumigatus* cellobiohydrolase variants AC1-660 and AC1-661, and *R. byssochlamydoides-A. fumigatus* fusion cellobiohydrolase I variant RC1-899 by the transformants were analyzed from culture supernatants of the 96 deep well cultivations. Expression was verified by measuring released reducing sugars from hydrolysis of microcrystalline cellulose. The hydrolysis was performed in 96 well microtiter plates (NUNC Thermo Fisher Scientific, Roskilde, Denmark) at 32° C. and 1100 rpm. Each hydrolysis reaction mixture contained 170 μl of microcrystalline cellulose at 90 g/liter in 50 mM sodium acetate pH 5.0, 0.01% TRITON® X-100, 20 μl of culture supernatant, and 60 μl of 50 mM sodium acetate pH 5.0, 0.01% TRITON® X-100. The plates were sealed with tape. The hydrolysis reaction was stopped by spinning the plate at 3500 rpm for 3 minutes. Then 12.5 μl of the reaction supernatant were added to 37.5 μl MQ water in a 96 well PCR plate (Thermo Fisher Scientific, Roskilde, Denmark). To this mixture 75 μl of stop solution was added. The stop solution was composed of 15 mg/ml 4-hydroxybenzhydrazide (Sigma Chemical Co., Inc., St. Louis, MO, USA), 50 mg/ml K-Na-tartrate (Sigma Chemical Co., Inc., St. Louis, MO, USA) in 2% (w/v) NaOH. The plate was sealed with a lid and the mixture was incubated at 95° C. for 10 minutes and 5 minutes at 20° C. Then 100 μl was transferred to a microtiter plate and absorbance at 410 nm was measured using a SPECTRA-MAX® Plus 384 (Molecular Devices, Sunnyvale, CA, USA). The concentration of reducing sugar was proportional to the absorbance at 410 nm of the oxidized 4-hydroxybenzhydrazide. The reducing sugar content in the culture supernatants was measured by adding 1 μl of culture supernatant to a mixture of 75 μl of stop solution and 49 μl of milliQ water in a 96 well PCR plate. The plate was sealed with a lid and the mixture was incubated at 95° C. for 10 minutes and 5 minutes at 20° C. Then 100 μl was transferred to a microtiter plate and the absorbance at 410 nm was measured. The absorbance at 410 nm from the cell culture supernatant was subtracted from the absorbance at 410 nm of the hydrolysis reaction, to measure the amount of reducing sugar released by the enzymes.

Based on the level of hydrolysis of the microcrystalline cellulose one transformant expressing the wild type *A. fumigatus* cellobiohydrolase I was selected and designated *A. oryzae* AC1-596.

Based on the level of hydrolysis of the microcrystalline cellulose, one transformant expressing the *A. fumigatus* cellobiohydrolase I variant AC1-660 was selected and designated *A. oryzae* AC1-660.

Based on the level of hydrolysis of the microcrystalline cellulose, one transformant expressing the *A. fumigatus* cellobiohydrolase I variant AC1-661 was selected and designated *A. oryzae* AC1-661.

Based on the level of hydrolysis of the microcrystalline cellulose, one transformant expressing the *R. emersonii-T. reesei* fusion cellobiohydrolase I variant PC1-668 was selected and designated *A. oryzae* PC1-668.

Based on the level of hydrolysis of the microcrystalline cellulose, one transformant expressing the *R. byssochlamydoides-A. fumigatus* fusion cellobiohydrolase I variant RC1-899 was selected and designated *A. oryzae* RC1-899.

For larger scale production, *A. oryzae* AC1-596, *A. oryzae* AC1-660, *A. oryzae* AC1-661, *A. oryzae* PC1-668 or *A. oryzae* RC1-899 spores were spread onto COVE sucrose slants and incubated for five days at 37° C. The confluent spore slants were washed twice with 5 ml MQ water with 0.01% TWEEN® 20. The spore suspensions were then used to inoculate a 500 ml flask containing 150 ml of G2-Gly medium. The pre-culture was incubated at 30° C. with constant shaking at 200 rpm. After one day, the pre-culture was used to inoculate four 500 ml flasks containing 200 ml of DAP-4C medium. At day four post-inoculation, the culture broths were collected by filtration through a bottle top MF75 Supor MachV 0.2 μm PES filter.

Example 20: Comparison of the Effect of Hybrid Polypeptides PC1-147, PC1-499, PC1-500, and PC1-688 on the Hydrolysis of Unwashed PCS by a Cellulase Enzyme Composition The hybrid polypeptides PC1-499, PC1-500, and PC1-668 (containing a substitution corresponding to Y32W, Y5W, and Y13W of the cellulose binding module, respectively) were added to the cellulolytic enzyme composition without cellobiohydrolase I (Example 11) at 35° C., 50° C. and 60° C. using unwashed PCS as a substrate, and compared against the hybrid polypeptide PC1-147 (lacking substitutions corresponding to Y5W, Y13W, or Y32W of the CBM). Each cellobiohydrolase I was added individually at 3.33 mg enzyme protein per g cellulose to 5.67 mg enzyme protein of the cellulase enzyme composition without cellobiohydrolase I per g cellulose.

The assay was performed as described in Example 11. The reactions with unwashed PCS (20% total solids) were conducted for 72 hours at 35° C., 50° C. and 60° C. in 71 mM sodium acetate pH 5.0 buffer containing 1 mM manganese sulfate. All reactions were performed in quadruplicate and shaking at 200 rpm throughout the hydrolysis.

The results shown in FIG. 5 demonstrated that the cellulase enzyme composition containing the hybrid polypeptide PC1-668 (containing an *R. emersonii* cellobiohydrolase I catalytic domain linked to a *T. reesei* carbohydrate binding module variant with a substitution corresponding to Y13W of the CBM) had significantly higher cellulose conversion at all temperatures compared to the cellulase enzyme composition that included the hybrid polypeptide PC1-147 lacking either substitution corresponding to Y5W, Y13W, or Y32W of the CBM. As previously observed, the hybrid polypeptide PC1-499 and the hybrid polypeptide PC1-500 (containing an *R. emersonii* cellobiohydrolase I catalytic domain linked to a *T. reesei* carbohydrate binding module variant with a substitution corresponding to Y32W or Y5W of the CBM, respectively) had significantly higher cellulose conversion at all temperatures compared to PC1-147.

Example 21: Comparison of the Effect of Variant Polypeptide AC1-660, Variant Polypeptides AC1-661, and Wild-Type Polypeptide AC1-596 on the Hydrolysis of Unwashed PCS by a Cellulase Enzyme Composition The variant polypeptides AC1-660 and AC1-661 (containing a substitution corresponding to Y5W and Y31W of the cellulose binding module, respectively) were added to the cellulolytic enzyme composition without cellobiohydrolase I (Example 11) at 35° C., 50° C. and 60° C. using unwashed PCS as a substrate, and compared against the wild-type polypeptide AC1-596 (lacking either substitution corresponding to Y5W and Y31W of the CBM). Each cellobiohydrolase I was added individually at 3.33 mg enzyme protein per g cellulose to 5.67 mg enzyme protein of the cellulase enzyme composition without cellobiohydrolase I per g cellulose.

The assay was performed as described in Example 11. The reactions with unwashed PCS (20% total solids) were conducted for 72 hours at 35° C., 50° C. and 60° C. in 71 mM sodium acetate pH 5.0 buffer containing 1 mM manganese sulfate. All reactions were performed in quadruplicate and shaking at 200 rpm throughout the hydrolysis.

The results shown in FIG. 6 demonstrated that the cellulase enzyme composition containing the variant polypeptide AC1-660 (containing an *A. fumigatus* cellobiohydrolase I variant with a substitution corresponding to Y5W of the CBM) had significantly higher cellulose conversion at all temperatures compared to the cellulase enzyme composition that included the wild-type polypeptide AC1-596 lacking either substitution corresponding to Y5W or Y31W of the CBM. In addition, the variant polypeptide AC1-661 (containing an *A. fumigatus* cellobiohydrolase I variant with a substitution corresponding to Y31W of the CBM) had significantly higher cellulose conversion at all temperatures compared to AC1-596.

Example 22: Comparison of the Effect of Variant Polypeptide RC1-899, and Hybrid Polypeptide PC1-147 on the Hydrolysis of Unwashed PCS by a Cellulase Enzyme Composition The variant polypeptides RC1-899 (*R. byssochlamydoides* cellobiohydrolase I catalytic domain linked to the *A. fumigatus* carbohydrate binding module with a substitution corresponding to Y31W of the CBM) was added to the cellulolytic enzyme composition without cellobiohydrolase I (Example 11) at 35° C., 50° C. and 60° C. using unwashed PCS as a substrate, and compared against the hybrid polypeptide PC1-147 (containing an *R. emersonii* cellobiohydrolase I catalytic domain linked to a *T. reesei* carbohydrate binding module variant lacking a substitution corresponding to Y31W of the CBM). Each cellobiohydrolase I was added individually at 2, 3, and 4 mg enzyme protein per g cellulose to 5.108 mg enzyme protein of the cellulase enzyme composition without cellobiohydrolase I per g cellulose.

The assay was performed as described in Example 11. The reactions with unwashed PCS (20% total solids) were conducted for 72 hours at 35° C., 50° C. and 60° C. in 80 mM sodium acetate pH 5.0 buffer containing 1 mM manganese sulfate. All reactions were performed in quadruplicate and shaking at 200 rpm throughout the hydrolysis.

The results shown in FIG. 7 demonstrated that the cellulase enzyme composition containing the variant polypeptide RC1-899 had significantly higher cellulose conversion at 35° C. and 50° C. compared to the cellulase enzyme composition that included the hybrid polypeptide PC1-147.

Example 23: Determination of Td by Differential Scanning Calorimetry of the *R. Byssochlamydoides*-*A. fumigatus* Fusion Protein Variant RC1-899

The thermostability of RC1-899 was determined by Differential Scanning calorimetry (DSC) using a VP-Capillary Differential Scanning calorimeter (MicroCal Inc., Piscataway, NJ, USA). The thermal denaturation temperature, Td (° C.), was taken as the top of denaturation peak (major endothermic peak) in thermograms (Cp vs. T) obtained after heating enzyme solutions (approx. 0.5 mg/ml) in buffer (50 mM acetate buffer pH 5.0) at a constant programmed heating rate of 200 K/hr.

Sample- and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 100° C. Denaturation temperatures were determined at an accuracy of approximately +/−1° C.

The results demonstrated that the *R. byssochlamydoides- A. fumigatus* fusion cellobiohydrolase I has a Td of approximately 77° C. which is comparable to the improved Td of PC1-147 (within approximately 1 deg C.).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

---

What is claimed is:

1. A polypeptide comprising or consisting of the polypeptide of SEQ ID NO: 61 or amino acids 19 to 519 of SEQ ID NO: 61.

2. A polypeptide comprising or consisting of the polypeptide of SEQ ID NO: 63 or amino acids 19 to 519 of SEQ ID NO: 63.

3. A polypeptide comprising or consisting of the polypeptide of SEQ ID NO: 73 or amino acids 19 to 519 of SEQ ID NO: 73.

4. A polypeptide comprising or consisting of the polypeptide of SEQ ID NO: 94 or amino acids 19 to 521 of SEQ ID NO: 94 the mature polypeptide thereof.

5. A carbohydrate binding module (CBM) variant of a parent CBM, wherein the CBM variant comprises a substitution at one or more positions of the parent CBM, wherein the one or more positions correspond to positions 5, 13, 31 and 32 of the polypeptide of SEQ ID NO: 4, wherein the CBM variant has carbohydrate binding activity, wherein the CBM variant has:

(i) at least 95%, but less than 100%, sequence identity to the polypeptide of SEQ ID NO: 4; or (ii) at least 95%, but less than 100%, sequence identity to the polypeptide of SEQ ID NO: 20, and wherein the CBM variant comprises a Tyr or Phe at the position corresponding to position 5 of the polypeptide of SEQ ID NO: 4, wherein the CBM variant comprises a Tyr, Phe, or Trp at the position corresponding to position 13 of the polypeptide of SEQ ID NO: 4, wherein the CBM variant comprises a Tyr or Phe at the position corresponding to position 31 of the polypeptide of SEQ ID NO: 4, and wherein the CBM variant comprises a Tyr or Trp at a position corresponding to position 32 of the polypeptide of SEQ ID NO: 4.

6. The CBM variant of claim 5, wherein the CBM variant has:

(i) at least 96%, but less than 100%, sequence identity to the polypeptide of SEQ ID NO: 4; or (ii) at least 96%, but less than 100%, sequence identity to the polypeptide of SEQ ID NO: 20.

7. The CBM variant of claim 5, wherein the CBM variant has:

(i) at least 97%, but less than 100%, sequence identity to the polypeptide of SEQ ID NO: 4; or (ii) at least 97%, but less than 100%, sequence identity to the polypeptide of SEQ ID NO: 20.

8. The CBM variant of claim 5, wherein the CBM variant has:

(i) at least 98%, but less than 100%, sequence identity to the polypeptide of SEQ ID NO: 4; or (ii) at least 98%, but less than 100%, sequence identity to the polypeptide of SEQ ID NO: 20.

9. The CBM variant of claim 5, wherein the CBM variant has:

(i) at least 99%, but less than 100%, sequence identity to the polypeptide of SEQ ID NO: 4; or (ii) at least 99%, but less than 100%, sequence identity to the polypeptide of SEQ ID NO: 20.

10. A hybrid polypeptide having cellobiohydrolase activity, comprising:

(a) a cellobiohydrolase catalytic domain located at the N-terminal end of the hybrid polypeptide; and (b) a carbohydrate binding module (CBM) variant located at the C-terminal end of the hybrid polypeptide, wherein the catalytic domain is heterologous to the CBM variant, wherein the cellobiohydrolase catalytic domain has at least 95% sequence identity to amino acids 1 to 437 of the polypeptide of SEQ ID NO: 46, wherein the CBM variant is a variant of a parent CBM comprising a substitution at one or more positions of the parent CBM, wherein the one or more positions correspond to positions 5, 13, 31 and 32 of the polypeptide of SEQ ID NO: 4, wherein the CBM variant comprises a Tyr or Phe at the position corresponding to position 5 of the polypeptide of SEQ ID NO: 4, wherein the CBM variant comprises a Tyr, Phe, or Trp at the position corresponding to position 13 of the polypeptide of SEQ ID NO: 4, wherein the CBM variant comprises a Tyr or Phe at the position corresponding to position 31 of the polypeptide of SEQ ID NO: 4, and wherein the CBM variant comprises a Tyr or Trp at a position corresponding to position 32 of the polypeptide of SEQ ID NO: 4, and wherein the parent CBM has at least 95% sequence identity to the polypeptide of SEQ ID NO: 4 or the polypeptide of SEQ ID NO: 20 and wherein the CBM variant has at least 95%, but less than 100%, sequence identity to the polypeptide of SEQ ID NO: 4 or the polypeptide of SEQ ID NO: 20.

11. The hybrid polypeptide of claim 10, wherein the heterologous catalytic domain has at least 96% sequence identity to amino acids 1 to 437 of the polypeptide of SEQ ID NO: 46 and has cellobiohydrolase activity.

12. The hybrid polypeptide of claim 10, wherein the heterologous catalytic domain has at least 97% sequence identity to amino acids 1 to 437 of the polypeptide of SEQ ID NO: 46 and has cellobiohydrolase activity.

13. The hybrid polypeptide of claim 10, wherein the heterologous catalytic domain has at least 98% sequence identity to amino acids 1 to 437 of the polypeptide of SEQ ID NO: 46 and has cellobiohydrolase activity.

14. The hybrid polypeptide of claim 10, wherein the heterologous catalytic domain has at least 99% sequence identity to amino acids 1 to 437 of the polypeptide of SEQ ID NO: 46 and has cellobiohydrolase activity.

15. The hybrid polypeptide of claim 10, wherein the heterologous catalytic domain comprises amino acids 1 to 437 of the polypeptide of SEQ ID NO: 46.

16. The hybrid polypeptide of claim 10, wherein the heterologous catalytic domain consists of amino acids 1 to 437 of the polypeptide of SEQ ID NO: 46.

17. The hybrid polypeptide of claim 10, wherein the CBM variant has at least 95%, but less than 100%, sequence identity to the polypeptide of SEQ ID NO: 4.

18. The hybrid polypeptide of claim 10, wherein the CBM variant has at least 97%, but less than 100%, sequence identity to the polypeptide of SEQ ID NO: 4.

19. The hybrid polypeptide of claim 10, wherein the CBM variant has at least 99%, but less than 100%, sequence identity to the polypeptide of SEQ ID NO: 4.

20. The hybrid polypeptide of claim 10, wherein the CBM variant has at least 95%, but less than 100%, sequence identity to the polypeptide of SEQ ID NO: 20.

21. The hybrid polypeptide of claim 10, wherein the CBM variant has at least 97%, but less than 100%, sequence identity to the polypeptide of SEQ ID NO: 20.

22. The hybrid polypeptide of claim 10, wherein the CBM variant has at least 99%, but less than 100%, sequence identity to the polypeptide of SEQ ID NO: 20.

23. The hybrid polypeptide of claim 10, wherein the parent CBM has at least 95% sequence identity to the polypeptide of SEQ ID NO: 4.

24. The hybrid polypeptide of claim 10, wherein the parent CBM has at least 97% sequence identity to the polypeptide of SEQ ID NO: 4.

25. The hybrid polypeptide of claim 10, wherein the parent CBM has at least 99% sequence identity to the polypeptide of SEQ ID NO: 4.

26. The hybrid polypeptide of claim 10, wherein the parent CBM comprises the polypeptide of SEQ ID NO: 4.

27. The hybrid polypeptide of claim 10, wherein the parent CBM consists of the polypeptide of SEQ ID NO: 4.

28. The hybrid polypeptide of claim 10, wherein the parent CBM has at least 95% sequence identity to the polypeptide of SEQ ID NO: 20.

29. The hybrid polypeptide of claim 10, wherein the parent CBM has at least 97% sequence identity to the polypeptide of SEQ ID NO: 20.

30. The hybrid polypeptide of claim 10, wherein the parent CBM has at least 99% sequence identity to the polypeptide of SEQ ID NO: 20.

31. The hybrid polypeptide of claim 10, wherein the parent CBM comprises the polypeptide of SEQ ID NO: 20.

32. The hybrid polypeptide of claim 10, wherein the parent CBM consists of the polypeptide of SEQ ID NO: 20.

33. A composition comprising the hybrid polypeptide of claim 10.

* * * * *